(12) United States Patent
Wild et al.

(10) Patent No.: US 8,841,415 B2
(45) Date of Patent: Sep. 23, 2014

(54) CRYSTAL FORM OF THE AMYLOID PRECURSOR PROTEIN INTRACELLULAR DOMAIN (AICD) IN COMPLEX WITH HUMAN FE65-PTB2

(75) Inventors: Klemens Wild, Bammental (DE); Jens Radzimanowski, Grenoble (FR); Irmgard Sinning, Bammental (DE); Konrad Beyreuther, Heidelberg (DE)

(73) Assignee: Universität Heidelberg, Heidelberg (DE)

( * ) Notice: Subject to any disclaimer, the term of this patent is extended or adjusted under 35 U.S.C. 154(b) by 238 days.

(21) Appl. No.: 12/864,563

(22) PCT Filed: Jan. 29, 2009

(86) PCT No.: PCT/EP2009/000577
§ 371 (c)(1),
(2), (4) Date: Nov. 22, 2010

(87) PCT Pub. No.: WO2009/095239
PCT Pub. Date: Aug. 6, 2009

(65) Prior Publication Data
US 2011/0118439 A1      May 19, 2011

(30) Foreign Application Priority Data

Jan. 30, 2008   (EP) .................................... 08001731
Jul. 7, 2008    (EP) .................................... 08012257

(51) Int. Cl.
*C07K 14/00*    (2006.01)
*G01N 33/02*    (2006.01)
*C07K 14/47*    (2006.01)

(52) U.S. Cl.
CPC ......... *C07K 14/4702* (2013.01); *C07K 14/4711* (2013.01); *C07K 2299/00* (2013.01)
USPC .............................................. 530/350; 436/4

(58) Field of Classification Search
None
See application file for complete search history.

(56) References Cited

U.S. PATENT DOCUMENTS 6,717,031 B2 *   4/2004   Games et al. .................... 800/12
2008/0201123 A1 * 8/2008  Cosgrove ........................ 703/11

FOREIGN PATENT DOCUMENTS

EP        1 669 085 A      6/2006

OTHER PUBLICATIONS

GenPept Accession No. 1303338A, GI:225456, Oct. 1996, 1 page.*
Definition of "correspond", obtained from education.yahoo.com/reference/dictionary/entry/correspond; last viewed on Nov. 7, 2011; 1 page.*
GenPept Accession No. O00213, Jan. 2007; 3 pages.*
McLoughlin, Declan M. et al.: "The FE65 proteins and Alzheimer's disease," Journal of Neuroscience Research, Mar. 2008, vol. 86, No. 4, pp. 744-754.
Zambrano, N. et al.: "Interaction of the Phosphotyrosine Interaction/Phosphotyrosine Binding-Related domains of FE65 With Wild-Type and Mutant Alzheimer's Beta-Amyloid Precursor Proteins," Journal of Biological Chemistry, American Society of Biochemical Biologists, Birmingham, U.S., vol. 272, No. 10, Mar. 7, 1997, pp. 6399-6405.
Ro, Seung-Hyun & Ha, Nam-Chul: "High-level production and initial crystallization of a Fe65 PTB domain," Journal of Life Science, vol. 17, No. 1, 2007, pp. 18-23.
McPherson, A.: "Current Approaches to Macromolecular Crystallization," European Journal of Biochemistry, Berlin, DE, vol. 189, 1990, pp. 1-23.
Wang, Yongcheng et al.: "The X-ray structure of an an antiparallel dimer of the human amyloid precursor protein E2 domain," Molecular Cell, vol. 15, No. 3, Aug. 13, 2004, pp. 343-353.
Keil, Cora et al.: "Cloning, expression, crystallization and initial crystallographic analysis of the C-terminal domain of the amyloid precursor protein APP," ACTA Crystallographica Section D Biological Crystallography, vol. 60, No. Part 9, Sep. 2004, pp. 1614-1617.
Radzimanowski, Jens et al.: "Overproduction, purification, crystallization and preliminary X-ray analysis of human Fe65-PTB2 in complex with the amyloid precursor protein intracellular domain," Acta Crystallographica Section F: Structural Biology and Crystallization Communications On-line, Blackwell Munksgaard, Copenhagen, DK, vol. 64, No. Part 5, May 1, 2008, pp. 409-412.
Radzimanowski, Jens et al.: "Structure of the intracellular domain of the amyloid precursor protein in complex with Fe65-PTB," EMBO Reports, Nature Publishing Group, London, GB, vol. 9, No. 11, Nov. 1, 2008, pp. 1134-1140.
Cao, Xinwei, et al., "Dissection of Amyloid-β Precursor Protein-Dependent Transcriptional Transactivation," The Journal of Biological Chemistry, Jun. 2004, vol. 279, No. 23, pp. 24601-24611.

* cited by examiner

*Primary Examiner* — David J Steadman
(74) *Attorney, Agent, or Firm* — McDonnell Boehnen Hulbert & Berghoff LLP

(57) ABSTRACT

The present invention relates to a three-dimensional structure of the intracellular domain (AICD) of human amyloid precursor protein (APP695) in complex with human Fe65-PTB2 (i.e. a protein-complex comprising the intracellular domain (AICD) of human amyloid precursor protein (APP695) and the human Fe65-PTB2), as well as to methods and uses of said three-dimensional structure for identifying ligands which modify the interaction between the AICD and the Fe65-PTB2. Moreover, the present invention relates to pharmaceutical compositions which contain one or more of such identified ligands for the prevention or treatment of neurodegenerative disorders.

2 Claims, 48 Drawing Sheets

FIG. 1A

```
ATOM      1  N   ASN A 537     -32.304  41.221  14.150  1.00 78.74           N
ATOM      2  CA  ASN A 537     -31.307  41.137  15.255  1.00 78.67           C
ATOM      3  CB  ASN A 537     -31.217  39.693  15.780  1.00 78.93           C
ATOM      4  CG  ASN A 537     -30.612  39.603  17.188  1.00 79.49           C
ATOM      5  OD1 ASN A 537     -30.370  40.619  17.855  1.00 78.67           O
ATOM      6  ND2 ASN A 537     -30.378  38.370  17.646  1.00 79.49           N
ATOM      7  C   ASN A 537     -29.933  41.684  14.825  1.00 78.35           C
ATOM      8  O   ASN A 537     -29.760  42.900  14.724  1.00 78.34           O
ATOM      9  N   GLU A 538     -28.976  40.797  14.544  1.00 77.88           N
ATOM     10  CA  GLU A 538     -27.595  41.205  14.229  1.00 77.61           C
ATOM     11  CB  GLU A 538     -26.664  39.990  14.117  1.00 77.49           C
ATOM     12  CG  GLU A 538     -27.182  38.857  13.247  1.00 78.01           C
ATOM     13  CD  GLU A 538     -26.174  37.732  13.083  1.00 78.55           C
ATOM     14  OE1 GLU A 538     -25.446  37.434  14.057  1.00 80.12           O
ATOM     15  OE2 GLU A 538     -26.111  37.140  11.977  1.00 79.77           O
ATOM     16  C   GLU A 538     -27.475  42.094  12.987  1.00 76.92           C
ATOM     17  O   GLU A 538     -28.288  41.999  12.065  1.00 77.13           O
ATOM     18  N   LEU A 539     -26.462  42.958  12.981  1.00 76.04           N
ATOM     19  CA  LEU A 539     -26.189  43.845  11.844  1.00 75.21           C
ATOM     20  CB  LEU A 539     -25.511  45.140  12.309  1.00 74.91           C
ATOM     21  CG  LEU A 539     -26.314  46.051  13.242  1.00 74.03           C
ATOM     22  CD1 LEU A 539     -25.386  46.896  14.098  1.00 73.66           C
ATOM     23  CD2 LEU A 539     -27.305  46.922  12.469  1.00 73.24           C
ATOM     24  C   LEU A 539     -25.329  43.150  10.787  1.00 74.81           C
ATOM     25  O   LEU A 539     -25.489  43.390   9.586  1.00 74.83           O
ATOM     26  N   VAL A 540     -24.412  42.303  11.248  1.00 74.07           N
ATOM     27  CA  VAL A 540     -23.548  41.517  10.369  1.00 73.43           C
ATOM     28  CB  VAL A 540     -22.143  42.192  10.114  1.00 73.43           C
ATOM     29  CG1 VAL A 540     -22.288  43.531   9.383  1.00 72.79           C
ATOM     30  CG2 VAL A 540     -21.347  42.364  11.421  1.00 73.08           C
ATOM     31  C   VAL A 540     -23.363  40.115  10.960  1.00 73.06           C
ATOM     32  O   VAL A 540     -23.564  39.909  12.172  1.00 73.08           O
ATOM     33  N   GLN A 541     -22.978  39.168  10.101  1.00 72.21           N
ATOM     34  CA  GLN A 541     -22.697  37.792  10.519  1.00 71.60           C
ATOM     35  CB  GLN A 541     -22.368  36.904   9.313  1.00 71.71           C
ATOM     36  CG  GLN A 541     -23.447  36.870   8.212  1.00 72.07           C
ATOM     37  CD  GLN A 541     -23.066  35.991   7.010  1.00 72.65           C
ATOM     38  OE1 GLN A 541     -23.864  35.821   6.080  1.00 73.58           O
ATOM     39  NE2 GLN A 541     -21.846  35.433   7.025  1.00 72.47           N
ATOM     40  C   GLN A 541     -21.561  37.741  11.553  1.00 70.53           C
ATOM     41  O   GLN A 541     -20.613  38.542  11.504  1.00 70.61           O
ATOM     42  N   LYS A 542     -21.681  36.797  12.485  1.00 68.91           N
ATOM     43  CA  LYS A 542     -20.777  36.667  13.625  1.00 67.25           C
ATOM     44  CB  LYS A 542     -21.237  35.502  14.508  1.00 67.40           C
ATOM     45  CG  LYS A 542     -22.687  35.636  14.958  1.00 68.27           C
ATOM     46  CD  LYS A 542     -23.336  34.299  15.297  1.00 69.20           C
ATOM     47  CE  LYS A 542     -24.813  34.485  15.624  1.00 69.75           C
ATOM     48  NZ  LYS A 542     -25.297  33.470  16.595  1.00 69.61           N
ATOM     49  C   LYS A 542     -19.301  36.508  13.223  1.00 66.00           C
ATOM     50  O   LYS A 542     -18.973  35.916  12.181  1.00 66.06           O
ATOM     51  N   PHE A 543     -18.429  37.052  14.067  1.00 64.00           N
ATOM     52  CA  PHE A 543     -16.978  37.056  13.861  1.00 61.98           C
ATOM     53  CB  PHE A 543     -16.390  38.368  14.377  1.00 60.59           C
ATOM     54  CG  PHE A 543     -16.868  39.559  13.622  1.00 59.01           C
ATOM     55  CD1 PHE A 543     -16.214  39.968  12.467  1.00 57.47           C
ATOM     56  CE1 PHE A 543     -16.671  41.058  11.754  1.00 56.88           C
```

FIG. 1B

```
ATOM     57  CZ   PHE A 543     -17.797  41.742  12.186  1.00 56.88    C
ATOM     58  CE2  PHE A 543     -18.466  41.325  13.326  1.00 55.46    C
ATOM     59  CD2  PHE A 543     -18.004  40.240  14.027  1.00 55.86    C
ATOM     60  C    PHE A 543     -16.333  35.892  14.574  1.00 61.45    C
ATOM     61  O    PHE A 543     -16.534  35.714  15.779  1.00 61.88    O
ATOM     62  N    GLN A 544     -15.562  35.101  13.834  1.00 60.44    N
ATOM     63  CA   GLN A 544     -14.878  33.938  14.405  1.00 59.57    C
ATOM     64  CB   GLN A 544     -14.792  32.777  13.394  1.00 60.32    C
ATOM     65  CG   GLN A 544     -16.153  32.175  12.981  1.00 62.61    C
ATOM     66  CD   GLN A 544     -16.910  31.522  14.147  1.00 65.09    C
ATOM     67  OE1  GLN A 544     -16.350  31.294  15.225  1.00 66.46    O
ATOM     68  NE2  GLN A 544     -18.187  31.216  13.926  1.00 66.08    N
ATOM     69  C    GLN A 544     -13.502  34.352  14.907  1.00 58.01    C
ATOM     70  O    GLN A 544     -12.554  34.510  14.135  1.00 58.45    O
ATOM     71  N    VAL A 545     -13.413  34.556  16.218  1.00 55.84    N
ATOM     72  CA   VAL A 545     -12.211  35.100  16.851  1.00 52.69    C
ATOM     73  CB   VAL A 545     -12.345  36.640  17.133  1.00 52.82    C
ATOM     74  CG1  VAL A 545     -12.541  37.416  15.841  1.00 51.59    C
ATOM     75  CG2  VAL A 545     -13.480  36.953  18.113  1.00 52.34    C
ATOM     76  C    VAL A 545     -11.999  34.323  18.134  1.00 50.92    C
ATOM     77  O    VAL A 545     -12.797  33.433  18.464  1.00 51.24    O
ATOM     78  N    TYR A 546     -10.937  34.640  18.863  1.00 48.60    N
ATOM     79  CA   TYR A 546     -10.733  34.014  20.154  1.00 46.13    C
ATOM     80  CB   TYR A 546      -9.312  33.450  20.290  1.00 47.88    C
ATOM     81  CG   TYR A 546      -8.956  32.491  19.164  1.00 49.86    C
ATOM     82  CD1  TYR A 546      -8.490  32.972  17.938  1.00 51.70    C
ATOM     83  CE1  TYR A 546      -8.168  32.104  16.888  1.00 53.30    C
ATOM     84  CZ   TYR A 546      -8.319  30.738  17.054  1.00 52.64    C
ATOM     85  OH   TYR A 546      -8.008  29.899  15.993  1.00 53.81    O
ATOM     86  CE2  TYR A 546      -8.792  30.226  18.263  1.00 53.05    C
ATOM     87  CD2  TYR A 546      -9.111  31.109  19.314  1.00 51.40    C
ATOM     88  C    TYR A 546     -11.086  34.982  21.275  1.00 43.74    C
ATOM     89  O    TYR A 546     -10.631  36.122  21.293  1.00 42.55    O
ATOM     90  N    TYR A 547     -11.932  34.515  22.188  1.00 40.90    N
ATOM     91  CA   TYR A 547     -12.277  35.261  23.370  1.00 38.59    C
ATOM     92  CB   TYR A 547     -13.662  34.865  23.886  1.00 37.62    C
ATOM     93  CG   TYR A 547     -14.186  35.757  25.008  1.00 36.43    C
ATOM     94  CD1  TYR A 547     -14.005  37.146  24.975  1.00 34.21    C
ATOM     95  CE1  TYR A 547     -14.492  37.967  25.995  1.00 34.09    C
ATOM     96  CZ   TYR A 547     -15.193  37.403  27.051  1.00 35.79    C
ATOM     97  OH   TYR A 547     -15.694  38.206  28.053  1.00 35.32    O
ATOM     98  CE2  TYR A 547     -15.393  36.031  27.105  1.00 36.64    C
ATOM     99  CD2  TYR A 547     -14.890  35.213  26.082  1.00 36.20    C
ATOM    100  C    TYR A 547     -11.238  34.940  24.424  1.00 37.32    C
ATOM    101  O    TYR A 547     -11.094  33.789  24.832  1.00 36.99    O
ATOM    102  N    LEU A 548     -10.521  35.971  24.850  1.00 36.00    N
ATOM    103  CA   LEU A 548      -9.458  35.829  25.833  1.00 34.83    C
ATOM    104  CB   LEU A 548      -8.346  36.850  25.545  1.00 34.37    C
ATOM    105  CG   LEU A 548      -7.722  36.828  24.142  1.00 34.41    C
ATOM    106  CD1  LEU A 548      -6.819  38.038  23.877  1.00 33.95    C
ATOM    107  CD2  LEU A 548      -6.964  35.538  23.919  1.00 33.02    C
ATOM    108  C    LEU A 548     -10.004  36.002  27.247  1.00 34.38    C
ATOM    109  O    LEU A 548      -9.322  35.714  28.221  1.00 35.07    O
ATOM    110  N    GLY A 549     -11.229  36.502  27.360  1.00 33.75    N
ATOM    111  CA   GLY A 549     -11.873  36.654  28.655  1.00 32.42    C
ATOM    112  C    GLY A 549     -12.061  38.111  29.020  1.00 32.53    C
```

FIG. 1C

```
ATOM    113  O    GLY A 549     -11.938  39.012  28.174  1.00 31.90   O
ATOM    114  N    ASN A 550     -12.373  38.340  30.289  1.00 32.21   N
ATOM    115  CA   ASN A 550     -12.596  39.679  30.781  1.00 32.92   C
ATOM    116  CB   ASN A 550     -14.086  40.035  30.730  1.00 32.69   C
ATOM    117  CG   ASN A 550     -14.939  39.163  31.649  1.00 34.88   C
ATOM    118  OD1  ASN A 550     -14.921  39.337  32.867  1.00 35.96   O
ATOM    119  ND2  ASN A 550     -15.692  38.218  31.059  1.00 35.37   N
ATOM    120  C    ASN A 550     -11.985  39.851  32.163  1.00 33.22   C
ATOM    121  O    ASN A 550     -11.855  38.880  32.915  1.00 33.86   O
ATOM    122  N    VAL A 551     -11.568  41.076  32.462  1.00 33.02   N
ATOM    123  CA   VAL A 551     -10.913  41.418  33.721  1.00 33.38   C
ATOM    124  CB   VAL A 551      -9.348  41.449  33.619  1.00 33.75   C
ATOM    125  CG1  VAL A 551      -8.761  40.060  33.230  1.00 35.89   C
ATOM    126  CG2  VAL A 551      -8.845  42.541  32.657  1.00 33.38   C
ATOM    127  C    VAL A 551     -11.446  42.781  34.170  1.00 33.19   C
ATOM    128  O    VAL A 551     -11.835  43.604  33.327  1.00 31.95   O
ATOM    129  N    PRO A 552     -11.518  43.012  35.494  1.00 33.33   N
ATOM    130  CA   PRO A 552     -11.874  44.362  35.931  1.00 33.21   C
ATOM    131  CB   PRO A 552     -11.999  44.230  37.461  1.00 33.11   C
ATOM    132  CG   PRO A 552     -11.237  43.038  37.815  1.00 34.47   C
ATOM    133  CD   PRO A 552     -11.302  42.100  36.635  1.00 33.83   C
ATOM    134  C    PRO A 552     -10.760  45.365  35.583  1.00 32.60   C
ATOM    135  O    PRO A 552      -9.586  45.014  35.573  1.00 32.37   O
ATOM    136  N    VAL A 553     -11.137  46.600  35.300  1.00 32.41   N
ATOM    137  CA   VAL A 553     -10.144  47.666  35.065  1.00 31.24   C
ATOM    138  CB   VAL A 553      -9.955  47.980  33.552  1.00 31.18   C
ATOM    139  CG1  VAL A 553      -9.215  46.807  32.821  1.00 27.32   C
ATOM    140  CG2  VAL A 553     -11.296  48.315  32.889  1.00 29.33   C
ATOM    141  C    VAL A 553     -10.599  48.896  35.835  1.00 31.97   C
ATOM    142  O    VAL A 553     -11.770  48.986  36.227  1.00 30.80   O
ATOM    143  N    ALA A 554      -9.680  49.835  36.036  1.00 32.25   N
ATOM    144  CA   ALA A 554      -9.890  50.979  36.944  1.00 33.13   C
ATOM    145  CB   ALA A 554      -8.541  51.451  37.513  1.00 33.05   C
ATOM    146  C    ALA A 554     -10.619  52.150  36.343  1.00 33.54   C
ATOM    147  O    ALA A 554     -11.228  52.942  37.079  1.00 34.15   O
ATOM    148  N    LYS A 555     -10.579  52.262  35.014  1.00 33.28   N
ATOM    149  CA   LYS A 555     -11.049  53.457  34.325  1.00 33.90   C
ATOM    150  CB   LYS A 555      -9.833  54.299  33.837  1.00 33.74   C
ATOM    151  CG   LYS A 555      -8.883  54.783  34.945  1.00 37.51   C
ATOM    152  CD   LYS A 555      -7.751  55.740  34.419  1.00 38.10   C
ATOM    153  CE   LYS A 555      -6.576  55.012  33.738  1.00 45.23   C
ATOM    154  NZ   LYS A 555      -5.452  55.888  33.139  1.00 44.08   N
ATOM    155  C    LYS A 555     -11.937  53.070  33.123  1.00 32.46   C
ATOM    156  O    LYS A 555     -11.773  51.994  32.555  1.00 31.18   O
ATOM    157  N    PRO A 556     -12.884  53.952  32.738  1.00 31.86   N
ATOM    158  CA   PRO A 556     -13.762  53.663  31.600  1.00 31.40   C
ATOM    159  CB   PRO A 556     -14.836  54.757  31.702  1.00 31.37   C
ATOM    160  CG   PRO A 556     -14.129  55.902  32.345  1.00 31.96   C
ATOM    161  CD   PRO A 556     -13.195  55.264  33.351  1.00 31.73   C
ATOM    162  C    PRO A 556     -13.083  53.751  30.222  1.00 30.75   C
ATOM    163  O    PRO A 556     -13.616  53.212  29.254  1.00 29.53   O
ATOM    164  N    VAL A 557     -11.939  54.442  30.138  1.00 31.08   N
ATOM    165  CA   VAL A 557     -11.273  54.716  28.838  1.00 31.01   C
ATOM    166  CB   VAL A 557     -11.667  56.119  28.236  1.00 30.88   C
ATOM    167  CG1  VAL A 557     -13.201  56.293  28.081  1.00 31.76   C
ATOM    168  CG2  VAL A 557     -11.083  57.251  29.069  1.00 32.46   C
```

FIG. 1D

```
ATOM    169  C   VAL A 557      -9.732  54.624  28.913  1.00 30.42      C
ATOM    170  O   VAL A 557      -9.146  54.714  29.984  1.00 30.81      O
ATOM    171  N   GLY A 558      -9.101  54.428  27.768  1.00 30.36      N
ATOM    172  CA  GLY A 558      -7.640  54.630  27.623  1.00 30.44      C
ATOM    173  C   GLY A 558      -6.973  53.462  26.935  1.00 29.96      C
ATOM    174  O   GLY A 558      -7.217  52.319  27.319  1.00 29.15      O
ATOM    175  N   VAL A 559      -6.146  53.720  25.911  1.00 29.92      N
ATOM    176  CA  VAL A 559      -5.388  52.625  25.291  1.00 29.58      C
ATOM    177  CB  VAL A 559      -4.680  52.997  23.924  1.00 30.28      C
ATOM    178  CG1 VAL A 559      -5.698  53.220  22.827  1.00 31.83      C
ATOM    179  CG2 VAL A 559      -3.781  54.207  24.062  1.00 31.64      C
ATOM    180  C   VAL A 559      -4.396  51.980  26.283  1.00 28.48      C
ATOM    181  O   VAL A 559      -4.109  50.787  26.201  1.00 28.51      O
ATOM    182  N   ASP A 560      -3.877  52.768  27.210  1.00 28.47      N
ATOM    183  CA  ASP A 560      -3.025  52.220  28.270  1.00 29.12      C
ATOM    184  CB  ASP A 560      -2.499  53.329  29.173  1.00 29.35      C
ATOM    185  CG  ASP A 560      -3.608  54.097  29.861  1.00 34.74      C
ATOM    186  OD1 ASP A 560      -4.601  54.440  29.187  1.00 40.72      O
ATOM    187  OD2 ASP A 560      -3.483  54.379  31.079  1.00 37.91      O
ATOM    188  C   ASP A 560      -3.760  51.196  29.145  1.00 28.18      C
ATOM    189  O   ASP A 560      -3.168  50.211  29.559  1.00 27.06      O
ATOM    190  N   VAL A 561      -5.044  51.466  29.427  1.00 27.60      N
ATOM    191  CA  VAL A 561      -5.876  50.574  30.240  1.00 27.32      C
ATOM    192  CB  VAL A 561      -7.276  51.214  30.557  1.00 26.96      C
ATOM    193  CG1 VAL A 561      -8.179  50.234  31.288  1.00 26.68      C
ATOM    194  CG2 VAL A 561      -7.085  52.454  31.416  1.00 27.04      C
ATOM    195  C   VAL A 561      -6.063  49.250  29.527  1.00 26.46      C
ATOM    196  O   VAL A 561      -5.855  48.204  30.115  1.00 26.50      O
ATOM    197  N   ILE A 562      -6.438  49.295  28.253  1.00 26.19      N
ATOM    198  CA  ILE A 562      -6.693  48.069  27.523  1.00 25.75      C
ATOM    199  CB  ILE A 562      -7.548  48.268  26.219  1.00 26.96      C
ATOM    200  CG1 ILE A 562      -6.791  49.068  25.143  1.00 28.22      C
ATOM    201  CD1 ILE A 562      -6.240  48.172  23.990  1.00 31.13      C
ATOM    202  CG2 ILE A 562      -8.974  48.868  26.533  1.00 24.67      C
ATOM    203  C   ILE A 562      -5.421  47.292  27.203  1.00 25.16      C
ATOM    204  O   ILE A 562      -5.442  46.073  27.213  1.00 24.80      O
ATOM    205  N   ASN A 563      -4.314  47.983  26.953  1.00 25.25      N
ATOM    206  CA  ASN A 563      -3.044  47.268  26.722  1.00 25.43      C
ATOM    207  CB  ASN A 563      -2.000  48.175  26.020  1.00 25.29      C
ATOM    208  CG  ASN A 563      -2.313  48.362  24.536  1.00 22.84      C
ATOM    209  OD1 ASN A 563      -2.290  47.414  23.788  1.00 25.62      O
ATOM    210  ND2 ASN A 563      -2.651  49.578  24.130  1.00 23.16      N
ATOM    211  C   ASN A 563      -2.486  46.643  27.982  1.00 25.57      C
ATOM    212  O   ASN A 563      -1.877  45.602  27.905  1.00 26.12      O
ATOM    213  N   GLY A 564      -2.725  47.271  29.141  1.00 26.44      N
ATOM    214  CA  GLY A 564      -2.379  46.663  30.422  1.00 27.37      C
ATOM    215  C   GLY A 564      -3.165  45.387  30.651  1.00 27.80      C
ATOM    216  O   GLY A 564      -2.587  44.371  31.041  1.00 27.67      O
ATOM    217  N   ALA A 565      -4.480  45.438  30.364  1.00 27.95      N
ATOM    218  CA  ALA A 565      -5.376  44.275  30.473  1.00 27.82      C
ATOM    219  CB  ALA A 565      -6.831  44.701  30.188  1.00 28.29      C
ATOM    220  C   ALA A 565      -4.954  43.132  29.533  1.00 28.35      C
ATOM    221  O   ALA A 565      -4.874  41.976  29.963  1.00 28.25      O
ATOM    222  N   LEU A 566      -4.657  43.461  28.265  1.00 27.76      N
ATOM    223  CA  LEU A 566      -4.190  42.477  27.269  1.00 28.20      C
ATOM    224  CB  LEU A 566      -3.997  43.143  25.896  1.00 28.35      C
```

FIG. 1E

| | | | | | | | | | |
|---|---|---|---|---|---|---|---|---|---|
| ATOM | 225 | CG  | LEU | A | 566 | -5.290 | 43.543 | 25.175 | 1.00 28.00 C |
| ATOM | 226 | CD1 | LEU | A | 566 | -5.041 | 44.502 | 24.049 | 1.00 24.74 C |
| ATOM | 227 | CD2 | LEU | A | 566 | -5.978 | 42.280 | 24.698 | 1.00 27.34 C |
| ATOM | 228 | C   | LEU | A | 566 | -2.888 | 41.788 | 27.666 | 1.00 28.41 C |
| ATOM | 229 | O   | LEU | A | 566 | -2.798 | 40.568 | 27.646 | 1.00 28.71 O |
| ATOM | 230 | N   | GLU | A | 567 | -1.874 | 42.573 | 28.018 | 1.00 29.43 N |
| ATOM | 231 | CA  | GLU | A | 567 | -0.606 | 41.989 | 28.492 | 1.00 29.86 C |
| ATOM | 232 | CB  | GLU | A | 567 | 0.414  | 43.083 | 28.810 | 1.00 29.89 C |
| ATOM | 233 | CG  | GLU | A | 567 | 0.949  | 43.781 | 27.547 | 1.00 28.82 C |
| ATOM | 234 | CD  | GLU | A | 567 | 1.792  | 44.987 | 27.815 | 1.00 28.15 C |
| ATOM | 235 | OE1 | GLU | A | 567 | 2.005  | 45.319 | 28.978 | 1.00 28.26 O |
| ATOM | 236 | OE2 | GLU | A | 567 | 2.275  | 45.627 | 26.855 | 1.00 27.67 O |
| ATOM | 237 | C   | GLU | A | 567 | -0.820 | 41.037 | 29.687 | 1.00 30.47 C |
| ATOM | 238 | O   | GLU | A | 567 | -0.258 | 39.958 | 29.714 | 1.00 30.87 O |
| ATOM | 239 | N   | SER | A | 568 | -1.645 | 41.432 | 30.651 | 1.00 30.88 N |
| ATOM | 240 | CA  | SER | A | 568 | -1.936 | 40.585 | 31.791 | 1.00 31.87 C |
| ATOM | 241 | CB  | SER | A | 568 | -2.808 | 41.318 | 32.807 | 1.00 32.24 C |
| ATOM | 242 | OG  | SER | A | 568 | -1.998 | 42.256 | 33.500 | 1.00 35.93 O |
| ATOM | 243 | C   | SER | A | 568 | -2.558 | 39.250 | 31.415 | 1.00 32.20 C |
| ATOM | 244 | O   | SER | A | 568 | -2.039 | 38.207 | 31.834 | 1.00 32.35 O |
| ATOM | 245 | N   | VAL | A | 569 | -3.643 | 39.269 | 30.627 | 1.00 32.19 N |
| ATOM | 246 | CA  | VAL | A | 569 | -4.297 | 38.029 | 30.204 | 1.00 32.56 C |
| ATOM | 247 | CB  | VAL | A | 569 | -5.734 | 38.270 | 29.605 | 1.00 32.72 C |
| ATOM | 248 | CG1 | VAL | A | 569 | -5.689 | 38.814 | 28.183 | 1.00 31.15 C |
| ATOM | 249 | CG2 | VAL | A | 569 | -6.506 | 36.990 | 29.626 | 1.00 33.77 C |
| ATOM | 250 | C   | VAL | A | 569 | -3.421 | 37.145 | 29.278 | 1.00 32.86 C |
| ATOM | 251 | O   | VAL | A | 569 | -3.410 | 35.910 | 29.398 | 1.00 33.47 O |
| ATOM | 252 | N   | LEU | A | 570 | -2.676 | 37.766 | 28.373 | 1.00 32.79 N |
| ATOM | 253 | CA  | LEU | A | 570 | -1.791 | 37.001 | 27.485 | 1.00 33.59 C |
| ATOM | 254 | CB  | LEU | A | 570 | -1.205 | 37.891 | 26.373 | 1.00 33.50 C |
| ATOM | 255 | CG  | LEU | A | 570 | -2.211 | 38.436 | 25.345 | 1.00 33.90 C |
| ATOM | 256 | CD1 | LEU | A | 570 | -1.564 | 39.499 | 24.484 | 1.00 35.01 C |
| ATOM | 257 | CD2 | LEU | A | 570 | -2.787 | 37.342 | 24.452 | 1.00 34.24 C |
| ATOM | 258 | C   | LEU | A | 570 | -0.667 | 36.311 | 28.252 | 1.00 34.19 C |
| ATOM | 259 | O   | LEU | A | 570 | -0.241 | 35.240 | 27.874 | 1.00 34.18 O |
| ATOM | 260 | N   | SER | A | 571 | -0.205 | 36.928 | 29.332 | 1.00 35.62 N |
| ATOM | 261 | CA  | SER | A | 571 | 0.879  | 36.371 | 30.134 | 1.00 38.21 C |
| ATOM | 262 | CB  | SER | A | 571 | 1.487  | 37.440 | 31.025 | 1.00 37.06 C |
| ATOM | 263 | OG  | SER | A | 571 | 0.619  | 37.749 | 32.092 | 1.00 38.21 O |
| ATOM | 264 | C   | SER | A | 571 | 0.440  | 35.198 | 30.988 | 1.00 40.06 C |
| ATOM | 265 | O   | SER | A | 571 | 1.277  | 34.431 | 31.432 | 1.00 41.25 O |
| ATOM | 266 | N   | SER | A | 572 | -0.868 | 35.054 | 31.203 | 1.00 42.95 N |
| ATOM | 267 | CA  | SER | A | 572 | -1.418 | 34.044 | 32.117 | 1.00 45.41 C |
| ATOM | 268 | CB  | SER | A | 572 | -2.254 | 34.721 | 33.218 | 1.00 45.21 C |
| ATOM | 269 | OG  | SER | A | 572 | -3.389 | 35.413 | 32.684 | 1.00 46.75 O |
| ATOM | 270 | C   | SER | A | 572 | -2.251 | 32.975 | 31.407 | 1.00 47.05 C |
| ATOM | 271 | O   | SER | A | 572 | -3.034 | 32.269 | 32.034 | 1.00 47.61 O |
| ATOM | 272 | N   | SER | A | 573 | -2.078 | 32.860 | 30.097 | 1.00 48.97 N |
| ATOM | 273 | CA  | SER | A | 573 | -2.841 | 31.921 | 29.299 | 1.00 51.00 C |
| ATOM | 274 | CB  | SER | A | 573 | -4.154 | 32.557 | 28.810 | 1.00 51.15 C |
| ATOM | 275 | OG  | SER | A | 573 | -3.925 | 33.757 | 28.064 | 1.00 52.55 O |
| ATOM | 276 | C   | SER | A | 573 | -1.977 | 31.497 | 28.123 | 1.00 52.25 C |
| ATOM | 277 | O   | SER | A | 573 | -0.988 | 32.164 | 27.805 | 1.00 52.61 O |
| ATOM | 278 | N   | SER | A | 574 | -2.319 | 30.369 | 27.510 | 1.00 53.46 N |
| ATOM | 279 | CA  | SER | A | 574 | -1.657 | 29.924 | 26.286 | 1.00 54.91 C |
| ATOM | 280 | CB  | SER | A | 574 | -0.891 | 28.611 | 26.509 | 1.00 55.04 C |

FIG. 1F

| ATOM | 281 | OG  | SER A 574 | -1.733  | 27.599 | 27.046 | 1.00 | 56.12 | O |
|------|-----|-----|-----------|---------|--------|--------|------|-------|---|
| ATOM | 282 | C   | SER A 574 | -2.707  | 29.767 | 25.202 | 1.00 | 55.46 | C |
| ATOM | 283 | O   | SER A 574 | -3.889  | 29.620 | 25.500 | 1.00 | 55.83 | O |
| ATOM | 284 | N   | ARG A 575 | -2.279  | 29.801 | 23.949 | 1.00 | 56.28 | N |
| ATOM | 285 | CA  | ARG A 575 | -3.199  | 29.771 | 22.818 | 1.00 | 56.90 | C |
| ATOM | 286 | CB  | ARG A 575 | -2.428  | 29.787 | 21.504 | 1.00 | 56.83 | C |
| ATOM | 287 | CG  | ARG A 575 | -1.566  | 31.006 | 21.337 | 1.00 | 55.25 | C |
| ATOM | 288 | CD  | ARG A 575 | -1.343  | 31.314 | 19.880 | 1.00 | 53.80 | C |
| ATOM | 289 | NE  | ARG A 575 | -0.534  | 32.521 | 19.726 | 1.00 | 53.41 | N |
| ATOM | 290 | CZ  | ARG A 575 | -0.489  | 33.266 | 18.626 | 1.00 | 53.10 | C |
| ATOM | 291 | NH1 | ARG A 575 | -1.221  | 32.932 | 17.562 | 1.00 | 53.47 | N |
| ATOM | 292 | NH2 | ARG A 575 | 0.282   | 34.351 | 18.592 | 1.00 | 51.71 | N |
| ATOM | 293 | C   | ARG A 575 | -4.207  | 28.623 | 22.825 | 1.00 | 58.09 | C |
| ATOM | 294 | O   | ARG A 575 | -5.309  | 28.765 | 22.296 | 1.00 | 58.19 | O |
| ATOM | 295 | N   | GLU A 576 | -3.831  | 27.499 | 23.426 | 1.00 | 59.31 | N |
| ATOM | 296 | CA  | GLU A 576 | -4.710  | 26.322 | 23.530 | 1.00 | 60.92 | C |
| ATOM | 297 | CB  | GLU A 576 | -3.887  | 25.072 | 23.849 | 1.00 | 61.17 | C |
| ATOM | 298 | CG  | GLU A 576 | -2.631  | 24.931 | 22.978 | 1.00 | 63.14 | C |
| ATOM | 299 | CD  | GLU A 576 | -1.833  | 23.672 | 23.290 | 1.00 | 64.38 | C |
| ATOM | 300 | OE1 | GLU A 576 | -1.436  | 23.478 | 24.478 | 1.00 | 68.27 | O |
| ATOM | 301 | OE2 | GLU A 576 | -1.596  | 22.881 | 22.335 | 1.00 | 68.85 | O |
| ATOM | 302 | C   | GLU A 576 | -5.827  | 26.516 | 24.570 | 1.00 | 59.98 | C |
| ATOM | 303 | O   | GLU A 576 | -6.886  | 25.887 | 24.490 | 1.00 | 60.20 | O |
| ATOM | 304 | N   | GLN A 577 | -5.583  | 27.400 | 25.534 | 1.00 | 58.97 | N |
| ATOM | 305 | CA  | GLN A 577 | -6.605  | 27.809 | 26.497 | 1.00 | 58.09 | C |
| ATOM | 306 | CB  | GLN A 577 | -5.969  | 28.503 | 27.706 | 1.00 | 58.34 | C |
| ATOM | 307 | CG  | GLN A 577 | -4.869  | 27.720 | 28.411 | 1.00 | 59.62 | C |
| ATOM | 308 | CD  | GLN A 577 | -4.289  | 28.482 | 29.597 | 1.00 | 60.30 | C |
| ATOM | 309 | OE1 | GLN A 577 | -4.947  | 29.358 | 30.176 | 1.00 | 63.29 | O |
| ATOM | 310 | NE2 | GLN A 577 | -3.054  | 28.146 | 29.972 | 1.00 | 62.87 | N |
| ATOM | 311 | C   | GLN A 577 | -7.650  | 28.749 | 25.896 | 1.00 | 56.05 | C |
| ATOM | 312 | O   | GLN A 577 | -8.738  | 28.878 | 26.453 | 1.00 | 56.02 | O |
| ATOM | 313 | N   | TRP A 578 | -7.325  | 29.402 | 24.777 | 1.00 | 53.90 | N |
| ATOM | 314 | CA  | TRP A 578 | -8.209  | 30.417 | 24.195 | 1.00 | 52.07 | C |
| ATOM | 315 | CB  | TRP A 578 | -7.540  | 31.205 | 23.058 | 1.00 | 50.13 | C |
| ATOM | 316 | CG  | TRP A 578 | -6.295  | 31.982 | 23.438 | 1.00 | 48.27 | C |
| ATOM | 317 | CD1 | TRP A 578 | -5.798  | 32.200 | 24.703 | 1.00 | 45.19 | C |
| ATOM | 318 | NE1 | TRP A 578 | -4.652  | 32.966 | 24.633 | 1.00 | 45.04 | N |
| ATOM | 319 | CE2 | TRP A 578 | -4.393  | 33.273 | 23.323 | 1.00 | 44.69 | C |
| ATOM | 320 | CD2 | TRP A 578 | -5.416  | 32.682 | 22.538 | 1.00 | 46.37 | C |
| ATOM | 321 | CE3 | TRP A 578 | -5.383  | 32.852 | 21.147 | 1.00 | 45.53 | C |
| ATOM | 322 | CZ3 | TRP A 578 | -4.341  | 33.604 | 20.589 | 1.00 | 45.72 | C |
| ATOM | 323 | CH2 | TRP A 578 | -3.347  | 34.180 | 21.401 | 1.00 | 45.66 | C |
| ATOM | 324 | CZ2 | TRP A 578 | -3.355  | 34.020 | 22.763 | 1.00 | 45.94 | C |
| ATOM | 325 | C   | TRP A 578 | -9.519  | 29.820 | 23.692 | 1.00 | 52.43 | C |
| ATOM | 326 | O   | TRP A 578 | -9.542  | 28.717 | 23.120 | 1.00 | 52.95 | O |
| ATOM | 327 | N   | THR A 579 | -10.602 | 30.569 | 23.893 | 1.00 | 52.10 | N |
| ATOM | 328 | CA  | THR A 579 | -11.946 | 30.099 | 23.579 | 1.00 | 51.62 | C |
| ATOM | 329 | CB  | THR A 579 | -12.947 | 30.545 | 24.654 | 1.00 | 51.82 | C |
| ATOM | 330 | OG1 | THR A 579 | -12.522 | 30.036 | 25.925 | 1.00 | 51.44 | O |
| ATOM | 331 | CG2 | THR A 579 | -14.360 | 30.041 | 24.345 | 1.00 | 51.88 | C |
| ATOM | 332 | C   | THR A 579 | -12.361 | 30.588 | 22.199 | 1.00 | 51.51 | C |
| ATOM | 333 | O   | THR A 579 | -12.531 | 31.788 | 21.995 | 1.00 | 50.57 | O |
| ATOM | 334 | N   | PRO A 580 | -12.501 | 29.649 | 21.230 | 1.00 | 51.75 | N |
| ATOM | 335 | CA  | PRO A 580 | -12.954 | 30.077 | 19.917 | 1.00 | 51.76 | C |
| ATOM | 336 | CB  | PRO A 580 | -12.851 | 28.804 | 19.068 | 1.00 | 51.74 | C |

FIG. 1G

| | | | | | | | | | | |
|---|---|---|---|---|---|---|---|---|---|---|
| ATOM | 337 | CG | PRO | A | 580 | -12.930 | 27.687 | 20.046 | 1.00 52.07 | C |
| ATOM | 338 | CD | PRO | A | 580 | -12.256 | 28.193 | 21.290 | 1.00 51.66 | C |
| ATOM | 339 | C | PRO | A | 580 | -14.396 | 30.531 | 20.055 | 1.00 52.01 | C |
| ATOM | 340 | O | PRO | A | 580 | -15.171 | 29.946 | 20.828 | 1.00 52.00 | O |
| ATOM | 341 | N | SER | A | 581 | -14.750 | 31.574 | 19.327 | 1.00 52.08 | N |
| ATOM | 342 | CA | SER | A | 581 | -16.014 | 32.223 | 19.569 | 1.00 52.60 | C |
| ATOM | 343 | CB | SER | A | 581 | -15.939 | 33.059 | 20.865 | 1.00 52.42 | C |
| ATOM | 344 | OG | SER | A | 581 | -15.080 | 34.177 | 20.706 | 1.00 51.23 | O |
| ATOM | 345 | C | SER | A | 581 | -16.356 | 33.121 | 18.402 | 1.00 53.11 | C |
| ATOM | 346 | O | SER | A | 581 | -15.506 | 33.404 | 17.549 | 1.00 53.60 | O |
| ATOM | 347 | N | HIS | A | 582 | -17.598 | 33.594 | 18.386 | 1.00 53.35 | N |
| ATOM | 348 | CA | HIS | A | 582 | -18.001 | 34.629 | 17.436 | 1.00 53.51 | C |
| ATOM | 349 | CB | HIS | A | 582 | -18.851 | 34.029 | 16.296 | 1.00 54.23 | C |
| ATOM | 350 | CG | HIS | A | 582 | -19.712 | 32.888 | 16.730 | 1.00 57.52 | C |
| ATOM | 351 | ND1 | HIS | A | 582 | -21.078 | 32.997 | 16.871 | 1.00 61.13 | N |
| ATOM | 352 | CE1 | HIS | A | 582 | -21.570 | 31.842 | 17.287 | 1.00 61.64 | C |
| ATOM | 353 | NE2 | HIS | A | 582 | -20.571 | 30.988 | 17.427 | 1.00 61.13 | N |
| ATOM | 354 | CD2 | HIS | A | 582 | -19.398 | 31.618 | 17.083 | 1.00 60.70 | C |
| ATOM | 355 | C | HIS | A | 582 | -18.709 | 35.785 | 18.149 | 1.00 52.31 | C |
| ATOM | 356 | O | HIS | A | 582 | -19.362 | 35.587 | 19.177 | 1.00 52.31 | O |
| ATOM | 357 | N | VAL | A | 583 | -18.541 | 36.990 | 17.616 | 1.00 51.10 | N |
| ATOM | 358 | CA | VAL | A | 583 | -19.176 | 38.155 | 18.192 | 1.00 49.97 | C |
| ATOM | 359 | CB | VAL | A | 583 | -18.191 | 39.331 | 18.433 | 1.00 49.97 | C |
| ATOM | 360 | CG1 | VAL | A | 583 | -18.935 | 40.581 | 18.924 | 1.00 48.62 | C |
| ATOM | 361 | CG2 | VAL | A | 583 | -17.096 | 38.929 | 19.416 | 1.00 49.14 | C |
| ATOM | 362 | C | VAL | A | 583 | -20.299 | 38.603 | 17.280 | 1.00 49.39 | C |
| ATOM | 363 | O | VAL | A | 583 | -20.072 | 39.015 | 16.134 | 1.00 49.15 | O |
| ATOM | 364 | N | SER | A | 584 | -21.512 | 38.527 | 17.806 | 1.00 48.05 | N |
| ATOM | 365 | CA | SER | A | 584 | -22.650 | 39.048 | 17.092 | 1.00 47.33 | C |
| ATOM | 366 | CB | SER | A | 584 | -23.909 | 38.250 | 17.414 | 1.00 47.45 | C |
| ATOM | 367 | OG | SER | A | 584 | -24.990 | 38.787 | 16.689 | 1.00 48.48 | O |
| ATOM | 368 | C | SER | A | 584 | -22.831 | 40.513 | 17.441 | 1.00 46.53 | C |
| ATOM | 369 | O | SER | A | 584 | -22.950 | 40.886 | 18.607 | 1.00 45.72 | O |
| ATOM | 370 | N | VAL | A | 585 | -22.831 | 41.342 | 16.408 | 1.00 46.16 | N |
| ATOM | 371 | CA | VAL | A | 585 | -22.943 | 42.768 | 16.569 | 1.00 45.65 | C |
| ATOM | 372 | CB | VAL | A | 585 | -21.881 | 43.523 | 15.698 | 1.00 45.79 | C |
| ATOM | 373 | CG1 | VAL | A | 585 | -22.038 | 45.040 | 15.813 | 1.00 44.34 | C |
| ATOM | 374 | CG2 | VAL | A | 585 | -20.455 | 43.099 | 16.075 | 1.00 44.74 | C |
| ATOM | 375 | C | VAL | A | 585 | -24.371 | 43.117 | 16.168 | 1.00 46.22 | C |
| ATOM | 376 | O | VAL | A | 585 | -24.739 | 42.993 | 15.001 | 1.00 46.27 | O |
| ATOM | 377 | N | ALA | A | 586 | -25.187 | 43.497 | 17.149 | 1.00 46.23 | N |
| ATOM | 378 | CA | ALA | A | 586 | -26.552 | 43.934 | 16.886 | 1.00 45.93 | C |
| ATOM | 379 | CB | ALA | A | 586 | -27.560 | 43.119 | 17.703 | 1.00 46.27 | C |
| ATOM | 380 | C | ALA | A | 586 | -26.650 | 45.427 | 17.191 | 1.00 45.43 | C |
| ATOM | 381 | O | ALA | A | 586 | -25.688 | 46.012 | 17.724 | 1.00 45.96 | O |
| ATOM | 382 | N | PRO | A | 587 | -27.760 | 46.071 | 16.788 | 1.00 44.77 | N |
| ATOM | 383 | CA | PRO | A | 587 | -27.968 | 47.505 | 17.081 | 1.00 44.26 | C |
| ATOM | 384 | CB | PRO | A | 587 | -29.458 | 47.748 | 16.750 | 1.00 43.98 | C |
| ATOM | 385 | CG | PRO | A | 587 | -30.011 | 46.429 | 16.222 | 1.00 45.44 | C |
| ATOM | 386 | CD | PRO | A | 587 | -28.834 | 45.523 | 15.931 | 1.00 45.15 | C |
| ATOM | 387 | C | PRO | A | 587 | -27.699 | 47.947 | 18.531 | 1.00 43.12 | C |
| ATOM | 388 | O | PRO | A | 587 | -27.115 | 49.017 | 18.757 | 1.00 42.57 | O |
| ATOM | 389 | N | ALA | A | 588 | -28.155 | 47.147 | 19.491 | 1.00 41.59 | N |
| ATOM | 390 | CA | ALA | A | 588 | -28.185 | 47.588 | 20.876 | 1.00 40.49 | C |
| ATOM | 391 | CB | ALA | A | 588 | -29.615 | 47.507 | 21.414 | 1.00 40.48 | C |
| ATOM | 392 | C | ALA | A | 588 | -27.238 | 46.790 | 21.760 | 1.00 39.35 | C |

FIG. 1H

```
ATOM    393  O    ALA A 588     -26.954  47.193  22.880  1.00 38.51      O
ATOM    394  N    THR A 589     -26.756  45.662  21.247  1.00 39.09      N
ATOM    395  CA   THR A 589     -25.957  44.729  22.043  1.00 39.56      C
ATOM    396  CB   THR A 589     -26.813  43.551  22.605  1.00 39.97      C
ATOM    397  OG1  THR A 589     -27.358  42.792  21.513  1.00 42.07      O
ATOM    398  CG2  THR A 589     -27.960  44.039  23.516  1.00 39.33      C
ATOM    399  C    THR A 589     -24.827  44.109  21.234  1.00 39.15      C
ATOM    400  O    THR A 589     -24.919  44.005  20.005  1.00 39.39      O
ATOM    401  N    LEU A 590     -23.764  43.706  21.935  1.00 38.62      N
ATOM    402  CA   LEU A 590     -22.786  42.756  21.411  1.00 38.04      C
ATOM    403  CB   LEU A 590     -21.332  43.234  21.608  1.00 37.39      C
ATOM    404  CG   LEU A 590     -20.940  44.697  21.366  1.00 38.35      C
ATOM    405  CD1  LEU A 590     -19.423  44.854  21.480  1.00 36.81      C
ATOM    406  CD2  LEU A 590     -21.443  45.250  20.022  1.00 38.12      C
ATOM    407  C    LEU A 590     -22.989  41.454  22.172  1.00 38.23      C
ATOM    408  O    LEU A 590     -23.087  41.456  23.410  1.00 37.61      O
ATOM    409  N    THR A 591     -23.047  40.352  21.438  1.00 38.38      N
ATOM    410  CA   THR A 591     -23.143  39.048  22.061  1.00 40.18      C
ATOM    411  CB   THR A 591     -24.488  38.336  21.722  1.00 40.11      C
ATOM    412  OG1  THR A 591     -25.573  39.241  21.980  1.00 40.14      O
ATOM    413  CG2  THR A 591     -24.676  37.090  22.578  1.00 39.56      C
ATOM    414  C    THR A 591     -21.945  38.207  21.643  1.00 41.23      C
ATOM    415  O    THR A 591     -21.635  38.105  20.459  1.00 41.38      O
ATOM    416  N    ILE A 592     -21.274  37.638  22.637  1.00 43.04      N
ATOM    417  CA   ILE A 592     -20.141  36.740  22.426  1.00 45.76      C
ATOM    418  CB   ILE A 592     -18.942  37.053  23.391  1.00 45.62      C
ATOM    419  CG1  ILE A 592     -18.692  38.575  23.504  1.00 44.87      C
ATOM    420  CD1  ILE A 592     -17.956  38.999  24.766  1.00 45.07      C
ATOM    421  CG2  ILE A 592     -17.701  36.303  22.925  1.00 44.82      C
ATOM    422  C    ILE A 592     -20.580  35.293  22.621  1.00 47.83      C
ATOM    423  O    ILE A 592     -21.066  34.922  23.684  1.00 47.79      O
ATOM    424  N    LEU A 593     -20.383  34.476  21.589  1.00 51.53      N
ATOM    425  CA   LEU A 593     -20.856  33.073  21.593  1.00 54.86      C
ATOM    426  CB   LEU A 593     -22.008  32.929  20.586  1.00 55.11      C
ATOM    427  CG   LEU A 593     -23.020  34.092  20.503  1.00 55.64      C
ATOM    428  CD1  LEU A 593     -23.151  34.666  19.089  1.00 55.17      C
ATOM    429  CD2  LEU A 593     -24.370  33.687  21.085  1.00 55.36      C
ATOM    430  C    LEU A 593     -19.737  32.070  21.252  1.00 56.64      C
ATOM    431  O    LEU A 593     -18.905  32.358  20.400  1.00 56.92      O
ATOM    432  N    HIS A 594     -19.734  30.909  21.911  1.00 59.64      N
ATOM    433  CA   HIS A 594     -18.795  29.790  21.618  1.00 62.47      C
ATOM    434  CB   HIS A 594     -19.119  28.604  22.518  1.00 62.47      C
ATOM    435  CG   HIS A 594     -17.915  27.943  23.120  1.00 64.47      C
ATOM    436  ND1  HIS A 594     -16.936  27.332  22.362  1.00 65.46      N
ATOM    437  CE1  HIS A 594     -16.012  26.829  23.165  1.00 65.84      C
ATOM    438  NE2  HIS A 594     -16.360  27.083  24.416  1.00 65.53      N
ATOM    439  CD2  HIS A 594     -17.549  27.773  24.416  1.00 65.61      C
ATOM    440  C    HIS A 594     -18.836  29.363  20.132  1.00 64.05      C
ATOM    441  O    HIS A 594     -19.915  29.400  19.513  1.00 64.16      O
ATOM    442  N    GLN A 595     -17.682  28.949  19.571  1.00 65.90      N
ATOM    443  CA   GLN A 595     -17.480  28.935  18.094  1.00 67.31      C
ATOM    444  CB   GLN A 595     -16.137  28.362  17.621  1.00 67.47      C
ATOM    445  CG   GLN A 595     -16.125  28.307  16.074  1.00 68.47      C
ATOM    446  CD   GLN A 595     -14.849  27.812  15.443  1.00 70.15      C
ATOM    447  OE1  GLN A 595     -14.213  26.874  15.931  1.00 70.63      O
ATOM    448  NE2  GLN A 595     -14.478  28.428  14.317  1.00 70.54      N
```

FIG. 1I

```
ATOM    449  C   GLN A 595     -18.582  28.378  17.201  1.00 68.11      C
ATOM    450  O   GLN A 595     -18.932  29.000  16.182  1.00 68.67      O
ATOM    451  N   GLN A 596     -19.103  27.195  17.515  1.00 68.88      N
ATOM    452  CA  GLN A 596     -20.258  26.763  16.735  1.00 69.47      C
ATOM    453  CB  GLN A 596     -19.854  26.059  15.383  1.00 69.89      C
ATOM    454  CG  GLN A 596     -19.567  24.522  15.458  1.00 71.70      C
ATOM    455  CD  GLN A 596     -20.287  23.862  14.237  1.00 74.38      C
ATOM    456  OE1 GLN A 596     -20.469  24.488  13.165  1.00 74.81      O
ATOM    457  NE2 GLN A 596     -20.718  22.594  14.406  1.00 75.27      N
ATOM    458  C   GLN A 596     -21.431  26.096  17.458  1.00 69.38      C
ATOM    459  O   GLN A 596     -22.525  25.945  16.873  1.00 69.59      O
ATOM    460  N   THR A 597     -21.212  25.750  18.733  1.00 69.13      N
ATOM    461  CA  THR A 597     -22.318  25.479  19.666  1.00 68.61      C
ATOM    462  CB  THR A 597     -21.818  25.010  21.060  1.00 68.71      C
ATOM    463  OG1 THR A 597     -21.072  26.063  21.694  1.00 69.68      O
ATOM    464  CG2 THR A 597     -20.940  23.780  20.940  1.00 68.40      C
ATOM    465  C   THR A 597     -23.185  26.746  19.824  1.00 68.03      C
ATOM    466  O   THR A 597     -24.392  26.667  20.093  1.00 68.22      O
ATOM    467  N   GLU A 598     -22.549  27.905  19.632  1.00 67.01      N
ATOM    468  CA  GLU A 598     -23.190  29.228  19.702  1.00 66.05      C
ATOM    469  CB  GLU A 598     -24.168  29.448  18.535  1.00 66.46      C
ATOM    470  CG  GLU A 598     -23.566  29.178  17.144  1.00 68.68      C
ATOM    471  CD  GLU A 598     -23.984  30.211  16.085  1.00 71.36      C
ATOM    472  OE1 GLU A 598     -25.018  30.885  16.283  1.00 72.82      O
ATOM    473  OE2 GLU A 598     -23.274  30.355  15.056  1.00 71.83      O
ATOM    474  C   GLU A 598     -23.831  29.559  21.065  1.00 64.83      C
ATOM    475  O   GLU A 598     -24.714  30.423  21.144  1.00 64.99      O
ATOM    476  N   ALA A 599     -23.377  28.869  22.119  1.00 63.01      N
ATOM    477  CA  ALA A 599     -23.690  29.198  23.514  1.00 61.39      C
ATOM    478  CB  ALA A 599     -23.089  28.166  24.436  1.00 61.38      C
ATOM    479  C   ALA A 599     -23.169  30.601  23.885  1.00 60.46      C
ATOM    480  O   ALA A 599     -22.130  31.046  23.372  1.00 60.20      O
ATOM    481  N   VAL A 600     -23.882  31.284  24.785  1.00 58.75      N
ATOM    482  CA  VAL A 600     -23.605  32.702  25.090  1.00 56.46      C
ATOM    483  CB  VAL A 600     -24.906  33.470  25.476  1.00 56.52      C
ATOM    484  CG1 VAL A 600     -24.599  34.905  25.936  1.00 55.85      C
ATOM    485  CG2 VAL A 600     -25.880  33.475  24.307  1.00 56.52      C
ATOM    486  C   VAL A 600     -22.531  32.871  26.173  1.00 54.73      C
ATOM    487  O   VAL A 600     -22.720  32.456  27.319  1.00 55.01      O
ATOM    488  N   LEU A 601     -21.421  33.503  25.793  1.00 52.14      N
ATOM    489  CA  LEU A 601     -20.283  33.744  26.694  1.00 49.71      C
ATOM    490  CB  LEU A 601     -18.954  33.579  25.932  1.00 49.78      C
ATOM    491  CG  LEU A 601     -18.605  32.227  25.309  1.00 50.22      C
ATOM    492  CD1 LEU A 601     -17.494  32.404  24.283  1.00 49.94      C
ATOM    493  CD2 LEU A 601     -18.198  31.228  26.385  1.00 52.06      C
ATOM    494  C   LEU A 601     -20.306  35.139  27.326  1.00 47.55      C
ATOM    495  O   LEU A 601     -19.674  35.362  28.359  1.00 47.03      O
ATOM    496  N   GLY A 602     -20.988  36.074  26.664  1.00 44.71      N
ATOM    497  CA  GLY A 602     -21.212  37.410  27.204  1.00 42.39      C
ATOM    498  C   GLY A 602     -22.203  38.163  26.352  1.00 40.35      C
ATOM    499  O   GLY A 602     -22.343  37.888  25.159  1.00 40.34      O
ATOM    500  N   GLU A 603     -22.916  39.099  26.968  1.00 38.75      N
ATOM    501  CA  GLU A 603     -23.787  40.015  26.229  1.00 37.72      C
ATOM    502  CB  GLU A 603     -25.266  39.556  26.245  1.00 37.69      C
ATOM    503  CG  GLU A 603     -26.163  40.253  25.173  1.00 38.85      C
ATOM    504  CD  GLU A 603     -27.439  39.455  24.804  1.00 40.53      C
```

FIG. 1J

```
ATOM    505  OE1 GLU A 603     -27.613  38.283  25.240  1.00 43.32      O
ATOM    506  OE2 GLU A 603     -28.269  40.007  24.047  1.00 44.38      O
ATOM    507  C   GLU A 603     -23.605  41.407  26.825  1.00 36.10      C
ATOM    508  O   GLU A 603     -23.516  41.555  28.039  1.00 36.82      O
ATOM    509  N   CYS A 604     -23.540  42.419  25.971  1.00 33.65      N
ATOM    510  CA  CYS A 604     -23.101  43.745  26.382  1.00 31.95      C
ATOM    511  CB  CYS A 604     -21.603  43.944  26.032  1.00 31.89      C
ATOM    512  SG  CYS A 604     -20.431  42.852  26.867  1.00 32.03      S
ATOM    513  C   CYS A 604     -23.918  44.785  25.647  1.00 30.39      C
ATOM    514  O   CYS A 604     -23.944  44.785  24.429  1.00 29.50      O
ATOM    515  N   ARG A 605     -24.558  45.669  26.401  1.00 29.23      N
ATOM    516  CA  ARG A 605     -25.288  46.784  25.852  1.00 29.99      C
ATOM    517  CB  ARG A 605     -26.229  47.399  26.898  1.00 29.33      C
ATOM    518  CG  ARG A 605     -27.579  46.686  27.004  1.00 30.53      C
ATOM    519  CD  ARG A 605     -28.487  47.267  28.088  1.00 30.34      C
ATOM    520  NE  ARG A 605     -29.635  46.348  28.290  1.00 34.53      N
ATOM    521  CZ  ARG A 605     -30.792  46.429  27.629  1.00 37.09      C
ATOM    522  NH1 ARG A 605     -31.010  47.398  26.724  1.00 35.96      N
ATOM    523  NH2 ARG A 605     -31.741  45.538  27.864  1.00 35.84      N
ATOM    524  C   ARG A 605     -24.325  47.864  25.376  1.00 29.69      C
ATOM    525  O   ARG A 605     -23.495  48.327  26.139  1.00 29.12      O
ATOM    526  N   VAL A 606     -24.499  48.274  24.124  1.00 30.60      N
ATOM    527  CA  VAL A 606     -23.722  49.343  23.485  1.00 30.63      C
ATOM    528  CB  VAL A 606     -24.237  49.567  22.030  1.00 30.68      C
ATOM    529  CG1 VAL A 606     -23.529  50.745  21.332  1.00 30.24      C
ATOM    530  CG2 VAL A 606     -24.088  48.294  21.213  1.00 30.76      C
ATOM    531  C   VAL A 606     -23.720  50.628  24.336  1.00 31.49      C
ATOM    532  O   VAL A 606     -22.681  51.271  24.521  1.00 31.35      O
ATOM    533  N   ARG A 607     -24.860  50.990  24.921  1.00 31.22      N
ATOM    534  CA  ARG A 607     -24.886  52.178  25.779  1.00 31.97      C
ATOM    535  CB  ARG A 607     -26.331  52.478  26.238  1.00 33.01      C
ATOM    536  CG  ARG A 607     -26.827  51.535  27.323  1.00 35.91      C
ATOM    537  CD  ARG A 607     -28.316  51.741  27.530  1.00 43.97      C
ATOM    538  NE  ARG A 607     -28.609  52.904  28.359  1.00 48.01      N
ATOM    539  CZ  ARG A 607     -29.830  53.428  28.500  1.00 51.07      C
ATOM    540  NH1 ARG A 607     -30.874  52.906  27.843  1.00 48.98      N
ATOM    541  NH2 ARG A 607     -30.005  54.477  29.301  1.00 51.01      N
ATOM    542  C   ARG A 607     -23.949  52.125  26.997  1.00 31.14      C
ATOM    543  O   ARG A 607     -23.594  53.180  27.541  1.00 31.98      O
ATOM    544  N   PHE A 608     -23.552  50.920  27.447  1.00 30.09      N
ATOM    545  CA  PHE A 608     -22.649  50.831  28.582  1.00 28.86      C
ATOM    546  CB  PHE A 608     -23.189  49.894  29.671  1.00 29.49      C
ATOM    547  CG  PHE A 608     -24.473  50.383  30.298  1.00 30.60      C
ATOM    548  CD1 PHE A 608     -24.525  51.619  30.932  1.00 31.13      C
ATOM    549  CE1 PHE A 608     -25.722  52.101  31.504  1.00 33.70      C
ATOM    550  CZ  PHE A 608     -26.888  51.310  31.439  1.00 33.23      C
ATOM    551  CE2 PHE A 608     -26.841  50.055  30.815  1.00 32.75      C
ATOM    552  CD2 PHE A 608     -25.630  49.600  30.243  1.00 32.92      C
ATOM    553  C   PHE A 608     -21.207  50.469  28.188  1.00 28.41      C
ATOM    554  O   PHE A 608     -20.355  50.252  29.049  1.00 27.33      O
ATOM    555  N   LEU A 609     -20.959  50.406  26.884  1.00 27.47      N
ATOM    556  CA  LEU A 609     -19.605  50.245  26.372  1.00 28.08      C
ATOM    557  CB  LEU A 609     -19.637  49.618  24.969  1.00 27.97      C
ATOM    558  CG  LEU A 609     -18.297  49.131  24.356  1.00 27.52      C
ATOM    559  CD1 LEU A 609     -18.573  48.167  23.226  1.00 28.80      C
ATOM    560  CD2 LEU A 609     -17.487  50.310  23.861  1.00 26.25      C
```

FIG. 1K

| ATOM | 561 | C | LEU | A | 609 | -18.979 | 51.624 | 26.387 | 1.00 | 27.46 | C |
|---|---|---|---|---|---|---|---|---|---|---|---|
| ATOM | 562 | O | LEU | A | 609 | -19.428 | 52.516 | 25.691 | 1.00 | 28.23 | O |
| ATOM | 563 | N | SER | A | 610 | -17.985 | 51.831 | 27.236 | 1.00 | 27.62 | N |
| ATOM | 564 | CA | SER | A | 610 | -17.388 | 53.154 | 27.352 | 1.00 | 27.46 | C |
| ATOM | 565 | CB | SER | A | 610 | -16.876 | 53.380 | 28.765 | 1.00 | 26.84 | C |
| ATOM | 566 | OG | SER | A | 610 | -16.185 | 52.243 | 29.211 | 1.00 | 28.05 | O |
| ATOM | 567 | C | SER | A | 610 | -16.254 | 53.394 | 26.326 | 1.00 | 27.66 | C |
| ATOM | 568 | O | SER | A | 610 | -16.032 | 54.521 | 25.895 | 1.00 | 27.61 | O |
| ATOM | 569 | N | PHE | A | 611 | -15.543 | 52.338 | 25.942 | 1.00 | 28.24 | N |
| ATOM | 570 | CA | PHE | A | 611 | -14.300 | 52.507 | 25.139 | 1.00 | 28.18 | C |
| ATOM | 571 | CB | PHE | A | 611 | -13.131 | 52.865 | 26.077 | 1.00 | 28.20 | C |
| ATOM | 572 | CG | PHE | A | 611 | -11.818 | 53.151 | 25.384 | 1.00 | 28.78 | C |
| ATOM | 573 | CD1 | PHE | A | 611 | -11.586 | 54.394 | 24.785 | 1.00 | 28.21 | C |
| ATOM | 574 | CE1 | PHE | A | 611 | -10.364 | 54.676 | 24.173 | 1.00 | 30.35 | C |
| ATOM | 575 | CZ | PHE | A | 611 | -9.358 | 53.708 | 24.165 | 1.00 | 28.77 | C |
| ATOM | 576 | CE2 | PHE | A | 611 | -9.573 | 52.465 | 24.761 | 1.00 | 28.45 | C |
| ATOM | 577 | CD2 | PHE | A | 611 | -10.807 | 52.199 | 25.372 | 1.00 | 28.02 | C |
| ATOM | 578 | C | PHE | A | 611 | -13.979 | 51.242 | 24.398 | 1.00 | 27.97 | C |
| ATOM | 579 | O | PHE | A | 611 | -14.269 | 50.145 | 24.871 | 1.00 | 28.38 | O |
| ATOM | 580 | N | LEU | A | 612 | -13.373 | 51.383 | 23.229 | 1.00 | 27.84 | N |
| ATOM | 581 | CA | LEU | A | 612 | -12.849 | 50.235 | 22.514 | 1.00 | 27.70 | C |
| ATOM | 582 | CB | LEU | A | 612 | -13.848 | 49.726 | 21.474 | 1.00 | 28.51 | C |
| ATOM | 583 | CG | LEU | A | 612 | -14.239 | 50.736 | 20.384 | 1.00 | 30.11 | C |
| ATOM | 584 | CD1 | LEU | A | 612 | -13.434 | 50.459 | 19.087 | 1.00 | 33.46 | C |
| ATOM | 585 | CD2 | LEU | A | 612 | -15.691 | 50.673 | 20.102 | 1.00 | 32.82 | C |
| ATOM | 586 | C | LEU | A | 612 | -11.525 | 50.602 | 21.852 | 1.00 | 28.49 | C |
| ATOM | 587 | O | LEU | A | 612 | -11.230 | 51.802 | 21.618 | 1.00 | 27.56 | O |
| ATOM | 588 | N | ALA | A | 613 | -10.730 | 49.575 | 21.556 | 1.00 | 28.35 | N |
| ATOM | 589 | CA | ALA | A | 613 | -9.451 | 49.789 | 20.872 | 1.00 | 28.75 | C |
| ATOM | 590 | CB | ALA | A | 613 | -8.413 | 50.443 | 21.791 | 1.00 | 27.94 | C |
| ATOM | 591 | C | ALA | A | 613 | -8.882 | 48.541 | 20.302 | 1.00 | 28.56 | C |
| ATOM | 592 | O | ALA | A | 613 | -9.247 | 47.434 | 20.683 | 1.00 | 28.13 | O |
| ATOM | 593 | N | VAL | A | 614 | -7.953 | 48.731 | 19.374 | 1.00 | 28.96 | N |
| ATOM | 594 | CA | VAL | A | 614 | -7.135 | 47.640 | 18.915 | 1.00 | 29.19 | C |
| ATOM | 595 | CB | VAL | A | 614 | -6.881 | 47.722 | 17.372 | 1.00 | 29.99 | C |
| ATOM | 596 | CG1 | VAL | A | 614 | -5.784 | 46.759 | 16.951 | 1.00 | 28.41 | C |
| ATOM | 597 | CG2 | VAL | A | 614 | -8.186 | 47.375 | 16.603 | 1.00 | 29.96 | C |
| ATOM | 598 | C | VAL | A | 614 | -5.863 | 47.796 | 19.751 | 1.00 | 28.74 | C |
| ATOM | 599 | O | VAL | A | 614 | -5.455 | 48.920 | 20.025 | 1.00 | 28.56 | O |
| ATOM | 600 | N | GLY | A | 615 | -5.274 | 46.687 | 20.200 | 1.00 | 28.53 | N |
| ATOM | 601 | CA | GLY | A | 615 | -4.081 | 46.774 | 21.055 | 1.00 | 29.65 | C |
| ATOM | 602 | C | GLY | A | 615 | -2.835 | 47.036 | 20.204 | 1.00 | 30.44 | C |
| ATOM | 603 | O | GLY | A | 615 | -2.934 | 47.097 | 18.978 | 1.00 | 30.76 | O |
| ATOM | 604 | N | ARG | A | 616 | -1.673 | 47.186 | 20.840 | 1.00 | 30.40 | N |
| ATOM | 605 | CA | ARG | A | 616 | -0.433 | 47.456 | 20.110 | 1.00 | 30.95 | C |
| ATOM | 606 | CB | ARG | A | 616 | 0.732 | 47.749 | 21.058 | 1.00 | 30.88 | C |
| ATOM | 607 | CG | ARG | A | 616 | 0.492 | 48.922 | 21.948 | 1.00 | 30.13 | C |
| ATOM | 608 | CD | ARG | A | 616 | 0.195 | 50.209 | 21.179 | 1.00 | 29.33 | C |
| ATOM | 609 | NE | ARG | A | 616 | 0.078 | 51.324 | 22.110 | 1.00 | 29.83 | N |
| ATOM | 610 | CZ | ARG | A | 616 | -0.232 | 52.567 | 21.770 | 1.00 | 33.27 | C |
| ATOM | 611 | NH1 | ARG | A | 616 | -0.489 | 52.864 | 20.505 | 1.00 | 33.66 | N |
| ATOM | 612 | NH2 | ARG | A | 616 | -0.320 | 53.511 | 22.701 | 1.00 | 33.73 | N |
| ATOM | 613 | C | ARG | A | 616 | -0.102 | 46.320 | 19.172 | 1.00 | 31.50 | C |
| ATOM | 614 | O | ARG | A | 616 | 0.407 | 46.553 | 18.097 | 1.00 | 32.79 | O |
| ATOM | 615 | N | ASP | A | 617 | -0.427 | 45.102 | 19.564 | 1.00 | 31.76 | N |
| ATOM | 616 | CA | ASP | A | 617 | -0.450 | 43.998 | 18.638 | 1.00 | 33.46 | C |

FIG. 1L

```
ATOM    617  CB   ASP A 617      -0.242  42.672  19.353  1.00 33.40   C
ATOM    618  CG   ASP A 617      -0.131  41.508  18.397  1.00 37.00   C
ATOM    619  OD1  ASP A 617      -1.018  41.345  17.548  1.00 36.91   O
ATOM    620  OD2  ASP A 617       0.848  40.722  18.503  1.00 41.81   O
ATOM    621  C    ASP A 617      -1.798  43.994  17.889  1.00 33.59   C
ATOM    622  O    ASP A 617      -2.875  43.906  18.502  1.00 31.75   O
ATOM    623  N    VAL A 618      -1.686  44.053  16.560  1.00 33.40   N
ATOM    624  CA   VAL A 618      -2.794  44.315  15.638  1.00 34.31   C
ATOM    625  CB   VAL A 618      -2.235  44.538  14.191  1.00 34.51   C
ATOM    626  CG1  VAL A 618      -1.878  43.204  13.534  1.00 33.81   C
ATOM    627  CG2  VAL A 618      -3.216  45.298  13.362  1.00 37.28   C
ATOM    628  C    VAL A 618      -3.874  43.229  15.673  1.00 33.73   C
ATOM    629  O    VAL A 618      -4.978  43.426  15.200  1.00 34.57   O
ATOM    630  N    HIS A 619      -3.547  42.081  16.236  1.00 33.90   N
ATOM    631  CA   HIS A 619      -4.514  40.999  16.418  1.00 34.73   C
ATOM    632  CB   HIS A 619      -3.775  39.711  16.723  1.00 35.52   C
ATOM    633  CG   HIS A 619      -2.843  39.265  15.640  1.00 37.50   C
ATOM    634  ND1  HIS A 619      -1.558  39.747  15.521  1.00 38.98   N
ATOM    635  CE1  HIS A 619      -0.972  39.171  14.489  1.00 40.16   C
ATOM    636  NE2  HIS A 619      -1.824  38.319  13.948  1.00 41.17   N
ATOM    637  CD2  HIS A 619      -3.003  38.360  14.649  1.00 38.81   C
ATOM    638  C    HIS A 619      -5.497  41.219  17.575  1.00 33.76   C
ATOM    639  O    HIS A 619      -6.546  40.576  17.648  1.00 33.94   O
ATOM    640  N    THR A 620      -5.143  42.096  18.494  1.00 33.08   N
ATOM    641  CA   THR A 620      -5.883  42.154  19.746  1.00 32.76   C
ATOM    642  CB   THR A 620      -4.977  42.468  20.964  1.00 31.93   C
ATOM    643  OG1  THR A 620      -4.336  43.725  20.771  1.00 31.98   O
ATOM    644  CG2  THR A 620      -3.938  41.362  21.214  1.00 32.36   C
ATOM    645  C    THR A 620      -6.990  43.200  19.675  1.00 31.96   C
ATOM    646  O    THR A 620      -6.774  44.319  19.194  1.00 32.10   O
ATOM    647  N    PHE A 621      -8.157  42.827  20.175  1.00 30.97   N
ATOM    648  CA   PHE A 621      -9.236  43.799  20.364  1.00 30.26   C
ATOM    649  CB   PHE A 621     -10.362  43.502  19.360  1.00 29.67   C
ATOM    650  CG   PHE A 621     -11.559  44.418  19.488  1.00 30.49   C
ATOM    651  CD1  PHE A 621     -11.459  45.781  19.176  1.00 33.08   C
ATOM    652  CE1  PHE A 621     -12.577  46.645  19.298  1.00 33.66   C
ATOM    653  CZ   PHE A 621     -13.786  46.132  19.735  1.00 29.48   C
ATOM    654  CE2  PHE A 621     -13.892  44.775  20.057  1.00 29.92   C
ATOM    655  CD2  PHE A 621     -12.775  43.921  19.927  1.00 30.88   C
ATOM    656  C    PHE A 621      -9.739  43.810  21.830  1.00 28.60   C
ATOM    657  O    PHE A 621      -9.841  42.765  22.449  1.00 28.63   O
ATOM    658  N    ALA A 622     -10.041  44.987  22.370  1.00 28.14   N
ATOM    659  CA   ALA A 622     -10.683  45.084  23.697  1.00 28.12   C
ATOM    660  CB   ALA A 622      -9.615  45.310  24.827  1.00 27.24   C
ATOM    661  C    ALA A 622     -11.729  46.173  23.748  1.00 27.39   C
ATOM    662  O    ALA A 622     -11.629  47.193  23.065  1.00 27.85   O
ATOM    663  N    PHE A 623     -12.747  45.963  24.563  1.00 27.00   N
ATOM    664  CA   PHE A 623     -13.650  47.056  24.890  1.00 26.45   C
ATOM    665  CB   PHE A 623     -14.979  47.002  24.090  1.00 26.06   C
ATOM    666  CG   PHE A 623     -15.796  45.751  24.312  1.00 28.41   C
ATOM    667  CD1  PHE A 623     -16.728  45.677  25.353  1.00 27.12   C
ATOM    668  CE1  PHE A 623     -17.510  44.508  25.543  1.00 30.38   C
ATOM    669  CZ   PHE A 623     -17.355  43.435  24.677  1.00 28.05   C
ATOM    670  CE2  PHE A 623     -16.430  43.519  23.620  1.00 28.49   C
ATOM    671  CD2  PHE A 623     -15.669  44.664  23.444  1.00 27.63   C
ATOM    672  C    PHE A 623     -13.872  47.075  26.381  1.00 25.63   C
```

FIG. 1M

```
ATOM    673  O    PHE A 623     -13.797  46.040  27.043  1.00 25.65    O
ATOM    674  N    ILE A 624     -14.121  48.258  26.908  1.00 25.38    N
ATOM    675  CA   ILE A 624     -14.407  48.410  28.322  1.00 25.47    C
ATOM    676  CB   ILE A 624     -13.603  49.570  28.948  1.00 25.41    C
ATOM    677  CG1  ILE A 624     -12.094  49.316  28.763  1.00 24.63    C
ATOM    678  CD1  ILE A 624     -11.197  50.544  29.213  1.00 25.99    C
ATOM    679  CG2  ILE A 624     -13.961  49.793  30.456  1.00 23.35    C
ATOM    680  C    ILE A 624     -15.908  48.641  28.481  1.00 25.79    C
ATOM    681  O    ILE A 624     -16.502  49.448  27.786  1.00 25.32    O
ATOM    682  N    MET A 625     -16.498  47.891  29.394  1.00 26.45    N
ATOM    683  CA   MET A 625     -17.906  48.056  29.766  1.00 26.60    C
ATOM    684  CB   MET A 625     -18.554  46.678  29.842  1.00 27.03    C
ATOM    685  CG   MET A 625     -18.755  45.984  28.467  1.00 25.49    C
ATOM    686  SD   MET A 625     -19.878  46.848  27.351  1.00 30.31    S
ATOM    687  CE   MET A 625     -21.422  46.821  28.279  1.00 29.57    C
ATOM    688  C    MET A 625     -18.020  48.716  31.117  1.00 26.63    C
ATOM    689  O    MET A 625     -17.264  48.409  32.005  1.00 26.86    O
ATOM    690  N    ALA A 626     -18.958  49.636  31.285  1.00 27.70    N
ATOM    691  CA   ALA A 626     -19.329  50.039  32.628  1.00 29.34    C
ATOM    692  CB   ALA A 626     -19.952  51.407  32.607  1.00 28.58    C
ATOM    693  C    ALA A 626     -20.324  48.985  33.142  1.00 30.86    C
ATOM    694  O    ALA A 626     -21.538  49.091  32.886  1.00 31.60    O
ATOM    695  N    ALA A 627     -19.793  47.970  33.822  1.00 32.41    N
ATOM    696  CA   ALA A 627     -20.588  46.875  34.442  1.00 33.84    C
ATOM    697  CB   ALA A 627     -19.676  45.844  35.071  1.00 33.58    C
ATOM    698  C    ALA A 627     -21.588  47.387  35.480  1.00 34.95    C
ATOM    699  O    ALA A 627     -22.695  46.850  35.605  1.00 34.88    O
ATOM    700  N    GLY A 628     -21.166  48.417  36.213  1.00 36.05    N
ATOM    701  CA   GLY A 628     -22.013  49.200  37.103  1.00 37.83    C
ATOM    702  C    GLY A 628     -21.566  50.657  37.068  1.00 39.37    C
ATOM    703  O    GLY A 628     -20.645  50.996  36.325  1.00 39.01    O
ATOM    704  N    PRO A 629     -22.244  51.538  37.838  1.00 40.51    N
ATOM    705  CA   PRO A 629     -21.924  52.966  37.925  1.00 41.46    C
ATOM    706  CB   PRO A 629     -22.784  53.443  39.099  1.00 41.66    C
ATOM    707  CG   PRO A 629     -23.994  52.555  39.012  1.00 41.75    C
ATOM    708  CD   PRO A 629     -23.428  51.203  38.655  1.00 41.10    C
ATOM    709  C    PRO A 629     -20.446  53.242  38.193  1.00 41.92    C
ATOM    710  O    PRO A 629     -19.879  54.173  37.611  1.00 43.23    O
ATOM    711  N    ALA A 630     -19.806  52.433  39.031  1.00 41.70    N
ATOM    712  CA   ALA A 630     -18.383  52.680  39.321  1.00 40.74    C
ATOM    713  CB   ALA A 630     -18.222  53.200  40.754  1.00 41.41    C
ATOM    714  C    ALA A 630     -17.540  51.432  39.107  1.00 39.58    C
ATOM    715  O    ALA A 630     -16.569  51.205  39.826  1.00 39.24    O
ATOM    716  N    SER A 631     -17.926  50.626  38.124  1.00 37.79    N
ATOM    717  CA   SER A 631     -17.320  49.321  37.946  1.00 36.77    C
ATOM    718  CB   SER A 631     -18.253  48.259  38.547  1.00 37.01    C
ATOM    719  OG   SER A 631     -17.521  47.129  38.975  1.00 39.61    O
ATOM    720  C    SER A 631     -17.054  49.042  36.468  1.00 35.04    C
ATOM    721  O    SER A 631     -17.979  49.020  35.660  1.00 34.72    O
ATOM    722  N    PHE A 632     -15.789  48.822  36.118  1.00 33.25    N
ATOM    723  CA   PHE A 632     -15.419  48.627  34.714  1.00 31.45    C
ATOM    724  CB   PHE A 632     -14.500  49.761  34.215  1.00 31.01    C
ATOM    725  CG   PHE A 632     -15.077  51.118  34.465  1.00 30.52    C
ATOM    726  CD1  PHE A 632     -16.112  51.598  33.673  1.00 29.73    C
ATOM    727  CE1  PHE A 632     -16.685  52.842  33.927  1.00 31.92    C
ATOM    728  CZ   PHE A 632     -16.236  53.613  35.017  1.00 30.96    C
```

FIG. 1N

| | | | | | | | | | |
|---|---|---|---|---|---|---|---|---|---|
| ATOM | 729 | CE2 | PHE A 632 | -15.212 | 53.119 | 35.825 | 1.00 | 31.57 | C |
| ATOM | 730 | CD2 | PHE A 632 | -14.648 | 51.884 | 35.552 | 1.00 | 31.32 | C |
| ATOM | 731 | C | PHE A 632 | -14.837 | 47.262 | 34.441 | 1.00 | 30.88 | C |
| ATOM | 732 | O | PHE A 632 | -14.049 | 46.742 | 35.217 | 1.00 | 30.19 | O |
| ATOM | 733 | N | CYS A 633 | -15.238 | 46.701 | 33.312 | 1.00 | 30.46 | N |
| ATOM | 734 | CA | CYS A 633 | -14.811 | 45.377 | 32.919 | 1.00 | 30.74 | C |
| ATOM | 735 | CB | CYS A 633 | -16.050 | 44.440 | 32.959 | 1.00 | 29.64 | C |
| ATOM | 736 | SG | CYS A 633 | -15.745 | 42.754 | 32.507 | 1.00 | 33.94 | S |
| ATOM | 737 | C | CYS A 633 | -14.234 | 45.433 | 31.505 | 1.00 | 29.19 | C |
| ATOM | 738 | O | CYS A 633 | -14.858 | 45.971 | 30.618 | 1.00 | 30.33 | O |
| ATOM | 739 | N | CYS A 634 | -13.066 | 44.856 | 31.293 | 1.00 | 28.29 | N |
| ATOM | 740 | CA | CYS A 634 | -12.456 | 44.840 | 29.951 | 1.00 | 27.17 | C |
| ATOM | 741 | CB | CYS A 634 | -11.002 | 45.266 | 30.045 | 1.00 | 27.33 | C |
| ATOM | 742 | SG | CYS A 634 | -10.205 | 45.416 | 28.425 | 1.00 | 26.69 | S |
| ATOM | 743 | C | CYS A 634 | -12.563 | 43.467 | 29.262 | 1.00 | 26.48 | C |
| ATOM | 744 | O | CYS A 634 | -12.050 | 42.487 | 29.766 | 1.00 | 26.42 | O |
| ATOM | 745 | N | HIS A 635 | -13.249 | 43.412 | 28.119 | 1.00 | 25.87 | N |
| ATOM | 746 | CA | HIS A 635 | -13.421 | 42.176 | 27.351 | 1.00 | 26.81 | C |
| ATOM | 747 | CB | HIS A 635 | -14.836 | 42.117 | 26.771 | 1.00 | 27.11 | C |
| ATOM | 748 | CG | HIS A 635 | -15.907 | 42.021 | 27.823 | 1.00 | 26.94 | C |
| ATOM | 749 | ND1 | HIS A 635 | -16.504 | 40.829 | 28.173 | 1.00 | 28.99 | N |
| ATOM | 750 | CE1 | HIS A 635 | -17.395 | 41.047 | 29.123 | 1.00 | 29.70 | C |
| ATOM | 751 | NE2 | HIS A 635 | -17.409 | 42.342 | 29.392 | 1.00 | 29.08 | N |
| ATOM | 752 | CD2 | HIS A 635 | -16.475 | 42.969 | 28.601 | 1.00 | 27.56 | C |
| ATOM | 753 | C | HIS A 635 | -12.410 | 42.110 | 26.217 | 1.00 | 27.15 | C |
| ATOM | 754 | O | HIS A 635 | -12.272 | 43.070 | 25.483 | 1.00 | 26.58 | O |
| ATOM | 755 | N | MET A 636 | -11.724 | 40.980 | 26.066 | 1.00 | 28.35 | N |
| ATOM | 756 | CA | MET A 636 | -10.543 | 40.928 | 25.177 | 1.00 | 29.62 | C |
| ATOM | 757 | CB | MET A 636 | -9.278 | 40.841 | 26.024 | 1.00 | 29.24 | C |
| ATOM | 758 | CG | MET A 636 | -8.979 | 42.131 | 26.738 | 1.00 | 29.33 | C |
| ATOM | 759 | SD | MET A 636 | -7.884 | 41.963 | 28.164 | 1.00 | 31.19 | S |
| ATOM | 760 | CE | MET A 636 | -8.773 | 40.883 | 29.275 | 1.00 | 27.06 | C |
| ATOM | 761 | C | MET A 636 | -10.591 | 39.796 | 24.174 | 1.00 | 29.74 | C |
| ATOM | 762 | O | MET A 636 | -11.132 | 38.743 | 24.474 | 1.00 | 30.53 | O |
| ATOM | 763 | N | PHE A 637 | -10.038 | 40.031 | 22.983 | 1.00 | 30.44 | N |
| ATOM | 764 | CA | PHE A 637 | -10.127 | 39.078 | 21.870 | 1.00 | 31.47 | C |
| ATOM | 765 | CB | PHE A 637 | -11.257 | 39.486 | 20.883 | 1.00 | 31.61 | C |
| ATOM | 766 | CG | PHE A 637 | -12.611 | 39.667 | 21.536 | 1.00 | 31.86 | C |
| ATOM | 767 | CD1 | PHE A 637 | -12.939 | 40.871 | 22.144 | 1.00 | 28.50 | C |
| ATOM | 768 | CE1 | PHE A 637 | -14.179 | 41.047 | 22.774 | 1.00 | 30.24 | C |
| ATOM | 769 | CZ | PHE A 637 | -15.112 | 40.008 | 22.771 | 1.00 | 30.92 | C |
| ATOM | 770 | CE2 | PHE A 637 | -14.801 | 38.786 | 22.163 | 1.00 | 31.33 | C |
| ATOM | 771 | CD2 | PHE A 637 | -13.552 | 38.624 | 21.535 | 1.00 | 32.20 | C |
| ATOM | 772 | C | PHE A 637 | -8.816 | 38.999 | 21.082 | 1.00 | 32.19 | C |
| ATOM | 773 | O | PHE A 637 | -8.081 | 39.976 | 20.993 | 1.00 | 31.58 | O |
| ATOM | 774 | N | TRP A 638 | -8.546 | 37.826 | 20.512 | 1.00 | 33.61 | N |
| ATOM | 775 | CA | TRP A 638 | -7.476 | 37.668 | 19.529 | 1.00 | 34.73 | C |
| ATOM | 776 | CB | TRP A 638 | -6.547 | 36.512 | 19.908 | 1.00 | 34.99 | C |
| ATOM | 777 | CG | TRP A 638 | -5.352 | 36.403 | 18.991 | 1.00 | 35.06 | C |
| ATOM | 778 | CD1 | TRP A 638 | -5.290 | 35.734 | 17.805 | 1.00 | 35.04 | C |
| ATOM | 779 | NE1 | TRP A 638 | -4.037 | 35.868 | 17.241 | 1.00 | 35.85 | N |
| ATOM | 780 | CE2 | TRP A 638 | -3.263 | 36.642 | 18.065 | 1.00 | 36.07 | C |
| ATOM | 781 | CD2 | TRP A 638 | -4.061 | 36.995 | 19.186 | 1.00 | 36.08 | C |
| ATOM | 782 | CE3 | TRP A 638 | -3.504 | 37.806 | 20.184 | 1.00 | 36.27 | C |
| ATOM | 783 | CZ3 | TRP A 638 | -2.172 | 38.219 | 20.044 | 1.00 | 35.11 | C |
| ATOM | 784 | CH2 | TRP A 638 | -1.406 | 37.847 | 18.915 | 1.00 | 35.16 | C |

FIG. 1O

```
ATOM    785  CZ2 TRP A 638      -1.924  37.057  17.929  1.00 35.30     C
ATOM    786  C   TRP A 638      -8.122  37.405  18.169  1.00 34.91     C
ATOM    787  O   TRP A 638      -8.939  36.495  18.014  1.00 35.93     O
ATOM    788  N   CYS A 639      -7.788  38.227  17.197  1.00 35.79     N
ATOM    789  CA  CYS A 639      -8.434  38.156  15.898  1.00 37.13     C
ATOM    790  CB  CYS A 639      -9.174  39.457  15.606  1.00 36.48     C
ATOM    791  SG  CYS A 639     -10.212  40.086  16.954  1.00 35.98     S
ATOM    792  C   CYS A 639      -7.431  37.866  14.780  1.00 37.98     C
ATOM    793  O   CYS A 639      -6.371  38.468  14.721  1.00 38.44     O
ATOM    794  N   GLU A 640      -7.808  36.962  13.885  1.00 39.92     N
ATOM    795  CA  GLU A 640      -6.999  36.611  12.712  1.00 40.98     C
ATOM    796  CB  GLU A 640      -6.716  35.111  12.694  1.00 41.22     C
ATOM    797  CG  GLU A 640      -5.869  34.600  13.851  1.00 42.98     C
ATOM    798  CD  GLU A 640      -4.404  34.954  13.714  1.00 45.42     C
ATOM    799  OE1 GLU A 640      -4.006  35.480  12.645  1.00 46.78     O
ATOM    800  OE2 GLU A 640      -3.647  34.698  14.680  1.00 46.31     O
ATOM    801  C   GLU A 640      -7.758  36.991  11.441  1.00 41.43     C
ATOM    802  O   GLU A 640      -8.938  36.663  11.319  1.00 41.74     O
ATOM    803  N   PRO A 641      -7.088  37.664  10.481  1.00 41.71     N
ATOM    804  CA  PRO A 641      -5.655  37.989  10.441  1.00 41.18     C
ATOM    805  CB  PRO A 641      -5.428  38.351   8.972  1.00 41.65     C
ATOM    806  CG  PRO A 641      -6.751  38.900   8.508  1.00 42.03     C
ATOM    807  CD  PRO A 641      -7.810  38.183   9.298  1.00 41.93     C
ATOM    808  C   PRO A 641      -5.280  39.164  11.333  1.00 40.56     C
ATOM    809  O   PRO A 641      -4.110  39.336  11.683  1.00 40.51     O
ATOM    810  N   ASN A 642      -6.280  39.979  11.664  1.00 39.76     N
ATOM    811  CA  ASN A 642      -6.141  41.096  12.585  1.00 38.25     C
ATOM    812  CB  ASN A 642      -5.452  42.299  11.926  1.00 38.08     C
ATOM    813  CG  ASN A 642      -6.189  42.794  10.687  1.00 40.53     C
ATOM    814  OD1 ASN A 642      -7.410  43.000  10.708  1.00 42.71     O
ATOM    815  ND2 ASN A 642      -5.451  42.970   9.593  1.00 40.99     N
ATOM    816  C   ASN A 642      -7.526  41.468  13.118  1.00 37.32     C
ATOM    817  O   ASN A 642      -8.536  40.835  12.752  1.00 37.12     O
ATOM    818  N   ALA A 643      -7.564  42.503  13.953  1.00 35.93     N
ATOM    819  CA  ALA A 643      -8.797  42.941  14.609  1.00 35.60     C
ATOM    820  CB  ALA A 643      -8.478  43.446  16.032  1.00 34.13     C
ATOM    821  C   ALA A 643      -9.565  44.016  13.813  1.00 34.98     C
ATOM    822  O   ALA A 643     -10.487  44.639  14.357  1.00 35.16     O
ATOM    823  N   ALA A 644      -9.175  44.271  12.555  1.00 34.10     N
ATOM    824  CA  ALA A 644      -9.760  45.404  11.851  1.00 33.92     C
ATOM    825  CB  ALA A 644      -9.054  45.731  10.493  1.00 34.19     C
ATOM    826  C   ALA A 644     -11.273  45.239  11.692  1.00 33.76     C
ATOM    827  O   ALA A 644     -12.022  46.111  12.114  1.00 33.79     O
ATOM    828  N   SER A 645     -11.730  44.117  11.169  1.00 34.34     N
ATOM    829  CA  SER A 645     -13.166  43.989  10.914  1.00 35.29     C
ATOM    830  CB  SER A 645     -13.484  42.808  10.007  1.00 35.52     C
ATOM    831  OG  SER A 645     -13.377  41.591  10.695  1.00 41.42     O
ATOM    832  C   SER A 645     -14.038  44.025  12.190  1.00 34.60     C
ATOM    833  O   SER A 645     -15.080  44.667  12.194  1.00 33.43     O
ATOM    834  N   LEU A 646     -13.574  43.401  13.277  1.00 33.91     N
ATOM    835  CA  LEU A 646     -14.325  43.394  14.535  1.00 32.90     C
ATOM    836  CB  LEU A 646     -13.746  42.387  15.549  1.00 33.22     C
ATOM    837  CG  LEU A 646     -14.422  42.257  16.933  1.00 32.99     C
ATOM    838  CD1 LEU A 646     -15.929  41.935  16.865  1.00 31.59     C
ATOM    839  CD2 LEU A 646     -13.684  41.222  17.792  1.00 31.74     C
ATOM    840  C   LEU A 646     -14.402  44.772  15.144  1.00 33.28     C
```

FIG. 1P

```
ATOM    841  O    LEU A 646     -15.490  45.222  15.520  1.00 33.40      O
ATOM    842  N    SER A 647     -13.266  45.462  15.236  1.00 33.10      N
ATOM    843  CA   SER A 647     -13.257  46.808  15.791  1.00 33.10      C
ATOM    844  CB   SER A 647     -11.834  47.366  15.929  1.00 33.02      C
ATOM    845  OG   SER A 647     -11.135  47.362  14.692  1.00 34.80      O
ATOM    846  C    SER A 647     -14.129  47.765  14.976  1.00 33.75      C
ATOM    847  O    SER A 647     -14.798  48.643  15.541  1.00 33.35      O
ATOM    848  N    GLU A 648     -14.101  47.601  13.656  1.00 33.41      N
ATOM    849  CA   GLU A 648     -14.932  48.397  12.747  1.00 34.85      C
ATOM    850  CB   GLU A 648     -14.621  48.040  11.287  1.00 34.26      C
ATOM    851  CG   GLU A 648     -13.392  48.741  10.742  1.00 38.34      C
ATOM    852  CD   GLU A 648     -12.795  48.072   9.492  1.00 39.86      C
ATOM    853  OE1  GLU A 648     -13.321  47.035   9.004  1.00 47.20      O
ATOM    854  OE2  GLU A 648     -11.773  48.588   9.001  1.00 46.10      O
ATOM    855  C    GLU A 648     -16.414  48.186  13.034  1.00 32.85      C
ATOM    856  O    GLU A 648     -17.151  49.154  13.189  1.00 32.60      O
ATOM    857  N    ALA A 649     -16.824  46.920  13.099  1.00 32.32      N
ATOM    858  CA   ALA A 649     -18.211  46.526  13.392  1.00 32.59      C
ATOM    859  CB   ALA A 649     -18.361  45.003  13.365  1.00 32.24      C
ATOM    860  C    ALA A 649     -18.665  47.084  14.731  1.00 32.28      C
ATOM    861  O    ALA A 649     -19.741  47.654  14.826  1.00 33.07      O
ATOM    862  N    VAL A 650     -17.826  46.965  15.761  1.00 31.91      N
ATOM    863  CA   VAL A 650     -18.202  47.466  17.084  1.00 31.38      C
ATOM    864  CB   VAL A 650     -17.323  46.882  18.209  1.00 31.79      C
ATOM    865  CG1  VAL A 650     -17.674  47.532  19.573  1.00 30.57      C
ATOM    866  CG2  VAL A 650     -17.472  45.362  18.234  1.00 30.81      C
ATOM    867  C    VAL A 650     -18.215  48.987  17.127  1.00 31.23      C
ATOM    868  O    VAL A 650     -19.132  49.592  17.693  1.00 30.13      O
ATOM    869  N    GLN A 651     -17.212  49.620  16.523  1.00 30.30      N
ATOM    870  CA   GLN A 651     -17.262  51.077  16.439  1.00 30.08      C
ATOM    871  CB   GLN A 651     -16.021  51.644  15.759  1.00 30.19      C
ATOM    872  CG   GLN A 651     -15.935  53.160  15.861  1.00 28.82      C
ATOM    873  CD   GLN A 651     -14.955  53.739  14.864  1.00 31.16      C
ATOM    874  OE1  GLN A 651     -14.337  53.005  14.100  1.00 33.15      O
ATOM    875  NE2  GLN A 651     -14.819  55.050  14.858  1.00 32.87      N
ATOM    876  C    GLN A 651     -18.518  51.566  15.685  1.00 29.39      C
ATOM    877  O    GLN A 651     -19.158  52.529  16.111  1.00 29.70      O
ATOM    878  N    ALA A 652     -18.843  50.919  14.565  1.00 29.24      N
ATOM    879  CA   ALA A 652     -20.030  51.298  13.776  1.00 28.09      C
ATOM    880  CB   ALA A 652     -20.139  50.448  12.520  1.00 27.66      C
ATOM    881  C    ALA A 652     -21.318  51.196  14.612  1.00 28.18      C
ATOM    882  O    ALA A 652     -22.132  52.100  14.593  1.00 27.86      O
ATOM    883  N    ALA A 653     -21.451  50.116  15.387  1.00 27.73      N
ATOM    884  CA   ALA A 653     -22.584  49.938  16.282  1.00 27.99      C
ATOM    885  CB   ALA A 653     -22.481  48.565  17.008  1.00 28.11      C
ATOM    886  C    ALA A 653     -22.732  51.089  17.274  1.00 28.08      C
ATOM    887  O    ALA A 653     -23.841  51.602  17.461  1.00 27.41      O
ATOM    888  N    CYS A 654     -21.620  51.510  17.903  1.00 27.68      N
ATOM    889  CA   CYS A 654     -21.627  52.664  18.817  1.00 28.26      C
ATOM    890  CB   CYS A 654     -20.240  52.879  19.469  1.00 28.71      C
ATOM    891  SG   CYS A 654     -19.659  51.477  20.517  1.00 29.78      S
ATOM    892  C    CYS A 654     -22.066  53.983  18.164  1.00 28.63      C
ATOM    893  O    CYS A 654     -22.780  54.771  18.779  1.00 28.06      O
ATOM    894  N    MET A 655     -21.580  54.238  16.947  1.00 29.18      N
ATOM    895  CA   MET A 655     -21.862  55.480  16.232  1.00 30.91      C
ATOM    896  CB   MET A 655     -20.887  55.641  15.044  1.00 30.48      C
```

FIG. 1Q

```
ATOM    897  CG   MET A 655     -19.428  55.889  15.463  1.00 31.59      C
ATOM    898  SD   MET A 655     -18.277  56.236  14.097  1.00 34.16      S
ATOM    899  CE   MET A 655     -18.311  54.679  13.315  1.00 28.65      C
ATOM    900  C    MET A 655     -23.323  55.526  15.735  1.00 30.78      C
ATOM    901  O    MET A 655     -23.958  56.569  15.765  1.00 30.72      O
ATOM    902  N    LEU A 656     -23.831  54.386  15.279  1.00 32.18      N
ATOM    903  CA   LEU A 656     -25.254  54.236  14.920  1.00 33.98      C
ATOM    904  CB   LEU A 656     -25.496  52.832  14.393  1.00 34.15      C
ATOM    905  CG   LEU A 656     -25.589  52.432  12.939  1.00 39.72      C
ATOM    906  CD1  LEU A 656     -26.066  50.980  12.932  1.00 42.40      C
ATOM    907  CD2  LEU A 656     -26.576  53.299  12.153  1.00 42.32      C
ATOM    908  C    LEU A 656     -26.168  54.448  16.137  1.00 33.50      C
ATOM    909  O    LEU A 656     -27.165  55.177  16.082  1.00 32.69      O
ATOM    910  N    ARG A 657     -25.807  53.779  17.225  1.00 33.67      N
ATOM    911  CA   ARG A 657     -26.523  53.837  18.486  1.00 34.33      C
ATOM    912  CB   ARG A 657     -25.821  52.943  19.495  1.00 34.53      C
ATOM    913  CG   ARG A 657     -26.495  52.869  20.832  1.00 37.88      C
ATOM    914  CD   ARG A 657     -27.796  52.120  20.782  1.00 43.32      C
ATOM    915  NE   ARG A 657     -28.469  52.326  22.057  1.00 51.60      N
ATOM    916  CZ   ARG A 657     -29.726  51.984  22.322  1.00 54.68      C
ATOM    917  NH1  ARG A 657     -30.488  51.392  21.390  1.00 54.53      N
ATOM    918  NH2  ARG A 657     -30.216  52.245  23.529  1.00 54.75      N
ATOM    919  C    ARG A 657     -26.649  55.243  19.055  1.00 34.69      C
ATOM    920  O    ARG A 657     -27.720  55.633  19.547  1.00 34.18      O
ATOM    921  N    TYR A 658     -25.562  56.005  19.005  1.00 33.90      N
ATOM    922  CA   TYR A 658     -25.583  57.358  19.525  1.00 34.59      C
ATOM    923  CB   TYR A 658     -24.169  57.934  19.556  1.00 34.42      C
ATOM    924  CG   TYR A 658     -24.093  59.386  19.951  1.00 34.94      C
ATOM    925  CD1  TYR A 658     -24.500  59.817  21.223  1.00 34.57      C
ATOM    926  CE1  TYR A 658     -24.423  61.163  21.583  1.00 35.32      C
ATOM    927  CZ   TYR A 658     -23.935  62.084  20.664  1.00 35.71      C
ATOM    928  OH   TYR A 658     -23.832  63.415  20.987  1.00 37.00      O
ATOM    929  CE2  TYR A 658     -23.525  61.679  19.402  1.00 36.65      C
ATOM    930  CD2  TYR A 658     -23.611  60.340  19.050  1.00 34.93      C
ATOM    931  C    TYR A 658     -26.546  58.271  18.749  1.00 35.31      C
ATOM    932  O    TYR A 658     -27.289  59.063  19.344  1.00 34.08      O
ATOM    933  N    GLN A 659     -26.543  58.152  17.427  1.00 36.64      N
ATOM    934  CA   GLN A 659     -27.469  58.934  16.609  1.00 38.18      C
ATOM    935  CB   GLN A 659     -27.133  58.838  15.119  1.00 37.56      C
ATOM    936  CG   GLN A 659     -27.957  59.797  14.230  1.00 40.32      C
ATOM    937  CD   GLN A 659     -27.895  61.273  14.673  1.00 45.05      C
ATOM    938  OE1  GLN A 659     -26.847  61.780  15.085  1.00 46.81      O
ATOM    939  NE2  GLN A 659     -29.023  61.966  14.570  1.00 47.71      N
ATOM    940  C    GLN A 659     -28.936  58.521  16.876  1.00 39.29      C
ATOM    941  O    GLN A 659     -29.833  59.376  16.958  1.00 38.37      O
ATOM    942  N    LYS A 660     -29.168  57.220  17.011  1.00 40.98      N
ATOM    943  CA   LYS A 660     -30.510  56.723  17.352  1.00 43.19      C
ATOM    944  CB   LYS A 660     -30.583  55.206  17.294  1.00 42.96      C
ATOM    945  CG   LYS A 660     -30.997  54.731  15.909  1.00 46.37      C
ATOM    946  CD   LYS A 660     -30.893  53.224  15.763  1.00 50.01      C
ATOM    947  CE   LYS A 660     -30.466  52.815  14.343  1.00 51.48      C
ATOM    948  NZ   LYS A 660     -29.908  51.416  14.353  1.00 51.91      N
ATOM    949  C    LYS A 660     -31.040  57.273  18.672  1.00 43.84      C
ATOM    950  O    LYS A 660     -32.203  57.671  18.750  1.00 44.21      O
ATOM    951  N    CYS A 661     -30.175  57.339  19.677  1.00 45.01      N
ATOM    952  CA   CYS A 661     -30.516  57.920  20.974  1.00 46.89      C
```

FIG. 1R

```
ATOM    953  CB  CYS A 661     -29.472  57.533  22.030  1.00 46.61      C
ATOM    954  SG  CYS A 661     -29.435  55.702  22.312  1.00 48.96      S
ATOM    955  C   CYS A 661     -30.786  59.430  20.950  1.00 48.19      C
ATOM    956  O   CYS A 661     -31.763  59.889  21.553  1.00 48.16      O
ATOM    957  N   LEU A 662     -29.941  60.200  20.258  1.00 49.41      N
ATOM    958  CA  LEU A 662     -30.199  61.625  20.055  1.00 51.08      C
ATOM    959  CB  LEU A 662     -29.102  62.289  19.218  1.00 50.22      C
ATOM    960  CG  LEU A 662     -27.783  62.627  19.904  1.00 49.78      C
ATOM    961  CD1 LEU A 662     -26.879  63.325  18.913  1.00 49.09      C
ATOM    962  CD2 LEU A 662     -27.987  63.488  21.135  1.00 48.81      C
ATOM    963  C   LEU A 662     -31.549  61.844  19.380  1.00 52.54      C
ATOM    964  O   LEU A 662     -32.306  62.721  19.782  1.00 52.57      O
ATOM    965  N   ASP A 663     -31.821  61.040  18.352  1.00 54.79      N
ATOM    966  CA  ASP A 663     -33.063  61.094  17.584  1.00 57.33      C
ATOM    967  CB  ASP A 663     -32.984  60.179  16.366  1.00 57.71      C
ATOM    968  CG  ASP A 663     -32.964  60.947  15.064  1.00 60.51      C
ATOM    969  OD1 ASP A 663     -32.375  62.058  15.039  1.00 61.61      O
ATOM    970  OD2 ASP A 663     -33.551  60.434  14.071  1.00 63.95      O
ATOM    971  C   ASP A 663     -34.310  60.750  18.383  1.00 58.45      C
ATOM    972  O   ASP A 663     -35.327  61.430  18.256  1.00 58.71      O
ATOM    973  N   ALA A 664     -34.229  59.684  19.178  1.00 59.88      N
ATOM    974  CA  ALA A 664     -35.313  59.294  20.080  1.00 61.29      C
ATOM    975  CB  ALA A 664     -34.937  58.043  20.869  1.00 61.03      C
ATOM    976  C   ALA A 664     -35.678  60.442  21.027  1.00 62.49      C
ATOM    977  O   ALA A 664     -36.843  60.809  21.136  1.00 62.76      O
ATOM    978  N   ARG A 665     -34.673  61.030  21.668  1.00 63.62      N
ATOM    979  CA  ARG A 665     -34.889  62.055  22.686  1.00 65.35      C
ATOM    980  CB  ARG A 665     -33.759  61.996  23.728  1.00 65.20      C
ATOM    981  CG  ARG A 665     -33.562  60.563  24.272  1.00 66.62      C
ATOM    982  CD  ARG A 665     -32.638  60.440  25.483  1.00 66.98      C
ATOM    983  NE  ARG A 665     -32.783  59.115  26.099  1.00 71.00      N
ATOM    984  CZ  ARG A 665     -33.306  58.880  27.307  1.00 72.94      C
ATOM    985  NH1 ARG A 665     -33.724  59.883  28.074  1.00 74.11      N
ATOM    986  NH2 ARG A 665     -33.403  57.631  27.759  1.00 73.49      N
ATOM    987  C   ARG A 665     -35.115  63.485  22.152  1.00 65.84      C
ATOM    988  O   ARG A 665     -35.423  64.392  22.925  1.00 66.29      O
ATOM    989  N   SER A 666     -34.990  63.687  20.841  1.00 66.49      N
ATOM    990  CA  SER A 666     -35.189  65.014  20.255  1.00 66.99      C
ATOM    991  CB  SER A 666     -34.366  65.173  18.974  1.00 67.10      C
ATOM    992  OG  SER A 666     -34.904  64.392  17.921  1.00 67.35      O
ATOM    993  C   SER A 666     -36.668  65.308  19.978  1.00 67.28      C
ATOM    994  O   SER A 666     -37.398  64.459  19.462  1.00 67.48      O
ATOM    995  N   ALA B 666       1.225  53.853  -0.387  1.00 65.58      N
ATOM    996  CA  ALA B 666       0.488  54.605   0.674  1.00 65.66      C
ATOM    997  CB  ALA B 666      -0.406  55.697   0.053  1.00 65.60      C
ATOM    998  C   ALA B 666      -0.340  53.659   1.554  1.00 65.56      C
ATOM    999  O   ALA B 666      -0.410  52.437   1.307  1.00 65.68      O
ATOM   1000  N   VAL B 667      -0.972  54.238   2.572  1.00 64.89      N
ATOM   1001  CA  VAL B 667      -1.725  53.477   3.563  1.00 63.96      C
ATOM   1002  CB  VAL B 667      -1.604  54.151   4.974  1.00 64.24      C
ATOM   1003  CG1 VAL B 667      -1.758  55.677   4.884  1.00 64.67      C
ATOM   1004  CG2 VAL B 667      -2.569  53.556   5.985  1.00 64.32      C
ATOM   1005  C   VAL B 667      -3.179  53.194   3.107  1.00 63.00      C
ATOM   1006  O   VAL B 667      -3.930  54.113   2.789  1.00 63.14      O
ATOM   1007  N   THR B 668      -3.541  51.908   3.065  1.00 61.88      N
ATOM   1008  CA  THR B 668      -4.889  51.438   2.700  1.00 60.86      C
```

FIG. 1S

```
ATOM   1009  CB   THR B 668      -4.931  49.889   2.501  1.00 61.01      C
ATOM   1010  OG1  THR B 668      -4.936  49.227   3.777  1.00 61.36      O
ATOM   1011  CG2  THR B 668      -3.746  49.392   1.648  1.00 61.18      C
ATOM   1012  C    THR B 668      -5.945  51.834   3.747  1.00 59.92      C
ATOM   1013  O    THR B 668      -5.583  52.262   4.853  1.00 60.02      O
ATOM   1014  N    PRO B 669      -7.256  51.705   3.401  1.00 58.97      N
ATOM   1015  CA   PRO B 669      -8.344  52.027   4.350  1.00 57.72      C
ATOM   1016  CB   PRO B 669      -9.616  51.685   3.552  1.00 57.86      C
ATOM   1017  CG   PRO B 669      -9.204  51.812   2.108  1.00 58.36      C
ATOM   1018  CD   PRO B 669      -7.799  51.272   2.093  1.00 59.19      C
ATOM   1019  C    PRO B 669      -8.281  51.216   5.654  1.00 56.21      C
ATOM   1020  O    PRO B 669      -8.362  51.798   6.741  1.00 55.60      O
ATOM   1021  N    GLU B 670      -8.125  49.893   5.534  1.00 55.02      N
ATOM   1022  CA   GLU B 670      -7.951  49.007   6.693  1.00 53.93      C
ATOM   1023  CB   GLU B 670      -7.709  47.546   6.262  1.00 54.08      C
ATOM   1024  CG   GLU B 670      -7.288  46.609   7.409  1.00 53.68      C
ATOM   1025  CD   GLU B 670      -7.574  45.129   7.159  1.00 53.89      C
ATOM   1026  OE1  GLU B 670      -8.733  44.777   6.871  1.00 54.58      O
ATOM   1027  OE2  GLU B 670      -6.645  44.307   7.287  1.00 52.17      O
ATOM   1028  C    GLU B 670      -6.837  49.526   7.613  1.00 53.40      C
ATOM   1029  O    GLU B 670      -7.028  49.613   8.824  1.00 52.89      O
ATOM   1030  N    GLU B 671      -5.713  49.929   7.014  1.00 52.68      N
ATOM   1031  CA   GLU B 671      -4.513  50.407   7.738  1.00 52.20      C
ATOM   1032  CB   GLU B 671      -3.325  50.538   6.778  1.00 51.90      C
ATOM   1033  CG   GLU B 671      -2.801  49.221   6.247  1.00 53.53      C
ATOM   1034  CD   GLU B 671      -1.686  49.412   5.228  1.00 53.54      C
ATOM   1035  OE1  GLU B 671      -1.687  50.433   4.505  1.00 53.49      O
ATOM   1036  OE2  GLU B 671      -0.803  48.534   5.166  1.00 56.41      O
ATOM   1037  C    GLU B 671      -4.664  51.722   8.509  1.00 51.04      C
ATOM   1038  O    GLU B 671      -4.245  51.816   9.662  1.00 50.35      O
ATOM   1039  N    ARG B 672      -5.209  52.748   7.862  1.00 50.05      N
ATOM   1040  CA   ARG B 672      -5.407  54.035   8.523  1.00 50.17      C
ATOM   1041  CB   ARG B 672      -5.932  55.060   7.520  1.00 50.46      C
ATOM   1042  CG   ARG B 672      -5.790  56.524   7.932  1.00 52.34      C
ATOM   1043  CD   ARG B 672      -6.712  57.439   7.063  1.00 53.91      C
ATOM   1044  NE   ARG B 672      -7.026  56.863   5.742  1.00 60.70      N
ATOM   1045  CZ   ARG B 672      -8.134  56.171   5.468  1.00 63.00      C
ATOM   1046  NH1  ARG B 672      -9.046  55.975   6.419  1.00 66.13      N
ATOM   1047  NH2  ARG B 672      -8.334  55.670   4.254  1.00 63.23      N
ATOM   1048  C    ARG B 672      -6.383  53.924   9.722  1.00 48.46      C
ATOM   1049  O    ARG B 672      -6.176  54.569  10.758  1.00 48.13      O
ATOM   1050  N    AHIS B 673     -7.419  53.107   9.580  0.50 47.60      N
ATOM   1051  N    BHIS B 673     -7.443  53.131   9.538  0.50 47.42      N
ATOM   1052  CA   AHIS B 673     -8.372  52.916  10.664  0.50 46.83      C
ATOM   1053  CA   BHIS B 673     -8.412  52.807  10.591  0.50 46.50      C
ATOM   1054  CB   AHIS B 673     -9.673  52.309  10.144  0.50 46.74      C
ATOM   1055  CB   BHIS B 673     -9.532  51.893  10.050  0.50 46.23      C
ATOM   1056  CG   AHIS B 673    -10.869  52.652  10.977  0.50 47.01      C
ATOM   1057  CG   BHIS B 673    -10.141  50.994  11.090  0.50 45.56      C
ATOM   1058  ND1  AHIS B 673    -11.666  53.748  10.720  0.50 47.01      N
ATOM   1059  ND1  BHIS B 673    -11.134  51.413  11.950  0.50 44.95      N
ATOM   1060  CE1  AHIS B 673    -12.641  53.796  11.608  0.50 45.75      C
ATOM   1061  CE1  BHIS B 673    -11.460  50.421  12.759  0.50 44.55      C
ATOM   1062  NE2  AHIS B 673    -12.500  52.778  12.437  0.50 45.39      N
ATOM   1063  NE2  BHIS B 673    -10.707  49.377  12.463  0.50 44.10      N
ATOM   1064  CD2  AHIS B 673    -11.401  52.046  12.064  0.50 46.02      C
```

FIG. 1T

| ATOM | 1065 | CD2 | BHIS | B | 673 | -9.883 | 49.705 | 11.415 | 0.50 | 45.21 | C |
| ATOM | 1066 | C | AHIS | B | 673 | -7.784 | 52.086 | 11.822 | 0.50 | 46.09 | C |
| ATOM | 1067 | C | BHIS | B | 673 | -7.719 | 52.143 | 11.785 | 0.50 | 45.90 | C |
| ATOM | 1068 | O | AHIS | B | 673 | -8.077 | 52.364 | 12.985 | 0.50 | 45.97 | O |
| ATOM | 1069 | O | BHIS | B | 673 | -7.880 | 52.584 | 12.925 | 0.50 | 45.75 | O |
| ATOM | 1070 | N | LEU | B | 674 | -6.957 | 51.085 | 11.506 | 1.00 | 45.34 | N |
| ATOM | 1071 | CA | LEU | B | 674 | -6.203 | 50.348 | 12.533 | 1.00 | 44.36 | C |
| ATOM | 1072 | CB | LEU | B | 674 | -5.363 | 49.217 | 11.926 | 1.00 | 44.47 | C |
| ATOM | 1073 | CG | LEU | B | 674 | -6.086 | 47.903 | 11.665 | 1.00 | 44.98 | C |
| ATOM | 1074 | CD1 | LEU | B | 674 | -5.247 | 46.985 | 10.756 | 1.00 | 46.09 | C |
| ATOM | 1075 | CD2 | LEU | B | 674 | -6.506 | 47.210 | 12.967 | 1.00 | 43.27 | C |
| ATOM | 1076 | C | LEU | B | 674 | -5.308 | 51.233 | 13.391 | 1.00 | 43.70 | C |
| ATOM | 1077 | O | LEU | B | 674 | -5.277 | 51.050 | 14.615 | 1.00 | 42.88 | O |
| ATOM | 1078 | N | SER | B | 675 | -4.599 | 52.190 | 12.766 | 1.00 | 42.73 | N |
| ATOM | 1079 | CA | SER | B | 675 | -3.688 | 53.088 | 13.510 | 1.00 | 42.48 | C |
| ATOM | 1080 | CB | SER | B | 675 | -2.776 | 53.908 | 12.575 | 1.00 | 42.69 | C |
| ATOM | 1081 | OG | SER | B | 675 | -2.086 | 53.063 | 11.680 | 1.00 | 44.63 | O |
| ATOM | 1082 | C | SER | B | 675 | -4.465 | 54.035 | 14.403 | 1.00 | 41.79 | C |
| ATOM | 1083 | O | SER | B | 675 | -4.031 | 54.341 | 15.518 | 1.00 | 41.72 | O |
| ATOM | 1084 | N | LYS | B | 676 | -5.589 | 54.528 | 13.892 | 1.00 | 40.60 | N |
| ATOM | 1085 | CA | LYS | B | 676 | -6.546 | 55.251 | 14.704 | 1.00 | 40.67 | C |
| ATOM | 1086 | CB | LYS | B | 676 | -7.776 | 55.651 | 13.895 | 1.00 | 40.82 | C |
| ATOM | 1087 | CG | LYS | B | 676 | -7.564 | 56.813 | 12.950 | 1.00 | 43.92 | C |
| ATOM | 1088 | CD | LYS | B | 676 | -8.591 | 56.754 | 11.818 | 1.00 | 48.32 | C |
| ATOM | 1089 | CE | LYS | B | 676 | -8.521 | 58.003 | 10.937 | 1.00 | 49.53 | C |
| ATOM | 1090 | NZ | LYS | B | 676 | -9.718 | 58.035 | 10.066 | 1.00 | 51.41 | N |
| ATOM | 1091 | C | LYS | B | 676 | -6.976 | 54.405 | 15.919 | 1.00 | 38.99 | C |
| ATOM | 1092 | O | LYS | B | 676 | -6.864 | 54.871 | 17.031 | 1.00 | 38.80 | O |
| ATOM | 1093 | N | MET | B | 677 | -7.457 | 53.186 | 15.684 | 1.00 | 38.65 | N |
| ATOM | 1094 | CA | MET | B | 677 | -7.936 | 52.289 | 16.751 | 1.00 | 38.76 | C |
| ATOM | 1095 | CB | MET | B | 677 | -8.474 | 50.974 | 16.180 | 1.00 | 39.11 | C |
| ATOM | 1096 | CG | MET | B | 677 | -9.877 | 51.008 | 15.578 | 1.00 | 41.20 | C |
| ATOM | 1097 | SD | MET | B | 677 | -11.199 | 51.559 | 16.698 | 1.00 | 46.43 | S |
| ATOM | 1098 | CE | MET | B | 677 | -11.046 | 53.329 | 16.520 | 1.00 | 38.54 | C |
| ATOM | 1099 | C | MET | B | 677 | -6.828 | 51.959 | 17.774 | 1.00 | 38.50 | C |
| ATOM | 1100 | O | MET | B | 677 | -7.104 | 51.852 | 18.975 | 1.00 | 38.07 | O |
| ATOM | 1101 | N | GLN | B | 678 | -5.592 | 51.806 | 17.286 | 1.00 | 37.59 | N |
| ATOM | 1102 | CA | GLN | B | 678 | -4.426 | 51.528 | 18.146 | 1.00 | 37.74 | C |
| ATOM | 1103 | CB | GLN | B | 678 | -3.272 | 50.955 | 17.343 | 1.00 | 36.77 | C |
| ATOM | 1104 | CG | GLN | B | 678 | -3.467 | 49.539 | 16.967 | 1.00 | 37.42 | C |
| ATOM | 1105 | CD | GLN | B | 678 | -2.370 | 49.023 | 16.043 | 1.00 | 39.76 | C |
| ATOM | 1106 | OE1 | GLN | B | 678 | -2.084 | 49.632 | 15.013 | 1.00 | 40.00 | O |
| ATOM | 1107 | NE2 | GLN | B | 678 | -1.777 | 47.886 | 16.395 | 1.00 | 36.02 | N |
| ATOM | 1108 | C | GLN | B | 678 | -3.971 | 52.742 | 18.919 | 1.00 | 38.08 | C |
| ATOM | 1109 | O | GLN | B | 678 | -3.667 | 52.654 | 20.111 | 1.00 | 37.64 | O |
| ATOM | 1110 | N | GLN | B | 679 | -3.951 | 53.892 | 18.261 | 1.00 | 39.31 | N |
| ATOM | 1111 | CA | GLN | B | 679 | -3.338 | 55.057 | 18.862 | 1.00 | 40.97 | C |
| ATOM | 1112 | CB | GLN | B | 679 | -2.799 | 56.019 | 17.784 | 1.00 | 41.08 | C |
| ATOM | 1113 | CG | GLN | B | 679 | -1.551 | 55.459 | 17.056 | 1.00 | 44.36 | C |
| ATOM | 1114 | CD | GLN | B | 679 | -0.947 | 56.441 | 16.060 | 1.00 | 45.39 | C |
| ATOM | 1115 | OE1 | GLN | B | 679 | -0.885 | 57.653 | 16.319 | 1.00 | 50.74 | O |
| ATOM | 1116 | NE2 | GLN | B | 679 | -0.506 | 55.923 | 14.906 | 1.00 | 50.17 | N |
| ATOM | 1117 | C | GLN | B | 679 | -4.267 | 55.769 | 19.827 | 1.00 | 39.93 | C |
| ATOM | 1118 | O | GLN | B | 679 | -3.828 | 56.230 | 20.884 | 1.00 | 39.76 | O |
| ATOM | 1119 | N | ASN | B | 680 | -5.542 | 55.868 | 19.456 | 1.00 | 39.25 | N |
| ATOM | 1120 | CA | ASN | B | 680 | -6.544 | 56.550 | 20.297 | 1.00 | 39.15 | C |

FIG. 1U

| ATOM | 1121 | CB  | ASN | B | 680 | -7.197  | 57.726 | 19.555 | 1.00 | 39.27 | C |
| ATOM | 1122 | CG  | ASN | B | 680 | -6.217  | 58.856 | 19.226 | 1.00 | 42.85 | C |
| ATOM | 1123 | OD1 | ASN | B | 680 | -6.120  | 59.269 | 18.061 | 1.00 | 44.52 | O |
| ATOM | 1124 | ND2 | ASN | B | 680 | -5.514  | 59.384 | 20.248 | 1.00 | 43.70 | N |
| ATOM | 1125 | C   | ASN | B | 680 | -7.670  | 55.663 | 20.803 | 1.00 | 37.92 | C |
| ATOM | 1126 | O   | ASN | B | 680 | -8.338  | 56.023 | 21.755 | 1.00 | 37.95 | O |
| ATOM | 1127 | N   | GLY | B | 681 | -7.894  | 54.533 | 20.151 | 1.00 | 37.43 | N |
| ATOM | 1128 | CA  | GLY | B | 681 | -9.135  | 53.797 | 20.289 | 1.00 | 36.89 | C |
| ATOM | 1129 | C   | GLY | B | 681 | -10.340 | 54.683 | 20.012 | 1.00 | 37.23 | C |
| ATOM | 1130 | O   | GLY | B | 681 | -10.218 | 55.770 | 19.410 | 1.00 | 36.49 | O |
| ATOM | 1131 | N   | TYR | B | 682 | -11.503 | 54.239 | 20.485 | 1.00 | 36.25 | N |
| ATOM | 1132 | CA  | TYR | B | 682 | -12.730 | 54.991 | 20.310 | 1.00 | 35.50 | C |
| ATOM | 1133 | CB  | TYR | B | 682 | -13.554 | 54.329 | 19.212 | 1.00 | 36.20 | C |
| ATOM | 1134 | CG  | TYR | B | 682 | -14.853 | 55.040 | 18.885 | 1.00 | 37.59 | C |
| ATOM | 1135 | CD1 | TYR | B | 682 | -14.844 | 56.251 | 18.182 | 1.00 | 35.51 | C |
| ATOM | 1136 | CE1 | TYR | B | 682 | -16.029 | 56.908 | 17.881 | 1.00 | 37.96 | C |
| ATOM | 1137 | CZ  | TYR | B | 682 | -17.248 | 56.359 | 18.264 | 1.00 | 38.04 | C |
| ATOM | 1138 | OH  | TYR | B | 682 | -18.407 | 57.048 | 17.941 | 1.00 | 39.89 | O |
| ATOM | 1139 | CE2 | TYR | B | 682 | -17.297 | 55.152 | 18.961 | 1.00 | 36.48 | C |
| ATOM | 1140 | CD2 | TYR | B | 682 | -16.094 | 54.498 | 19.272 | 1.00 | 37.34 | C |
| ATOM | 1141 | C   | TYR | B | 682 | -13.543 | 55.086 | 21.611 | 1.00 | 35.21 | C |
| ATOM | 1142 | O   | TYR | B | 682 | -13.916 | 54.061 | 22.184 | 1.00 | 33.25 | O |
| ATOM | 1143 | N   | GLU | B | 683 | -13.808 | 56.319 | 22.050 | 1.00 | 34.48 | N |
| ATOM | 1144 | CA  | GLU | B | 683 | -14.704 | 56.586 | 23.164 | 1.00 | 35.06 | C |
| ATOM | 1145 | CB  | GLU | B | 683 | -14.350 | 57.890 | 23.869 | 1.00 | 34.54 | C |
| ATOM | 1146 | CG  | GLU | B | 683 | -13.044 | 57.846 | 24.633 | 1.00 | 36.47 | C |
| ATOM | 1147 | CD  | GLU | B | 683 | -12.694 | 59.170 | 25.309 | 1.00 | 37.55 | C |
| ATOM | 1148 | OE1 | GLU | B | 683 | -13.594 | 59.990 | 25.533 | 1.00 | 40.87 | O |
| ATOM | 1149 | OE2 | GLU | B | 683 | -11.506 | 59.382 | 25.633 | 1.00 | 42.22 | O |
| ATOM | 1150 | C   | GLU | B | 683 | -16.159 | 56.653 | 22.681 | 1.00 | 33.89 | C |
| ATOM | 1151 | O   | GLU | B | 683 | -16.527 | 57.518 | 21.879 | 1.00 | 33.18 | O |
| ATOM | 1152 | N   | ASN | B | 684 | -16.981 | 55.743 | 23.195 | 1.00 | 32.67 | N |
| ATOM | 1153 | CA  | ASN | B | 684 | -18.372 | 55.638 | 22.773 | 1.00 | 32.47 | C |
| ATOM | 1154 | CB  | ASN | B | 684 | -18.979 | 54.350 | 23.335 | 1.00 | 32.18 | C |
| ATOM | 1155 | CG  | ASN | B | 684 | -20.423 | 54.128 | 22.910 | 1.00 | 32.70 | C |
| ATOM | 1156 | OD1 | ASN | B | 684 | -20.984 | 54.842 | 22.059 | 1.00 | 31.61 | O |
| ATOM | 1157 | ND2 | ASN | B | 684 | -21.026 | 53.125 | 23.492 | 1.00 | 29.58 | N |
| ATOM | 1158 | C   | ASN | B | 684 | -19.162 | 56.869 | 23.212 | 1.00 | 32.22 | C |
| ATOM | 1159 | O   | ASN | B | 684 | -19.304 | 57.123 | 24.398 | 1.00 | 31.99 | O |
| ATOM | 1160 | N   | PRO | B | 685 | -19.682 | 57.657 | 22.245 | 1.00 | 33.14 | N |
| ATOM | 1161 | CA  | PRO | B | 685 | -20.442 | 58.820 | 22.712 | 1.00 | 33.75 | C |
| ATOM | 1162 | CB  | PRO | B | 685 | -20.578 | 59.691 | 21.456 | 1.00 | 33.53 | C |
| ATOM | 1163 | CG  | PRO | B | 685 | -20.448 | 58.728 | 20.320 | 1.00 | 33.68 | C |
| ATOM | 1164 | CD  | PRO | B | 685 | -19.638 | 57.553 | 20.773 | 1.00 | 31.95 | C |
| ATOM | 1165 | C   | PRO | B | 685 | -21.816 | 58.432 | 23.286 | 1.00 | 35.06 | C |
| ATOM | 1166 | O   | PRO | B | 685 | -22.395 | 59.222 | 24.021 | 1.00 | 35.32 | O |
| ATOM | 1167 | N   | THR | B | 686 | -22.326 | 57.240 | 22.972 | 1.00 | 36.55 | N |
| ATOM | 1168 | CA  | THR | B | 686 | -23.607 | 56.792 | 23.568 | 1.00 | 38.52 | C |
| ATOM | 1169 | CB  | THR | B | 686 | -24.110 | 55.431 | 23.039 | 1.00 | 38.41 | C |
| ATOM | 1170 | OG1 | THR | B | 686 | -23.908 | 55.333 | 21.627 | 1.00 | 37.73 | O |
| ATOM | 1171 | CG2 | THR | B | 686 | -25.610 | 55.251 | 23.367 | 1.00 | 39.57 | C |
| ATOM | 1172 | C   | THR | B | 686 | -23.456 | 56.696 | 25.084 | 1.00 | 39.59 | C |
| ATOM | 1173 | O   | THR | B | 686 | -24.328 | 57.136 | 25.826 | 1.00 | 40.45 | O |
| ATOM | 1174 | N   | TYR | B | 687 | -22.334 | 56.146 | 25.539 | 1.00 | 41.10 | N |
| ATOM | 1175 | CA  | TYR | B | 687 | -21.999 | 56.100 | 26.969 | 1.00 | 42.62 | C |
| ATOM | 1176 | CB  | TYR | B | 687 | -20.670 | 55.372 | 27.208 | 1.00 | 41.94 | C |

FIG. 1V

```
ATOM   1177  CG   TYR B 687     -20.252  55.338  28.658  1.00 40.93      C
ATOM   1178  CD1  TYR B 687     -20.912  54.511  29.587  1.00 40.28      C
ATOM   1179  CE1  TYR B 687     -20.530  54.497  30.936  1.00 39.81      C
ATOM   1180  CZ   TYR B 687     -19.483  55.300  31.349  1.00 40.67      C
ATOM   1181  OH   TYR B 687     -19.080  55.309  32.664  1.00 42.63      O
ATOM   1182  CE2  TYR B 687     -18.818  56.118  30.442  1.00 41.31      C
ATOM   1183  CD2  TYR B 687     -19.213  56.139  29.111  1.00 38.42      C
ATOM   1184  C    TYR B 687     -21.997  57.450  27.661  1.00 44.98      C
ATOM   1185  O    TYR B 687     -22.670  57.631  28.677  1.00 44.81      O
ATOM   1186  N    LYS B 688     -21.225  58.389  27.122  1.00 47.87      N
ATOM   1187  CA   LYS B 688     -21.176  59.754  27.635  1.00 51.05      C
ATOM   1188  CB   LYS B 688     -20.130  60.562  26.876  1.00 51.25      C
ATOM   1189  CG   LYS B 688     -18.705  60.241  27.286  1.00 52.98      C
ATOM   1190  CD   LYS B 688     -17.713  61.142  26.571  1.00 56.42      C
ATOM   1191  CE   LYS B 688     -17.500  60.693  25.140  1.00 57.41      C
ATOM   1192  NZ   LYS B 688     -16.205  61.205  24.632  1.00 58.51      N
ATOM   1193  C    LYS B 688     -22.535  60.481  27.606  1.00 52.82      C
ATOM   1194  O    LYS B 688     -22.903  61.141  28.570  1.00 53.08      O
ATOM   1195  N    PHE B 689     -23.262  60.354  26.501  1.00 55.13      N
ATOM   1196  CA   PHE B 689     -24.617  60.887  26.372  1.00 57.54      C
ATOM   1197  CB   PHE B 689     -25.220  60.386  25.057  1.00 57.82      C
ATOM   1198  CG   PHE B 689     -26.669  60.727  24.866  1.00 59.24      C
ATOM   1199  CD1  PHE B 689     -27.083  62.055  24.768  1.00 60.86      C
ATOM   1200  CE1  PHE B 689     -28.431  62.374  24.573  1.00 62.18      C
ATOM   1201  CZ   PHE B 689     -29.371  61.351  24.455  1.00 61.27      C
ATOM   1202  CE2  PHE B 689     -28.959  60.013  24.540  1.00 61.96      C
ATOM   1203  CD2  PHE B 689     -27.616  59.713  24.737  1.00 60.39      C
ATOM   1204  C    PHE B 689     -25.511  60.521  27.580  1.00 58.93      C
ATOM   1205  O    PHE B 689     -26.025  61.409  28.270  1.00 59.07      O
ATOM   1206  N    PHE B 690     -25.667  59.223  27.842  1.00 60.60      N
ATOM   1207  CA   PHE B 690     -26.433  58.756  28.996  1.00 62.62      C
ATOM   1208  CB   PHE B 690     -26.725  57.255  28.900  1.00 62.08      C
ATOM   1209  CG   PHE B 690     -27.787  56.906  27.886  1.00 62.43      C
ATOM   1210  CD1  PHE B 690     -29.097  57.388  28.027  1.00 61.07      C
ATOM   1211  CE1  PHE B 690     -30.077  57.073  27.095  1.00 60.52      C
ATOM   1212  CZ   PHE B 690     -29.767  56.271  26.001  1.00 61.28      C
ATOM   1213  CE2  PHE B 690     -28.468  55.780  25.847  1.00 61.57      C
ATOM   1214  CD2  PHE B 690     -27.486  56.098  26.788  1.00 61.38      C
ATOM   1215  C    PHE B 690     -25.756  59.097  30.324  1.00 64.34      C
ATOM   1216  O    PHE B 690     -26.430  59.309  31.326  1.00 64.77      O
ATOM   1217  N    GLU B 691     -24.428  59.180  30.315  1.00 66.58      N
ATOM   1218  CA   GLU B 691     -23.649  59.495  31.514  1.00 68.67      C
ATOM   1219  CB   GLU B 691     -22.150  59.271  31.260  1.00 68.63      C
ATOM   1220  CG   GLU B 691     -21.258  59.362  32.491  1.00 68.58      C
ATOM   1221  CD   GLU B 691     -21.423  58.188  33.440  1.00 68.44      C
ATOM   1222  OE1  GLU B 691     -21.998  57.158  33.030  1.00 67.71      O
ATOM   1223  OE2  GLU B 691     -20.968  58.296  34.602  1.00 69.40      O
ATOM   1224  C    GLU B 691     -23.897  60.918  32.004  1.00 70.28      C
ATOM   1225  O    GLU B 691     -24.091  61.135  33.203  1.00 70.70      O
ATOM   1226  N    GLN B 692     -23.889  61.875  31.075  1.00 72.14      N
ATOM   1227  CA   GLN B 692     -24.149  63.286  31.384  1.00 73.95      C
ATOM   1228  CB   GLN B 692     -23.899  64.160  30.150  1.00 74.03      C
ATOM   1229  CG   GLN B 692     -22.432  64.537  29.972  1.00 75.57      C
ATOM   1230  CD   GLN B 692     -22.020  64.662  28.511  1.00 77.35      C
ATOM   1231  OE1  GLN B 692     -22.829  65.015  27.645  1.00 77.72      O
ATOM   1232  NE2  GLN B 692     -20.748  64.373  28.231  1.00 77.36      N
```

FIG. 1W

```
ATOM   1233  C   GLN B 692     -25.551  63.537  31.967  1.00 74.82    C
ATOM   1234  O   GLN B 692     -25.779  64.551  32.638  1.00 74.93    O
ATOM   1235  N   MET B 693     -26.474  62.609  31.708  1.00 75.75    N
ATOM   1236  CA  MET B 693     -27.773  62.578  32.380  1.00 76.94    C
ATOM   1237  CB  MET B 693     -28.791  61.807  31.538  1.00 76.76    C
ATOM   1238  CG  MET B 693     -29.344  62.566  30.345  1.00 77.33    C
ATOM   1239  SD  MET B 693     -30.058  61.464  29.091  1.00 78.84    S
ATOM   1240  CE  MET B 693     -31.129  60.396  30.074  1.00 78.90    C
ATOM   1241  C   MET B 693     -27.644  61.909  33.753  1.00 76.88    C
ATOM   1242  O   MET B 693     -27.585  62.577  34.788  1.00 77.12    O
```

FIG. 2A

```
ATOM    995  N    ALA B 666       1.225  53.853  -0.387  1.00 65.58           N
ATOM    996  CA   ALA B 666       0.488  54.605   0.674  1.00 65.66           C
ATOM    997  CB   ALA B 666      -0.406  55.697   0.053  1.00 65.60           C
ATOM    998  C    ALA B 666      -0.340  53.659   1.554  1.00 65.56           C
ATOM    999  O    ALA B 666      -0.410  52.437   1.307  1.00 65.68           O
ATOM   1000  N    VAL B 667      -0.972  54.238   2.572  1.00 64.89           N
ATOM   1001  CA   VAL B 667      -1.725  53.477   3.563  1.00 63.96           C
ATOM   1002  CB   VAL B 667      -1.604  54.151   4.974  1.00 64.24           C
ATOM   1003  CG1  VAL B 667      -1.758  55.677   4.884  1.00 64.67           C
ATOM   1004  CG2  VAL B 667      -2.569  53.556   5.985  1.00 64.32           C
ATOM   1005  C    VAL B 667      -3.179  53.194   3.107  1.00 63.00           C
ATOM   1006  O    VAL B 667      -3.930  54.113   2.789  1.00 63.14           O
ATOM   1007  N    THR B 668      -3.541  51.908   3.065  1.00 61.88           N
ATOM   1008  CA   THR B 668      -4.889  51.438   2.700  1.00 60.86           C
ATOM   1009  CB   THR B 668      -4.931  49.889   2.501  1.00 61.01           C
ATOM   1010  OG1  THR B 668      -4.936  49.227   3.777  1.00 61.36           O
ATOM   1011  CG2  THR B 668      -3.746  49.392   1.648  1.00 61.18           C
ATOM   1012  C    THR B 668      -5.945  51.834   3.747  1.00 59.92           C
ATOM   1013  O    THR B 668      -5.583  52.262   4.853  1.00 60.02           O
ATOM   1014  N    PRO B 669      -7.256  51.705   3.401  1.00 58.97           N
ATOM   1015  CA   PRO B 669      -8.344  52.027   4.350  1.00 57.72           C
ATOM   1016  CB   PRO B 669      -9.616  51.685   3.552  1.00 57.86           C
ATOM   1017  CG   PRO B 669      -9.204  51.812   2.108  1.00 58.36           C
ATOM   1018  CD   PRO B 669      -7.799  51.272   2.093  1.00 59.19           C
ATOM   1019  C    PRO B 669      -8.281  51.216   5.654  1.00 56.21           C
ATOM   1020  O    PRO B 669      -8.362  51.798   6.741  1.00 55.60           O
ATOM   1021  N    GLU B 670      -8.125  49.893   5.534  1.00 55.02           N
ATOM   1022  CA   GLU B 670      -7.951  49.007   6.693  1.00 53.93           C
ATOM   1023  CB   GLU B 670      -7.709  47.546   6.262  1.00 54.08           C
ATOM   1024  CG   GLU B 670      -7.288  46.609   7.409  1.00 53.68           C
ATOM   1025  CD   GLU B 670      -7.574  45.129   7.159  1.00 53.89           C
ATOM   1026  OE1  GLU B 670      -8.733  44.777   6.871  1.00 54.58           O
ATOM   1027  OE2  GLU B 670      -6.645  44.307   7.287  1.00 52.17           O
ATOM   1028  C    GLU B 670      -6.837  49.526   7.613  1.00 53.40           C
ATOM   1029  O    GLU B 670      -7.028  49.613   8.824  1.00 52.89           O
ATOM   1030  N    GLU B 671      -5.713  49.929   7.014  1.00 52.68           N
ATOM   1031  CA   GLU B 671      -4.513  50.407   7.738  1.00 52.20           C
ATOM   1032  CB   GLU B 671      -3.325  50.538   6.778  1.00 51.90           C
ATOM   1033  CG   GLU B 671      -2.801  49.221   6.247  1.00 53.53           C
ATOM   1034  CD   GLU B 671      -1.686  49.412   5.228  1.00 53.54           C
ATOM   1035  OE1  GLU B 671      -1.687  50.433   4.505  1.00 53.49           O
ATOM   1036  OE2  GLU B 671      -0.803  48.534   5.166  1.00 56.41           O
ATOM   1037  C    GLU B 671      -4.664  51.722   8.509  1.00 51.04           C
ATOM   1038  O    GLU B 671      -4.245  51.816   9.662  1.00 50.35           O
ATOM   1039  N    ARG B 672      -5.209  52.748   7.862  1.00 50.05           N
ATOM   1040  CA   ARG B 672      -5.407  54.035   8.523  1.00 50.17           C
ATOM   1041  CB   ARG B 672      -5.932  55.060   7.520  1.00 50.46           C
ATOM   1042  CG   ARG B 672      -5.790  56.524   7.932  1.00 52.34           C
ATOM   1043  CD   ARG B 672      -6.712  57.439   7.063  1.00 53.91           C
ATOM   1044  NE   ARG B 672      -7.026  56.863   5.742  1.00 60.70           N
ATOM   1045  CZ   ARG B 672      -8.134  56.171   5.468  1.00 63.00           C
ATOM   1046  NH1  ARG B 672      -9.046  55.975   6.419  1.00 66.13           N
ATOM   1047  NH2  ARG B 672      -8.334  55.670   4.254  1.00 63.23           N
ATOM   1048  C    ARG B 672      -6.383  53.924   9.722  1.00 48.46           C
ATOM   1049  O    ARG B 672      -6.176  54.569  10.758  1.00 48.13           O
ATOM   1050  N   AHIS B 673      -7.419  53.107   9.580  0.50 47.60           N
```

FIG. 2B

```
ATOM   1051  N   BHIS B 673      -7.443  53.131   9.538  0.50 47.42       N
ATOM   1052  CA  AHIS B 673      -8.372  52.916  10.664  0.50 46.83       C
ATOM   1053  CA  BHIS B 673      -8.412  52.807  10.591  0.50 46.50       C
ATOM   1054  CB  AHIS B 673      -9.673  52.309  10.144  0.50 46.74       C
ATOM   1055  CB  BHIS B 673      -9.532  51.893  10.050  0.50 46.23       C
ATOM   1056  CG  AHIS B 673     -10.869  52.652  10.977  0.50 47.01       C
ATOM   1057  CG  BHIS B 673     -10.141  50.994  11.090  0.50 45.56       C
ATOM   1058  ND1 AHIS B 673     -11.666  53.748  10.720  0.50 47.01       N
ATOM   1059  ND1 BHIS B 673     -11.134  51.413  11.950  0.50 44.95       N
ATOM   1060  CE1 AHIS B 673     -12.641  53.796  11.608  0.50 45.75       C
ATOM   1061  CE1 BHIS B 673     -11.460  50.421  12.759  0.50 44.55       C
ATOM   1062  NE2 AHIS B 673     -12.500  52.778  12.437  0.50 45.39       N
ATOM   1063  NE2 BHIS B 673     -10.707  49.377  12.463  0.50 44.10       N
ATOM   1064  CD2 AHIS B 673     -11.401  52.046  12.064  0.50 46.02       C
ATOM   1065  CD2 BHIS B 673      -9.883  49.705  11.415  0.50 45.21       C
ATOM   1066  C   AHIS B 673      -7.784  52.086  11.822  0.50 46.09       C
ATOM   1067  C   BHIS B 673      -7.719  52.143  11.785  0.50 45.90       C
ATOM   1068  O   AHIS B 673      -8.077  52.364  12.985  0.50 45.97       O
ATOM   1069  O   BHIS B 673      -7.880  52.584  12.925  0.50 45.75       O
ATOM   1070  N   LEU  B 674      -6.957  51.085  11.506  1.00 45.34       N
ATOM   1071  CA  LEU  B 674      -6.203  50.348  12.533  1.00 44.36       C
ATOM   1072  CB  LEU  B 674      -5.363  49.217  11.926  1.00 44.47       C
ATOM   1073  CG  LEU  B 674      -6.086  47.903  11.665  1.00 44.98       C
ATOM   1074  CD1 LEU  B 674      -5.247  46.985  10.756  1.00 46.09       C
ATOM   1075  CD2 LEU  B 674      -6.506  47.210  12.967  1.00 43.27       C
ATOM   1076  C   LEU  B 674      -5.308  51.233  13.391  1.00 43.70       C
ATOM   1077  O   LEU  B 674      -5.277  51.050  14.615  1.00 42.88       O
ATOM   1078  N   SER  B 675      -4.599  52.190  12.766  1.00 42.73       N
ATOM   1079  CA  SER  B 675      -3.688  53.088  13.510  1.00 42.48       C
ATOM   1080  CB  SER  B 675      -2.776  53.908  12.575  1.00 42.69       C
ATOM   1081  OG  SER  B 675      -2.086  53.063  11.680  1.00 44.63       O
ATOM   1082  C   SER  B 675      -4.465  54.035  14.403  1.00 41.79       C
ATOM   1083  O   SER  B 675      -4.031  54.341  15.518  1.00 41.72       O
ATOM   1084  N   LYS  B 676      -5.589  54.528  13.892  1.00 40.60       N
ATOM   1085  CA  LYS  B 676      -6.546  55.251  14.704  1.00 40.67       C
ATOM   1086  CB  LYS  B 676      -7.776  55.651  13.895  1.00 40.82       C
ATOM   1087  CG  LYS  B 676      -7.564  56.813  12.950  1.00 43.92       C
ATOM   1088  CD  LYS  B 676      -8.591  56.754  11.818  1.00 48.32       C
ATOM   1089  CE  LYS  B 676      -8.521  58.003  10.937  1.00 49.53       C
ATOM   1090  NZ  LYS  B 676      -9.718  58.035  10.066  1.00 51.41       N
ATOM   1091  C   LYS  B 676      -6.976  54.405  15.919  1.00 38.99       C
ATOM   1092  O   LYS  B 676      -6.864  54.871  17.031  1.00 38.80       O
ATOM   1093  N   MET  B 677      -7.457  53.186  15.684  1.00 38.65       N
ATOM   1094  CA  MET  B 677      -7.936  52.289  16.751  1.00 38.76       C
ATOM   1095  CB  MET  B 677      -8.474  50.974  16.180  1.00 39.11       C
ATOM   1096  CG  MET  B 677      -9.877  51.008  15.578  1.00 41.20       C
ATOM   1097  SD  MET  B 677     -11.199  51.559  16.698  1.00 46.43       S
ATOM   1098  CE  MET  B 677     -11.046  53.329  16.520  1.00 38.54       C
ATOM   1099  C   MET  B 677      -6.828  51.959  17.774  1.00 38.50       C
ATOM   1100  O   MET  B 677      -7.104  51.852  18.975  1.00 38.07       O
ATOM   1101  N   GLN  B 678      -5.592  51.806  17.286  1.00 37.59       N
ATOM   1102  CA  GLN  B 678      -4.426  51.528  18.146  1.00 37.74       C
ATOM   1103  CB  GLN  B 678      -3.272  50.955  17.343  1.00 36.77       C
ATOM   1104  CG  GLN  B 678      -3.467  49.539  16.967  1.00 37.42       C
ATOM   1105  CD  GLN  B 678      -2.370  49.023  16.043  1.00 39.76       C
ATOM   1106  OE1 GLN  B 678      -2.084  49.632  15.013  1.00 40.00       O
```

FIG. 2C

```
ATOM   1107  NE2 GLN B 678      -1.777  47.886  16.395  1.00 36.02      N
ATOM   1108  C   GLN B 678      -3.971  52.742  18.919  1.00 38.08      C
ATOM   1109  O   GLN B 678      -3.667  52.654  20.111  1.00 37.64      O
ATOM   1110  N   GLN B 679      -3.951  53.892  18.261  1.00 39.31      N
ATOM   1111  CA  GLN B 679      -3.338  55.057  18.862  1.00 40.97      C
ATOM   1112  CB  GLN B 679      -2.799  56.019  17.784  1.00 41.08      C
ATOM   1113  CG  GLN B 679      -1.551  55.459  17.056  1.00 44.36      C
ATOM   1114  CD  GLN B 679      -0.947  56.441  16.060  1.00 45.39      C
ATOM   1115  OE1 GLN B 679      -0.885  57.653  16.319  1.00 50.74      O
ATOM   1116  NE2 GLN B 679      -0.506  55.923  14.906  1.00 50.17      N
ATOM   1117  C   GLN B 679      -4.267  55.769  19.827  1.00 39.93      C
ATOM   1118  O   GLN B 679      -3.828  56.230  20.884  1.00 39.76      O
ATOM   1119  N   ASN B 680      -5.542  55.868  19.456  1.00 39.25      N
ATOM   1120  CA  ASN B 680      -6.544  56.550  20.297  1.00 39.15      C
ATOM   1121  CB  ASN B 680      -7.197  57.726  19.555  1.00 39.27      C
ATOM   1122  CG  ASN B 680      -6.217  58.856  19.226  1.00 42.85      C
ATOM   1123  OD1 ASN B 680      -6.120  59.269  18.061  1.00 44.52      O
ATOM   1124  ND2 ASN B 680      -5.514  59.384  20.248  1.00 43.70      N
ATOM   1125  C   ASN B 680      -7.670  55.663  20.803  1.00 37.92      C
ATOM   1126  O   ASN B 680      -8.338  56.023  21.755  1.00 37.95      O
ATOM   1127  N   GLY B 681      -7.894  54.533  20.151  1.00 37.43      N
ATOM   1128  CA  GLY B 681      -9.135  53.797  20.289  1.00 36.89      C
ATOM   1129  C   GLY B 681     -10.340  54.683  20.012  1.00 37.23      C
ATOM   1130  O   GLY B 681     -10.218  55.770  19.410  1.00 36.49      O
ATOM   1131  N   TYR B 682     -11.503  54.239  20.485  1.00 36.25      N
ATOM   1132  CA  TYR B 682     -12.730  54.991  20.310  1.00 35.50      C
ATOM   1133  CB  TYR B 682     -13.554  54.329  19.212  1.00 36.20      C
ATOM   1134  CG  TYR B 682     -14.853  55.040  18.885  1.00 37.59      C
ATOM   1135  CD1 TYR B 682     -14.844  56.251  18.182  1.00 35.51      C
ATOM   1136  CE1 TYR B 682     -16.029  56.908  17.881  1.00 37.96      C
ATOM   1137  CZ  TYR B 682     -17.248  56.359  18.264  1.00 38.04      C
ATOM   1138  OH  TYR B 682     -18.407  57.048  17.941  1.00 39.89      O
ATOM   1139  CE2 TYR B 682     -17.297  55.152  18.961  1.00 36.48      C
ATOM   1140  CD2 TYR B 682     -16.094  54.498  19.272  1.00 37.34      C
ATOM   1141  C   TYR B 682     -13.543  55.086  21.611  1.00 35.21      C
ATOM   1142  O   TYR B 682     -13.916  54.061  22.184  1.00 33.25      O
ATOM   1143  N   GLU B 683     -13.808  56.319  22.050  1.00 34.48      N
ATOM   1144  CA  GLU B 683     -14.704  56.586  23.164  1.00 35.06      C
ATOM   1145  CB  GLU B 683     -14.350  57.890  23.869  1.00 34.54      C
ATOM   1146  CG  GLU B 683     -13.044  57.846  24.633  1.00 36.47      C
ATOM   1147  CD  GLU B 683     -12.694  59.170  25.309  1.00 37.55      C
ATOM   1148  OE1 GLU B 683     -13.594  59.990  25.533  1.00 40.87      O
ATOM   1149  OE2 GLU B 683     -11.506  59.382  25.633  1.00 42.22      O
ATOM   1150  C   GLU B 683     -16.159  56.653  22.681  1.00 33.89      C
ATOM   1151  O   GLU B 683     -16.527  57.518  21.879  1.00 33.18      O
ATOM   1152  N   ASN B 684     -16.981  55.743  23.195  1.00 32.67      N
ATOM   1153  CA  ASN B 684     -18.372  55.638  22.773  1.00 32.47      C
ATOM   1154  CB  ASN B 684     -18.979  54.350  23.335  1.00 32.18      C
ATOM   1155  CG  ASN B 684     -20.423  54.128  22.910  1.00 32.70      C
ATOM   1156  OD1 ASN B 684     -20.984  54.842  22.059  1.00 31.61      O
ATOM   1157  ND2 ASN B 684     -21.026  53.125  23.492  1.00 29.58      N
ATOM   1158  C   ASN B 684     -19.162  56.869  23.212  1.00 32.22      C
ATOM   1159  O   ASN B 684     -19.304  57.123  24.398  1.00 31.99      O
ATOM   1160  N   PRO B 685     -19.682  57.657  22.245  1.00 33.14      N
ATOM   1161  CA  PRO B 685     -20.442  58.820  22.712  1.00 33.75      C
ATOM   1162  CB  PRO B 685     -20.578  59.691  21.456  1.00 33.53      C
```

FIG. 2D

```
ATOM   1163  CG   PRO B 685     -20.448  58.728  20.320  1.00 33.68    C
ATOM   1164  CD   PRO B 685     -19.638  57.553  20.773  1.00 31.95    C
ATOM   1165  C    PRO B 685     -21.816  58.432  23.286  1.00 35.06    C
ATOM   1166  O    PRO B 685     -22.395  59.222  24.021  1.00 35.32    O
ATOM   1167  N    THR B 686     -22.326  57.240  22.972  1.00 36.55    N
ATOM   1168  CA   THR B 686     -23.607  56.792  23.568  1.00 38.52    C
ATOM   1169  CB   THR B 686     -24.110  55.431  23.039  1.00 38.41    C
ATOM   1170  OG1  THR B 686     -23.908  55.333  21.627  1.00 37.73    O
ATOM   1171  CG2  THR B 686     -25.610  55.251  23.367  1.00 39.57    C
ATOM   1172  C    THR B 686     -23.456  56.696  25.084  1.00 39.59    C
ATOM   1173  O    THR B 686     -24.328  57.136  25.826  1.00 40.45    O
ATOM   1174  N    TYR B 687     -22.334  56.146  25.539  1.00 41.10    N
ATOM   1175  CA   TYR B 687     -21.999  56.100  26.969  1.00 42.62    C
ATOM   1176  CB   TYR B 687     -20.670  55.372  27.208  1.00 41.94    C
ATOM   1177  CG   TYR B 687     -20.252  55.338  28.658  1.00 40.93    C
ATOM   1178  CD1  TYR B 687     -20.912  54.511  29.587  1.00 40.28    C
ATOM   1179  CE1  TYR B 687     -20.530  54.497  30.936  1.00 39.81    C
ATOM   1180  CZ   TYR B 687     -19.483  55.300  31.349  1.00 40.67    C
ATOM   1181  OH   TYR B 687     -19.080  55.309  32.664  1.00 42.63    O
ATOM   1182  CE2  TYR B 687     -18.818  56.118  30.442  1.00 41.31    C
ATOM   1183  CD2  TYR B 687     -19.213  56.139  29.111  1.00 38.42    C
ATOM   1184  C    TYR B 687     -21.997  57.450  27.661  1.00 44.98    C
ATOM   1185  O    TYR B 687     -22.670  57.631  28.677  1.00 44.81    O
ATOM   1186  N    LYS B 688     -21.225  58.389  27.122  1.00 47.87    N
ATOM   1187  CA   LYS B 688     -21.176  59.754  27.635  1.00 51.05    C
ATOM   1188  CB   LYS B 688     -20.130  60.562  26.876  1.00 51.25    C
ATOM   1189  CG   LYS B 688     -18.705  60.241  27.286  1.00 52.98    C
ATOM   1190  CD   LYS B 688     -17.713  61.142  26.571  1.00 56.42    C
ATOM   1191  CE   LYS B 688     -17.500  60.693  25.140  1.00 57.41    C
ATOM   1192  NZ   LYS B 688     -16.205  61.205  24.632  1.00 58.51    N
ATOM   1193  C    LYS B 688     -22.535  60.481  27.606  1.00 52.82    C
ATOM   1194  O    LYS B 688     -22.903  61.141  28.570  1.00 53.08    O
ATOM   1195  N    PHE B 689     -23.262  60.354  26.501  1.00 55.13    N
ATOM   1196  CA   PHE B 689     -24.617  60.887  26.372  1.00 57.54    C
ATOM   1197  CB   PHE B 689     -25.220  60.386  25.057  1.00 57.82    C
ATOM   1198  CG   PHE B 689     -26.669  60.727  24.866  1.00 59.24    C
ATOM   1199  CD1  PHE B 689     -27.083  62.055  24.768  1.00 60.86    C
ATOM   1200  CE1  PHE B 689     -28.431  62.374  24.573  1.00 62.18    C
ATOM   1201  CZ   PHE B 689     -29.371  61.351  24.455  1.00 61.27    C
ATOM   1202  CE2  PHE B 689     -28.959  60.013  24.540  1.00 61.96    C
ATOM   1203  CD2  PHE B 689     -27.616  59.713  24.737  1.00 60.39    C
ATOM   1204  C    PHE B 689     -25.511  60.521  27.580  1.00 58.93    C
ATOM   1205  O    PHE B 689     -26.025  61.409  28.270  1.00 59.07    O
ATOM   1206  N    PHE B 690     -25.667  59.223  27.842  1.00 60.60    N
ATOM   1207  CA   PHE B 690     -26.433  58.756  28.996  1.00 62.62    C
ATOM   1208  CB   PHE B 690     -26.725  57.255  28.900  1.00 62.08    C
ATOM   1209  CG   PHE B 690     -27.787  56.906  27.886  1.00 62.43    C
ATOM   1210  CD1  PHE B 690     -29.097  57.388  28.027  1.00 61.07    C
ATOM   1211  CE1  PHE B 690     -30.077  57.073  27.095  1.00 60.52    C
ATOM   1212  CZ   PHE B 690     -29.767  56.271  26.001  1.00 61.28    C
ATOM   1213  CE2  PHE B 690     -28.468  55.780  25.847  1.00 61.57    C
ATOM   1214  CD2  PHE B 690     -27.486  56.098  26.788  1.00 61.38    C
ATOM   1215  C    PHE B 690     -25.756  59.097  30.324  1.00 64.34    C
ATOM   1216  O    PHE B 690     -26.430  59.309  31.326  1.00 64.77    O
ATOM   1217  N    GLU B 691     -24.428  59.180  30.315  1.00 66.58    N
ATOM   1218  CA   GLU B 691     -23.649  59.495  31.514  1.00 68.67    C
```

FIG. 2E

```
ATOM   1219  CB   GLU B 691     -22.150  59.271  31.260  1.00 68.63       C
ATOM   1220  CG   GLU B 691     -21.258  59.362  32.491  1.00 68.58       C
ATOM   1221  CD   GLU B 691     -21.423  58.188  33.440  1.00 68.44       C
ATOM   1222  OE1  GLU B 691     -21.998  57.158  33.030  1.00 67.71       O
ATOM   1223  OE2  GLU B 691     -20.968  58.296  34.602  1.00 69.40       O
ATOM   1224  C    GLU B 691     -23.897  60.918  32.004  1.00 70.28       C
ATOM   1225  O    GLU B 691     -24.091  61.135  33.203  1.00 70.70       O
ATOM   1226  N    GLN B 692     -23.889  61.875  31.075  1.00 72.14       N
ATOM   1227  CA   GLN B 692     -24.149  63.286  31.384  1.00 73.95       C
ATOM   1228  CB   GLN B 692     -23.899  64.160  30.150  1.00 74.03       C
ATOM   1229  CG   GLN B 692     -22.432  64.537  29.972  1.00 75.57       C
ATOM   1230  CD   GLN B 692     -22.020  64.662  28.511  1.00 77.35       C
ATOM   1231  OE1  GLN B 692     -22.829  65.015  27.645  1.00 77.72       O
ATOM   1232  NE2  GLN B 692     -20.748  64.373  28.231  1.00 77.36       N
ATOM   1233  C    GLN B 692     -25.551  63.537  31.967  1.00 74.82       C
ATOM   1234  O    GLN B 692     -25.779  64.551  32.638  1.00 74.93       O
ATOM   1235  N    MET B 693     -26.474  62.609  31.708  1.00 75.75       N
ATOM   1236  CA   MET B 693     -27.773  62.578  32.380  1.00 76.94       C
ATOM   1237  CB   MET B 693     -28.791  61.807  31.538  1.00 76.76       C
ATOM   1238  CG   MET B 693     -29.344  62.566  30.345  1.00 77.33       C
ATOM   1239  SD   MET B 693     -30.058  61.464  29.091  1.00 78.84       S
ATOM   1240  CE   MET B 693     -31.129  60.396  30.074  1.00 78.90       C
ATOM   1241  C    MET B 693     -27.644  61.909  33.753  1.00 76.88       C
ATOM   1242  O    MET B 693     -27.585  62.577  34.788  1.00 77.12       O
```

FIG. 3A

| ATOM | 1 | N | ASN A 537 | -32.304 | 41.221 | 14.150 | 1.00 | 78.74 | N |
|---|---|---|---|---|---|---|---|---|---|
| ATOM | 2 | CA | ASN A 537 | -31.307 | 41.137 | 15.255 | 1.00 | 78.67 | C |
| ATOM | 3 | CB | ASN A 537 | -31.217 | 39.693 | 15.780 | 1.00 | 78.93 | C |
| ATOM | 4 | CG | ASN A 537 | -30.612 | 39.603 | 17.188 | 1.00 | 79.49 | C |
| ATOM | 5 | OD1 | ASN A 537 | -30.370 | 40.619 | 17.855 | 1.00 | 78.67 | O |
| ATOM | 6 | ND2 | ASN A 537 | -30.378 | 38.370 | 17.646 | 1.00 | 79.49 | N |
| ATOM | 7 | C | ASN A 537 | -29.933 | 41.684 | 14.825 | 1.00 | 78.35 | C |
| ATOM | 8 | O | ASN A 537 | -29.760 | 42.900 | 14.724 | 1.00 | 78.34 | O |
| ATOM | 9 | N | GLU A 538 | -28.976 | 40.797 | 14.544 | 1.00 | 77.88 | N |
| ATOM | 10 | CA | GLU A 538 | -27.595 | 41.205 | 14.229 | 1.00 | 77.61 | C |
| ATOM | 11 | CB | GLU A 538 | -26.664 | 39.990 | 14.117 | 1.00 | 77.49 | C |
| ATOM | 12 | CG | GLU A 538 | -27.182 | 38.857 | 13.247 | 1.00 | 78.01 | C |
| ATOM | 13 | CD | GLU A 538 | -26.174 | 37.732 | 13.083 | 1.00 | 78.55 | C |
| ATOM | 14 | OE1 | GLU A 538 | -25.446 | 37.434 | 14.057 | 1.00 | 80.12 | O |
| ATOM | 15 | OE2 | GLU A 538 | -26.111 | 37.140 | 11.977 | 1.00 | 79.77 | O |
| ATOM | 16 | C | GLU A 538 | -27.475 | 42.094 | 12.987 | 1.00 | 76.92 | C |
| ATOM | 17 | O | GLU A 538 | -28.288 | 41.999 | 12.065 | 1.00 | 77.13 | O |
| ATOM | 18 | N | LEU A 539 | -26.462 | 42.958 | 12.981 | 1.00 | 76.04 | N |
| ATOM | 19 | CA | LEU A 539 | -26.189 | 43.845 | 11.844 | 1.00 | 75.21 | C |
| ATOM | 20 | CB | LEU A 539 | -25.511 | 45.140 | 12.309 | 1.00 | 74.91 | C |
| ATOM | 21 | CG | LEU A 539 | -26.314 | 46.051 | 13.242 | 1.00 | 74.03 | C |
| ATOM | 22 | CD1 | LEU A 539 | -25.386 | 46.896 | 14.098 | 1.00 | 73.66 | C |
| ATOM | 23 | CD2 | LEU A 539 | -27.305 | 46.922 | 12.469 | 1.00 | 73.24 | C |
| ATOM | 24 | C | LEU A 539 | -25.329 | 43.150 | 10.787 | 1.00 | 74.81 | C |
| ATOM | 25 | O | LEU A 539 | -25.489 | 43.390 | 9.586 | 1.00 | 74.83 | O |
| ATOM | 26 | N | VAL A 540 | -24.412 | 42.303 | 11.248 | 1.00 | 74.07 | N |
| ATOM | 27 | CA | VAL A 540 | -23.548 | 41.517 | 10.369 | 1.00 | 73.43 | C |
| ATOM | 28 | CB | VAL A 540 | -22.143 | 42.192 | 10.114 | 1.00 | 73.43 | C |
| ATOM | 29 | CG1 | VAL A 540 | -22.288 | 43.531 | 9.383 | 1.00 | 72.79 | C |
| ATOM | 30 | CG2 | VAL A 540 | -21.347 | 42.364 | 11.421 | 1.00 | 73.08 | C |
| ATOM | 31 | C | VAL A 540 | -23.363 | 40.115 | 10.960 | 1.00 | 73.06 | C |
| ATOM | 32 | O | VAL A 540 | -23.564 | 39.909 | 12.172 | 1.00 | 73.08 | O |
| ATOM | 33 | N | GLN A 541 | -22.978 | 39.168 | 10.101 | 1.00 | 72.21 | N |
| ATOM | 34 | CA | GLN A 541 | -22.697 | 37.792 | 10.519 | 1.00 | 71.60 | C |
| ATOM | 35 | CB | GLN A 541 | -22.368 | 36.904 | 9.313 | 1.00 | 71.71 | C |
| ATOM | 36 | CG | GLN A 541 | -23.447 | 36.870 | 8.212 | 1.00 | 72.07 | C |
| ATOM | 37 | CD | GLN A 541 | -23.066 | 35.991 | 7.010 | 1.00 | 72.65 | C |
| ATOM | 38 | OE1 | GLN A 541 | -23.864 | 35.821 | 6.080 | 1.00 | 73.58 | O |
| ATOM | 39 | NE2 | GLN A 541 | -21.846 | 35.433 | 7.025 | 1.00 | 72.47 | N |
| ATOM | 40 | C | GLN A 541 | -21.561 | 37.741 | 11.553 | 1.00 | 70.53 | C |
| ATOM | 41 | O | GLN A 541 | -20.613 | 38.542 | 11.504 | 1.00 | 70.61 | O |
| ATOM | 42 | N | LYS A 542 | -21.681 | 36.797 | 12.485 | 1.00 | 68.91 | N |
| ATOM | 43 | CA | LYS A 542 | -20.777 | 36.667 | 13.625 | 1.00 | 67.25 | C |
| ATOM | 44 | CB | LYS A 542 | -21.237 | 35.502 | 14.508 | 1.00 | 67.40 | C |
| ATOM | 45 | CG | LYS A 542 | -22.687 | 35.636 | 14.958 | 1.00 | 68.27 | C |
| ATOM | 46 | CD | LYS A 542 | -23.336 | 34.299 | 15.297 | 1.00 | 69.20 | C |
| ATOM | 47 | CE | LYS A 542 | -24.813 | 34.485 | 15.624 | 1.00 | 69.75 | C |
| ATOM | 48 | NZ | LYS A 542 | -25.297 | 33.470 | 16.595 | 1.00 | 69.61 | N |
| ATOM | 49 | C | LYS A 542 | -19.301 | 36.508 | 13.223 | 1.00 | 66.00 | C |
| ATOM | 50 | O | LYS A 542 | -18.973 | 35.916 | 12.181 | 1.00 | 66.06 | O |
| ATOM | 51 | N | PHE A 543 | -18.429 | 37.052 | 14.067 | 1.00 | 64.00 | N |
| ATOM | 52 | CA | PHE A 543 | -16.978 | 37.056 | 13.861 | 1.00 | 61.98 | C |
| ATOM | 53 | CB | PHE A 543 | -16.390 | 38.368 | 14.377 | 1.00 | 60.59 | C |
| ATOM | 54 | CG | PHE A 543 | -16.868 | 39.559 | 13.622 | 1.00 | 59.01 | C |
| ATOM | 55 | CD1 | PHE A 543 | -16.214 | 39.968 | 12.467 | 1.00 | 57.47 | C |
| ATOM | 56 | CE1 | PHE A 543 | -16.671 | 41.058 | 11.754 | 1.00 | 56.88 | C |

FIG. 3B

```
ATOM     57  CZ  PHE A 543     -17.797  41.742  12.186  1.00 56.88      C
ATOM     58  CE2 PHE A 543     -18.466  41.325  13.326  1.00 55.46      C
ATOM     59  CD2 PHE A 543     -18.004  40.240  14.027  1.00 55.86      C
ATOM     60  C   PHE A 543     -16.333  35.892  14.574  1.00 61.45      C
ATOM     61  O   PHE A 543     -16.534  35.714  15.779  1.00 61.88      O
ATOM     62  N   GLN A 544     -15.562  35.101  13.834  1.00 60.44      N
ATOM     63  CA  GLN A 544     -14.878  33.938  14.405  1.00 59.57      C
ATOM     64  CB  GLN A 544     -14.792  32.777  13.394  1.00 60.32      C
ATOM     65  CG  GLN A 544     -16.153  32.175  12.981  1.00 62.61      C
ATOM     66  CD  GLN A 544     -16.910  31.522  14.147  1.00 65.09      C
ATOM     67  OE1 GLN A 544     -16.350  31.294  15.225  1.00 66.46      O
ATOM     68  NE2 GLN A 544     -18.187  31.216  13.926  1.00 66.08      N
ATOM     69  C   GLN A 544     -13.502  34.352  14.907  1.00 58.01      C
ATOM     70  O   GLN A 544     -12.554  34.510  14.135  1.00 58.45      O
ATOM     71  N   VAL A 545     -13.413  34.556  16.218  1.00 55.84      N
ATOM     72  CA  VAL A 545     -12.211  35.100  16.851  1.00 52.69      C
ATOM     73  CB  VAL A 545     -12.345  36.640  17.133  1.00 52.82      C
ATOM     74  CG1 VAL A 545     -12.541  37.416  15.841  1.00 51.59      C
ATOM     75  CG2 VAL A 545     -13.480  36.953  18.113  1.00 52.34      C
ATOM     76  C   VAL A 545     -11.999  34.323  18.134  1.00 50.92      C
ATOM     77  O   VAL A 545     -12.797  33.433  18.464  1.00 51.24      O
ATOM     78  N   TYR A 546     -10.937  34.640  18.863  1.00 48.60      N
ATOM     79  CA  TYR A 546     -10.733  34.014  20.154  1.00 46.13      C
ATOM     80  CB  TYR A 546      -9.312  33.450  20.290  1.00 47.88      C
ATOM     81  CG  TYR A 546      -8.956  32.491  19.164  1.00 49.86      C
ATOM     82  CD1 TYR A 546      -8.490  32.972  17.938  1.00 51.70      C
ATOM     83  CE1 TYR A 546      -8.168  32.104  16.888  1.00 53.30      C
ATOM     84  CZ  TYR A 546      -8.319  30.738  17.054  1.00 52.64      C
ATOM     85  OH  TYR A 546      -8.008  29.899  15.993  1.00 53.81      O
ATOM     86  CE2 TYR A 546      -8.792  30.226  18.263  1.00 53.05      C
ATOM     87  CD2 TYR A 546      -9.111  31.109  19.314  1.00 51.40      C
ATOM     88  C   TYR A 546     -11.086  34.982  21.275  1.00 43.74      C
ATOM     89  O   TYR A 546     -10.631  36.122  21.293  1.00 42.55      O
ATOM     90  N   TYR A 547     -11.932  34.515  22.188  1.00 40.90      N
ATOM     91  CA  TYR A 547     -12.277  35.261  23.370  1.00 38.59      C
ATOM     92  CB  TYR A 547     -13.662  34.865  23.886  1.00 37.62      C
ATOM     93  CG  TYR A 547     -14.186  35.757  25.008  1.00 36.43      C
ATOM     94  CD1 TYR A 547     -14.005  37.146  24.975  1.00 34.21      C
ATOM     95  CE1 TYR A 547     -14.492  37.967  25.995  1.00 34.09      C
ATOM     96  CZ  TYR A 547     -15.193  37.403  27.051  1.00 35.79      C
ATOM     97  OH  TYR A 547     -15.694  38.206  28.053  1.00 35.32      O
ATOM     98  CE2 TYR A 547     -15.393  36.031  27.105  1.00 36.64      C
ATOM     99  CD2 TYR A 547     -14.890  35.213  26.082  1.00 36.20      C
ATOM    100  C   TYR A 547     -11.238  34.940  24.424  1.00 37.32      C
ATOM    101  O   TYR A 547     -11.094  33.789  24.832  1.00 36.99      O
ATOM    102  N   LEU A 548     -10.521  35.971  24.850  1.00 36.00      N
ATOM    103  CA  LEU A 548      -9.458  35.829  25.833  1.00 34.83      C
ATOM    104  CB  LEU A 548      -8.346  36.850  25.545  1.00 34.37      C
ATOM    105  CG  LEU A 548      -7.722  36.828  24.142  1.00 34.41      C
ATOM    106  CD1 LEU A 548      -6.819  38.038  23.877  1.00 33.95      C
ATOM    107  CD2 LEU A 548      -6.964  35.538  23.919  1.00 33.02      C
ATOM    108  C   LEU A 548     -10.004  36.002  27.247  1.00 34.38      C
ATOM    109  O   LEU A 548      -9.322  35.714  28.221  1.00 35.07      O
ATOM    110  N   GLY A 549     -11.229  36.502  27.360  1.00 33.75      N
ATOM    111  CA  GLY A 549     -11.873  36.654  28.655  1.00 32.42      C
ATOM    112  C   GLY A 549     -12.061  38.111  29.020  1.00 32.53      C
```

FIG. 3C

```
ATOM    113  O    GLY A 549     -11.938  39.012  28.174  1.00 31.90           O
ATOM    114  N    ASN A 550     -12.373  38.340  30.289  1.00 32.21           N
ATOM    115  CA   ASN A 550     -12.596  39.679  30.781  1.00 32.92           C
ATOM    116  CB   ASN A 550     -14.086  40.035  30.730  1.00 32.69           C
ATOM    117  CG   ASN A 550     -14.939  39.163  31.649  1.00 34.88           C
ATOM    118  OD1  ASN A 550     -14.921  39.337  32.867  1.00 35.96           O
ATOM    119  ND2  ASN A 550     -15.692  38.218  31.059  1.00 35.37           N
ATOM    120  C    ASN A 550     -11.985  39.851  32.163  1.00 33.22           C
ATOM    121  O    ASN A 550     -11.855  38.880  32.915  1.00 33.86           O
ATOM    122  N    VAL A 551     -11.568  41.076  32.462  1.00 33.02           N
ATOM    123  CA   VAL A 551     -10.913  41.418  33.721  1.00 33.38           C
ATOM    124  CB   VAL A 551      -9.348  41.449  33.619  1.00 33.75           C
ATOM    125  CG1  VAL A 551      -8.761  40.060  33.230  1.00 35.89           C
ATOM    126  CG2  VAL A 551      -8.845  42.541  32.657  1.00 33.38           C
ATOM    127  C    VAL A 551     -11.446  42.781  34.170  1.00 33.19           C
ATOM    128  O    VAL A 551     -11.835  43.604  33.327  1.00 31.95           O
ATOM    129  N    PRO A 552     -11.518  43.012  35.494  1.00 33.33           N
ATOM    130  CA   PRO A 552     -11.874  44.362  35.931  1.00 33.21           C
ATOM    131  CB   PRO A 552     -11.999  44.230  37.461  1.00 33.11           C
ATOM    132  CG   PRO A 552     -11.237  43.038  37.815  1.00 34.47           C
ATOM    133  CD   PRO A 552     -11.302  42.100  36.635  1.00 33.83           C
ATOM    134  C    PRO A 552     -10.760  45.365  35.583  1.00 32.60           C
ATOM    135  O    PRO A 552      -9.586  45.014  35.573  1.00 32.37           O
ATOM    136  N    VAL A 553     -11.137  46.600  35.300  1.00 32.41           N
ATOM    137  CA   VAL A 553     -10.144  47.666  35.065  1.00 31.24           C
ATOM    138  CB   VAL A 553      -9.955  47.980  33.552  1.00 31.18           C
ATOM    139  CG1  VAL A 553      -9.215  46.807  32.821  1.00 27.32           C
ATOM    140  CG2  VAL A 553     -11.296  48.315  32.889  1.00 29.33           C
ATOM    141  C    VAL A 553     -10.599  48.896  35.835  1.00 31.97           C
ATOM    142  O    VAL A 553     -11.770  48.986  36.227  1.00 30.80           O
ATOM    143  N    ALA A 554      -9.680  49.835  36.036  1.00 32.25           N
ATOM    144  CA   ALA A 554      -9.890  50.979  36.944  1.00 33.13           C
ATOM    145  CB   ALA A 554      -8.541  51.451  37.513  1.00 33.05           C
ATOM    146  C    ALA A 554     -10.619  52.150  36.343  1.00 33.54           C
ATOM    147  O    ALA A 554     -11.228  52.942  37.079  1.00 34.15           O
ATOM    148  N    LYS A 555     -10.579  52.262  35.014  1.00 33.28           N
ATOM    149  CA   LYS A 555     -11.049  53.457  34.325  1.00 33.90           C
ATOM    150  CB   LYS A 555      -9.833  54.299  33.837  1.00 33.74           C
ATOM    151  CG   LYS A 555      -8.883  54.783  34.945  1.00 37.51           C
ATOM    152  CD   LYS A 555      -7.751  55.740  34.419  1.00 38.10           C
ATOM    153  CE   LYS A 555      -6.576  55.012  33.738  1.00 45.23           C
ATOM    154  NZ   LYS A 555      -5.452  55.888  33.139  1.00 44.08           N
ATOM    155  C    LYS A 555     -11.937  53.070  33.123  1.00 32.46           C
ATOM    156  O    LYS A 555     -11.773  51.994  32.555  1.00 31.18           O
ATOM    157  N    PRO A 556     -12.884  53.952  32.738  1.00 31.86           N
ATOM    158  CA   PRO A 556     -13.762  53.663  31.600  1.00 31.40           C
ATOM    159  CB   PRO A 556     -14.836  54.757  31.702  1.00 31.37           C
ATOM    160  CG   PRO A 556     -14.129  55.902  32.345  1.00 31.96           C
ATOM    161  CD   PRO A 556     -13.195  55.264  33.351  1.00 31.73           C
ATOM    162  C    PRO A 556     -13.083  53.751  30.222  1.00 30.75           C
ATOM    163  O    PRO A 556     -13.616  53.212  29.254  1.00 29.53           O
ATOM    164  N    VAL A 557     -11.939  54.442  30.138  1.00 31.08           N
ATOM    165  CA   VAL A 557     -11.273  54.716  28.838  1.00 31.01           C
ATOM    166  CB   VAL A 557     -11.667  56.119  28.236  1.00 30.88           C
ATOM    167  CG1  VAL A 557     -13.201  56.293  28.081  1.00 31.76           C
ATOM    168  CG2  VAL A 557     -11.083  57.251  29.069  1.00 32.46           C
```

FIG. 3D

```
ATOM    169  C    VAL A 557      -9.732   54.624   28.913  1.00 30.42           C
ATOM    170  O    VAL A 557      -9.146   54.714   29.984  1.00 30.81           O
ATOM    171  N    GLY A 558      -9.101   54.428   27.768  1.00 30.36           N
ATOM    172  CA   GLY A 558      -7.640   54.630   27.623  1.00 30.44           C
ATOM    173  C    GLY A 558      -6.973   53.462   26.935  1.00 29.96           C
ATOM    174  O    GLY A 558      -7.217   52.319   27.319  1.00 29.15           O
ATOM    175  N    VAL A 559      -6.146   53.720   25.911  1.00 29.92           N
ATOM    176  CA   VAL A 559      -5.388   52.625   25.291  1.00 29.58           C
ATOM    177  CB   VAL A 559      -4.680   52.997   23.924  1.00 30.28           C
ATOM    178  CG1  VAL A 559      -5.698   53.220   22.827  1.00 31.83           C
ATOM    179  CG2  VAL A 559      -3.781   54.207   24.062  1.00 31.64           C
ATOM    180  C    VAL A 559      -4.396   51.980   26.283  1.00 28.48           C
ATOM    181  O    VAL A 559      -4.109   50.787   26.201  1.00 28.51           O
ATOM    182  N    ASP A 560      -3.877   52.768   27.210  1.00 28.47           N
ATOM    183  CA   ASP A 560      -3.025   52.220   28.270  1.00 29.12           C
ATOM    184  CB   ASP A 560      -2.499   53.329   29.173  1.00 29.35           C
ATOM    185  CG   ASP A 560      -3.608   54.097   29.861  1.00 34.74           C
ATOM    186  OD1  ASP A 560      -4.601   54.440   29.187  1.00 40.72           O
ATOM    187  OD2  ASP A 560      -3.483   54.379   31.079  1.00 37.91           O
ATOM    188  C    ASP A 560      -3.760   51.196   29.145  1.00 28.18           C
ATOM    189  O    ASP A 560      -3.168   50.211   29.559  1.00 27.06           O
ATOM    190  N    VAL A 561      -5.044   51.466   29.427  1.00 27.60           N
ATOM    191  CA   VAL A 561      -5.876   50.574   30.240  1.00 27.32           C
ATOM    192  CB   VAL A 561      -7.276   51.214   30.557  1.00 26.96           C
ATOM    193  CG1  VAL A 561      -8.179   50.234   31.288  1.00 26.68           C
ATOM    194  CG2  VAL A 561      -7.085   52.454   31.416  1.00 27.04           C
ATOM    195  C    VAL A 561      -6.063   49.250   29.527  1.00 26.46           C
ATOM    196  O    VAL A 561      -5.855   48.204   30.115  1.00 26.50           O
ATOM    197  N    ILE A 562      -6.438   49.295   28.253  1.00 26.19           N
ATOM    198  CA   ILE A 562      -6.693   48.069   27.523  1.00 25.75           C
ATOM    199  CB   ILE A 562      -7.548   48.268   26.219  1.00 26.96           C
ATOM    200  CG1  ILE A 562      -6.791   49.068   25.143  1.00 28.22           C
ATOM    201  CD1  ILE A 562      -6.240   48.172   23.990  1.00 31.13           C
ATOM    202  CG2  ILE A 562      -8.974   48.868   26.533  1.00 24.67           C
ATOM    203  C    ILE A 562      -5.421   47.292   27.203  1.00 25.16           C
ATOM    204  O    ILE A 562      -5.442   46.073   27.213  1.00 24.80           O
ATOM    205  N    ASN A 563      -4.314   47.983   26.953  1.00 25.25           N
ATOM    206  CA   ASN A 563      -3.044   47.268   26.722  1.00 25.43           C
ATOM    207  CB   ASN A 563      -2.000   48.175   26.020  1.00 25.29           C
ATOM    208  CG   ASN A 563      -2.313   48.362   24.536  1.00 22.84           C
ATOM    209  OD1  ASN A 563      -2.290   47.414   23.788  1.00 25.62           O
ATOM    210  ND2  ASN A 563      -2.651   49.578   24.130  1.00 23.16           N
ATOM    211  C    ASN A 563      -2.486   46.643   27.982  1.00 25.57           C
ATOM    212  O    ASN A 563      -1.877   45.602   27.905  1.00 26.12           O
ATOM    213  N    GLY A 564      -2.725   47.271   29.141  1.00 26.44           N
ATOM    214  CA   GLY A 564      -2.379   46.663   30.422  1.00 27.37           C
ATOM    215  C    GLY A 564      -3.165   45.387   30.651  1.00 27.80           C
ATOM    216  O    GLY A 564      -2.587   44.371   31.041  1.00 27.67           O
ATOM    217  N    ALA A 565      -4.480   45.438   30.364  1.00 27.95           N
ATOM    218  CA   ALA A 565      -5.376   44.275   30.473  1.00 27.82           C
ATOM    219  CB   ALA A 565      -6.831   44.701   30.188  1.00 28.29           C
ATOM    220  C    ALA A 565      -4.954   43.132   29.533  1.00 28.35           C
ATOM    221  O    ALA A 565      -4.874   41.976   29.963  1.00 28.25           O
ATOM    222  N    LEU A 566      -4.657   43.461   28.265  1.00 27.76           N
ATOM    223  CA   LEU A 566      -4.190   42.477   27.269  1.00 28.20           C
ATOM    224  CB   LEU A 566      -3.997   43.143   25.896  1.00 28.35           C
```

FIG. 3E

```
ATOM    225  CG   LEU A 566      -5.290  43.543  25.175  1.00 28.00           C
ATOM    226  CD1  LEU A 566      -5.041  44.502  24.049  1.00 24.74           C
ATOM    227  CD2  LEU A 566      -5.978  42.280  24.698  1.00 27.34           C
ATOM    228  C    LEU A 566      -2.888  41.788  27.666  1.00 28.41           C
ATOM    229  O    LEU A 566      -2.798  40.568  27.646  1.00 28.71           O
ATOM    230  N    GLU A 567      -1.874  42.573  28.018  1.00 29.43           N
ATOM    231  CA   GLU A 567      -0.606  41.989  28.492  1.00 29.86           C
ATOM    232  CB   GLU A 567       0.414  43.083  28.810  1.00 29.89           C
ATOM    233  CG   GLU A 567       0.949  43.781  27.547  1.00 28.82           C
ATOM    234  CD   GLU A 567       1.792  44.987  27.815  1.00 28.15           C
ATOM    235  OE1  GLU A 567       2.005  45.319  28.978  1.00 28.26           O
ATOM    236  OE2  GLU A 567       2.275  45.627  26.855  1.00 27.67           O
ATOM    237  C    GLU A 567      -0.820  41.037  29.687  1.00 30.47           C
ATOM    238  O    GLU A 567      -0.258  39.958  29.714  1.00 30.87           O
ATOM    239  N    SER A 568      -1.645  41.432  30.651  1.00 30.88           N
ATOM    240  CA   SER A 568      -1.936  40.585  31.791  1.00 31.87           C
ATOM    241  CB   SER A 568      -2.808  41.318  32.807  1.00 32.24           C
ATOM    242  OG   SER A 568      -1.998  42.256  33.500  1.00 35.93           O
ATOM    243  C    SER A 568      -2.558  39.250  31.415  1.00 32.20           C
ATOM    244  O    SER A 568      -2.039  38.207  31.834  1.00 32.35           O
ATOM    245  N    VAL A 569      -3.643  39.269  30.627  1.00 32.19           N
ATOM    246  CA   VAL A 569      -4.297  38.029  30.204  1.00 32.56           C
ATOM    247  CB   VAL A 569      -5.734  38.270  29.605  1.00 32.72           C
ATOM    248  CG1  VAL A 569      -5.689  38.814  28.183  1.00 31.15           C
ATOM    249  CG2  VAL A 569      -6.506  36.990  29.626  1.00 33.77           C
ATOM    250  C    VAL A 569      -3.421  37.145  29.278  1.00 32.86           C
ATOM    251  O    VAL A 569      -3.410  35.910  29.398  1.00 33.47           O
ATOM    252  N    LEU A 570      -2.676  37.766  28.373  1.00 32.79           N
ATOM    253  CA   LEU A 570      -1.791  37.001  27.485  1.00 33.59           C
ATOM    254  CB   LEU A 570      -1.205  37.891  26.373  1.00 33.50           C
ATOM    255  CG   LEU A 570      -2.211  38.436  25.345  1.00 33.90           C
ATOM    256  CD1  LEU A 570      -1.564  39.499  24.484  1.00 35.01           C
ATOM    257  CD2  LEU A 570      -2.787  37.342  24.452  1.00 34.24           C
ATOM    258  C    LEU A 570      -0.667  36.311  28.252  1.00 34.19           C
ATOM    259  O    LEU A 570      -0.241  35.240  27.874  1.00 34.18           O
ATOM    260  N    SER A 571      -0.205  36.928  29.332  1.00 35.62           N
ATOM    261  CA   SER A 571       0.879  36.371  30.134  1.00 38.21           C
ATOM    262  CB   SER A 571       1.487  37.440  31.025  1.00 37.06           C
ATOM    263  OG   SER A 571       0.619  37.749  32.092  1.00 38.21           O
ATOM    264  C    SER A 571       0.440  35.198  30.988  1.00 40.06           C
ATOM    265  O    SER A 571       1.277  34.431  31.432  1.00 41.25           O
ATOM    266  N    SER A 572      -0.868  35.054  31.203  1.00 42.95           N
ATOM    267  CA   SER A 572      -1.418  34.044  32.117  1.00 45.41           C
ATOM    268  CB   SER A 572      -2.254  34.721  33.218  1.00 45.21           C
ATOM    269  OG   SER A 572      -3.389  35.413  32.684  1.00 46.75           O
ATOM    270  C    SER A 572      -2.251  32.975  31.407  1.00 47.05           C
ATOM    271  O    SER A 572      -3.034  32.269  32.034  1.00 47.61           O
ATOM    272  N    SER A 573      -2.078  32.860  30.097  1.00 48.97           N
ATOM    273  CA   SER A 573      -2.841  31.921  29.299  1.00 51.00           C
ATOM    274  CB   SER A 573      -4.154  32.557  28.810  1.00 51.15           C
ATOM    275  OG   SER A 573      -3.925  33.757  28.064  1.00 52.55           O
ATOM    276  C    SER A 573      -1.977  31.497  28.123  1.00 52.25           C
ATOM    277  O    SER A 573      -0.988  32.164  27.805  1.00 52.61           O
ATOM    278  N    SER A 574      -2.319  30.369  27.510  1.00 53.46           N
ATOM    279  CA   SER A 574      -1.657  29.924  26.286  1.00 54.91           C
ATOM    280  CB   SER A 574      -0.891  28.611  26.509  1.00 55.04           C
```

FIG. 3F

| ATOM | 281 | OG  | SER | A | 574 | -1.733  | 27.599 | 27.046 | 1.00 | 56.12 | O |
| ATOM | 282 | C   | SER | A | 574 | -2.707  | 29.767 | 25.202 | 1.00 | 55.46 | C |
| ATOM | 283 | O   | SER | A | 574 | -3.889  | 29.620 | 25.500 | 1.00 | 55.83 | O |
| ATOM | 284 | N   | ARG | A | 575 | -2.279  | 29.801 | 23.949 | 1.00 | 56.28 | N |
| ATOM | 285 | CA  | ARG | A | 575 | -3.199  | 29.771 | 22.818 | 1.00 | 56.90 | C |
| ATOM | 286 | CB  | ARG | A | 575 | -2.428  | 29.787 | 21.504 | 1.00 | 56.83 | C |
| ATOM | 287 | CG  | ARG | A | 575 | -1.566  | 31.006 | 21.337 | 1.00 | 55.25 | C |
| ATOM | 288 | CD  | ARG | A | 575 | -1.343  | 31.314 | 19.880 | 1.00 | 53.80 | C |
| ATOM | 289 | NE  | ARG | A | 575 | -0.534  | 32.521 | 19.726 | 1.00 | 53.41 | N |
| ATOM | 290 | CZ  | ARG | A | 575 | -0.489  | 33.266 | 18.626 | 1.00 | 53.10 | C |
| ATOM | 291 | NH1 | ARG | A | 575 | -1.221  | 32.932 | 17.562 | 1.00 | 53.47 | N |
| ATOM | 292 | NH2 | ARG | A | 575 |  0.282  | 34.351 | 18.592 | 1.00 | 51.71 | N |
| ATOM | 293 | C   | ARG | A | 575 | -4.207  | 28.623 | 22.825 | 1.00 | 58.09 | C |
| ATOM | 294 | O   | ARG | A | 575 | -5.309  | 28.765 | 22.296 | 1.00 | 58.19 | O |
| ATOM | 295 | N   | GLU | A | 576 | -3.831  | 27.499 | 23.426 | 1.00 | 59.31 | N |
| ATOM | 296 | CA  | GLU | A | 576 | -4.710  | 26.322 | 23.530 | 1.00 | 60.92 | C |
| ATOM | 297 | CB  | GLU | A | 576 | -3.887  | 25.072 | 23.849 | 1.00 | 61.17 | C |
| ATOM | 298 | CG  | GLU | A | 576 | -2.631  | 24.931 | 22.978 | 1.00 | 63.14 | C |
| ATOM | 299 | CD  | GLU | A | 576 | -1.833  | 23.672 | 23.290 | 1.00 | 64.38 | C |
| ATOM | 300 | OE1 | GLU | A | 576 | -1.436  | 23.478 | 24.478 | 1.00 | 68.27 | O |
| ATOM | 301 | OE2 | GLU | A | 576 | -1.596  | 22.881 | 22.335 | 1.00 | 68.85 | O |
| ATOM | 302 | C   | GLU | A | 576 | -5.827  | 26.516 | 24.570 | 1.00 | 59.98 | C |
| ATOM | 303 | O   | GLU | A | 576 | -6.886  | 25.887 | 24.490 | 1.00 | 60.20 | O |
| ATOM | 304 | N   | GLN | A | 577 | -5.583  | 27.400 | 25.534 | 1.00 | 58.97 | N |
| ATOM | 305 | CA  | GLN | A | 577 | -6.605  | 27.809 | 26.497 | 1.00 | 58.09 | C |
| ATOM | 306 | CB  | GLN | A | 577 | -5.969  | 28.503 | 27.706 | 1.00 | 58.34 | C |
| ATOM | 307 | CG  | GLN | A | 577 | -4.869  | 27.720 | 28.411 | 1.00 | 59.62 | C |
| ATOM | 308 | CD  | GLN | A | 577 | -4.289  | 28.482 | 29.597 | 1.00 | 60.30 | C |
| ATOM | 309 | OE1 | GLN | A | 577 | -4.947  | 29.358 | 30.176 | 1.00 | 63.29 | O |
| ATOM | 310 | NE2 | GLN | A | 577 | -3.054  | 28.146 | 29.972 | 1.00 | 62.87 | N |
| ATOM | 311 | C   | GLN | A | 577 | -7.650  | 28.749 | 25.896 | 1.00 | 56.05 | C |
| ATOM | 312 | O   | GLN | A | 577 | -8.738  | 28.878 | 26.453 | 1.00 | 56.02 | O |
| ATOM | 313 | N   | TRP | A | 578 | -7.325  | 29.402 | 24.777 | 1.00 | 53.90 | N |
| ATOM | 314 | CA  | TRP | A | 578 | -8.209  | 30.417 | 24.195 | 1.00 | 52.07 | C |
| ATOM | 315 | CB  | TRP | A | 578 | -7.540  | 31.205 | 23.058 | 1.00 | 50.13 | C |
| ATOM | 316 | CG  | TRP | A | 578 | -6.295  | 31.982 | 23.438 | 1.00 | 48.27 | C |
| ATOM | 317 | CD1 | TRP | A | 578 | -5.798  | 32.200 | 24.703 | 1.00 | 45.19 | C |
| ATOM | 318 | NE1 | TRP | A | 578 | -4.652  | 32.966 | 24.633 | 1.00 | 45.04 | N |
| ATOM | 319 | CE2 | TRP | A | 578 | -4.393  | 33.273 | 23.323 | 1.00 | 44.69 | C |
| ATOM | 320 | CD2 | TRP | A | 578 | -5.416  | 32.682 | 22.538 | 1.00 | 46.37 | C |
| ATOM | 321 | CE3 | TRP | A | 578 | -5.383  | 32.852 | 21.147 | 1.00 | 45.53 | C |
| ATOM | 322 | CZ3 | TRP | A | 578 | -4.341  | 33.604 | 20.589 | 1.00 | 45.72 | C |
| ATOM | 323 | CH2 | TRP | A | 578 | -3.347  | 34.180 | 21.401 | 1.00 | 45.66 | C |
| ATOM | 324 | CZ2 | TRP | A | 578 | -3.355  | 34.020 | 22.763 | 1.00 | 45.94 | C |
| ATOM | 325 | C   | TRP | A | 578 | -9.519  | 29.820 | 23.692 | 1.00 | 52.43 | C |
| ATOM | 326 | O   | TRP | A | 578 | -9.542  | 28.717 | 23.120 | 1.00 | 52.95 | O |
| ATOM | 327 | N   | THR | A | 579 | -10.602 | 30.569 | 23.893 | 1.00 | 52.10 | N |
| ATOM | 328 | CA  | THR | A | 579 | -11.946 | 30.099 | 23.579 | 1.00 | 51.62 | C |
| ATOM | 329 | CB  | THR | A | 579 | -12.947 | 30.545 | 24.654 | 1.00 | 51.82 | C |
| ATOM | 330 | OG1 | THR | A | 579 | -12.522 | 30.036 | 25.925 | 1.00 | 51.44 | O |
| ATOM | 331 | CG2 | THR | A | 579 | -14.360 | 30.041 | 24.345 | 1.00 | 51.88 | C |
| ATOM | 332 | C   | THR | A | 579 | -12.361 | 30.588 | 22.199 | 1.00 | 51.51 | C |
| ATOM | 333 | O   | THR | A | 579 | -12.531 | 31.788 | 21.995 | 1.00 | 50.57 | O |
| ATOM | 334 | N   | PRO | A | 580 | -12.501 | 29.649 | 21.230 | 1.00 | 51.75 | N |
| ATOM | 335 | CA  | PRO | A | 580 | -12.954 | 30.077 | 19.917 | 1.00 | 51.76 | C |
| ATOM | 336 | CB  | PRO | A | 580 | -12.851 | 28.804 | 19.068 | 1.00 | 51.74 | C |

FIG. 3G

| | | | | | | | | | | |
|---|---|---|---|---|---|---|---|---|---|---|
| ATOM | 337 | CG | PRO | A | 580 | -12.930 | 27.687 | 20.046 | 1.00 52.07 | C |
| ATOM | 338 | CD | PRO | A | 580 | -12.256 | 28.193 | 21.290 | 1.00 51.66 | C |
| ATOM | 339 | C | PRO | A | 580 | -14.396 | 30.531 | 20.055 | 1.00 52.01 | C |
| ATOM | 340 | O | PRO | A | 580 | -15.171 | 29.946 | 20.828 | 1.00 52.00 | O |
| ATOM | 341 | N | SER | A | 581 | -14.750 | 31.574 | 19.327 | 1.00 52.08 | N |
| ATOM | 342 | CA | SER | A | 581 | -16.014 | 32.223 | 19.569 | 1.00 52.60 | C |
| ATOM | 343 | CB | SER | A | 581 | -15.939 | 33.059 | 20.865 | 1.00 52.42 | C |
| ATOM | 344 | OG | SER | A | 581 | -15.080 | 34.177 | 20.706 | 1.00 51.23 | O |
| ATOM | 345 | C | SER | A | 581 | -16.356 | 33.121 | 18.402 | 1.00 53.11 | C |
| ATOM | 346 | O | SER | A | 581 | -15.506 | 33.404 | 17.549 | 1.00 53.60 | O |
| ATOM | 347 | N | HIS | A | 582 | -17.598 | 33.594 | 18.386 | 1.00 53.35 | N |
| ATOM | 348 | CA | HIS | A | 582 | -18.001 | 34.629 | 17.436 | 1.00 53.51 | C |
| ATOM | 349 | CB | HIS | A | 582 | -18.851 | 34.029 | 16.296 | 1.00 54.23 | C |
| ATOM | 350 | CG | HIS | A | 582 | -19.712 | 32.888 | 16.730 | 1.00 57.52 | C |
| ATOM | 351 | ND1 | HIS | A | 582 | -21.078 | 32.997 | 16.871 | 1.00 61.13 | N |
| ATOM | 352 | CE1 | HIS | A | 582 | -21.570 | 31.842 | 17.287 | 1.00 61.64 | C |
| ATOM | 353 | NE2 | HIS | A | 582 | -20.571 | 30.988 | 17.427 | 1.00 61.13 | N |
| ATOM | 354 | CD2 | HIS | A | 582 | -19.398 | 31.618 | 17.083 | 1.00 60.70 | C |
| ATOM | 355 | C | HIS | A | 582 | -18.709 | 35.785 | 18.149 | 1.00 52.31 | C |
| ATOM | 356 | O | HIS | A | 582 | -19.362 | 35.587 | 19.177 | 1.00 52.31 | O |
| ATOM | 357 | N | VAL | A | 583 | -18.541 | 36.990 | 17.616 | 1.00 51.10 | N |
| ATOM | 358 | CA | VAL | A | 583 | -19.176 | 38.155 | 18.192 | 1.00 49.97 | C |
| ATOM | 359 | CB | VAL | A | 583 | -18.191 | 39.331 | 18.433 | 1.00 49.97 | C |
| ATOM | 360 | CG1 | VAL | A | 583 | -18.935 | 40.581 | 18.924 | 1.00 48.62 | C |
| ATOM | 361 | CG2 | VAL | A | 583 | -17.096 | 38.929 | 19.416 | 1.00 49.14 | C |
| ATOM | 362 | C | VAL | A | 583 | -20.299 | 38.603 | 17.280 | 1.00 49.39 | C |
| ATOM | 363 | O | VAL | A | 583 | -20.072 | 39.015 | 16.134 | 1.00 49.15 | O |
| ATOM | 364 | N | SER | A | 584 | -21.512 | 38.527 | 17.806 | 1.00 48.05 | N |
| ATOM | 365 | CA | SER | A | 584 | -22.650 | 39.048 | 17.092 | 1.00 47.33 | C |
| ATOM | 366 | CB | SER | A | 584 | -23.909 | 38.250 | 17.414 | 1.00 47.45 | C |
| ATOM | 367 | OG | SER | A | 584 | -24.990 | 38.787 | 16.689 | 1.00 48.48 | O |
| ATOM | 368 | C | SER | A | 584 | -22.831 | 40.513 | 17.441 | 1.00 46.53 | C |
| ATOM | 369 | O | SER | A | 584 | -22.950 | 40.886 | 18.607 | 1.00 45.72 | O |
| ATOM | 370 | N | VAL | A | 585 | -22.831 | 41.342 | 16.408 | 1.00 46.16 | N |
| ATOM | 371 | CA | VAL | A | 585 | -22.943 | 42.768 | 16.569 | 1.00 45.65 | C |
| ATOM | 372 | CB | VAL | A | 585 | -21.881 | 43.523 | 15.698 | 1.00 45.79 | C |
| ATOM | 373 | CG1 | VAL | A | 585 | -22.038 | 45.040 | 15.813 | 1.00 44.34 | C |
| ATOM | 374 | CG2 | VAL | A | 585 | -20.455 | 43.099 | 16.075 | 1.00 44.74 | C |
| ATOM | 375 | C | VAL | A | 585 | -24.371 | 43.117 | 16.168 | 1.00 46.22 | C |
| ATOM | 376 | O | VAL | A | 585 | -24.739 | 42.993 | 15.001 | 1.00 46.27 | O |
| ATOM | 377 | N | ALA | A | 586 | -25.187 | 43.497 | 17.149 | 1.00 46.23 | N |
| ATOM | 378 | CA | ALA | A | 586 | -26.552 | 43.934 | 16.886 | 1.00 45.93 | C |
| ATOM | 379 | CB | ALA | A | 586 | -27.560 | 43.119 | 17.703 | 1.00 46.27 | C |
| ATOM | 380 | C | ALA | A | 586 | -26.650 | 45.427 | 17.191 | 1.00 45.43 | C |
| ATOM | 381 | O | ALA | A | 586 | -25.688 | 46.012 | 17.724 | 1.00 45.96 | O |
| ATOM | 382 | N | PRO | A | 587 | -27.760 | 46.071 | 16.788 | 1.00 44.77 | N |
| ATOM | 383 | CA | PRO | A | 587 | -27.968 | 47.505 | 17.081 | 1.00 44.26 | C |
| ATOM | 384 | CB | PRO | A | 587 | -29.458 | 47.748 | 16.750 | 1.00 43.98 | C |
| ATOM | 385 | CG | PRO | A | 587 | -30.011 | 46.429 | 16.222 | 1.00 45.44 | C |
| ATOM | 386 | CD | PRO | A | 587 | -28.834 | 45.523 | 15.931 | 1.00 45.15 | C |
| ATOM | 387 | C | PRO | A | 587 | -27.699 | 47.947 | 18.531 | 1.00 43.12 | C |
| ATOM | 388 | O | PRO | A | 587 | -27.115 | 49.017 | 18.757 | 1.00 42.57 | O |
| ATOM | 389 | N | ALA | A | 588 | -28.155 | 47.147 | 19.491 | 1.00 41.59 | N |
| ATOM | 390 | CA | ALA | A | 588 | -28.185 | 47.588 | 20.876 | 1.00 40.49 | C |
| ATOM | 391 | CB | ALA | A | 588 | -29.615 | 47.507 | 21.414 | 1.00 40.48 | C |
| ATOM | 392 | C | ALA | A | 588 | -27.238 | 46.790 | 21.760 | 1.00 39.35 | C |

FIG. 3H

| ATOM | 393 | O   | ALA | A | 588 | -26.954 | 47.193 | 22.880 | 1.00 | 38.51 | O |
|------|-----|-----|-----|---|-----|---------|--------|--------|------|-------|---|
| ATOM | 394 | N   | THR | A | 589 | -26.756 | 45.662 | 21.247 | 1.00 | 39.09 | N |
| ATOM | 395 | CA  | THR | A | 589 | -25.957 | 44.729 | 22.043 | 1.00 | 39.56 | C |
| ATOM | 396 | CB  | THR | A | 589 | -26.813 | 43.551 | 22.605 | 1.00 | 39.97 | C |
| ATOM | 397 | OG1 | THR | A | 589 | -27.358 | 42.792 | 21.513 | 1.00 | 42.07 | O |
| ATOM | 398 | CG2 | THR | A | 589 | -27.960 | 44.039 | 23.516 | 1.00 | 39.33 | C |
| ATOM | 399 | C   | THR | A | 589 | -24.827 | 44.109 | 21.234 | 1.00 | 39.15 | C |
| ATOM | 400 | O   | THR | A | 589 | -24.919 | 44.005 | 20.005 | 1.00 | 39.39 | O |
| ATOM | 401 | N   | LEU | A | 590 | -23.764 | 43.706 | 21.935 | 1.00 | 38.62 | N |
| ATOM | 402 | CA  | LEU | A | 590 | -22.786 | 42.756 | 21.411 | 1.00 | 38.04 | C |
| ATOM | 403 | CB  | LEU | A | 590 | -21.332 | 43.234 | 21.608 | 1.00 | 37.39 | C |
| ATOM | 404 | CG  | LEU | A | 590 | -20.940 | 44.697 | 21.366 | 1.00 | 38.35 | C |
| ATOM | 405 | CD1 | LEU | A | 590 | -19.423 | 44.854 | 21.480 | 1.00 | 36.81 | C |
| ATOM | 406 | CD2 | LEU | A | 590 | -21.443 | 45.250 | 20.022 | 1.00 | 38.12 | C |
| ATOM | 407 | C   | LEU | A | 590 | -22.989 | 41.454 | 22.172 | 1.00 | 38.23 | C |
| ATOM | 408 | O   | LEU | A | 590 | -23.087 | 41.456 | 23.410 | 1.00 | 37.61 | O |
| ATOM | 409 | N   | THR | A | 591 | -23.047 | 40.352 | 21.438 | 1.00 | 38.38 | N |
| ATOM | 410 | CA  | THR | A | 591 | -23.143 | 39.048 | 22.061 | 1.00 | 40.18 | C |
| ATOM | 411 | CB  | THR | A | 591 | -24.488 | 38.336 | 21.722 | 1.00 | 40.11 | C |
| ATOM | 412 | OG1 | THR | A | 591 | -25.573 | 39.241 | 21.980 | 1.00 | 40.14 | O |
| ATOM | 413 | CG2 | THR | A | 591 | -24.676 | 37.090 | 22.578 | 1.00 | 39.56 | C |
| ATOM | 414 | C   | THR | A | 591 | -21.945 | 38.207 | 21.643 | 1.00 | 41.23 | C |
| ATOM | 415 | O   | THR | A | 591 | -21.635 | 38.105 | 20.459 | 1.00 | 41.38 | O |
| ATOM | 416 | N   | ILE | A | 592 | -21.274 | 37.638 | 22.637 | 1.00 | 43.04 | N |
| ATOM | 417 | CA  | ILE | A | 592 | -20.141 | 36.740 | 22.426 | 1.00 | 45.76 | C |
| ATOM | 418 | CB  | ILE | A | 592 | -18.942 | 37.053 | 23.391 | 1.00 | 45.62 | C |
| ATOM | 419 | CG1 | ILE | A | 592 | -18.692 | 38.575 | 23.504 | 1.00 | 44.87 | C |
| ATOM | 420 | CD1 | ILE | A | 592 | -17.956 | 38.999 | 24.766 | 1.00 | 45.07 | C |
| ATOM | 421 | CG2 | ILE | A | 592 | -17.701 | 36.303 | 22.925 | 1.00 | 44.82 | C |
| ATOM | 422 | C   | ILE | A | 592 | -20.580 | 35.293 | 22.621 | 1.00 | 47.83 | C |
| ATOM | 423 | O   | ILE | A | 592 | -21.066 | 34.922 | 23.684 | 1.00 | 47.79 | O |
| ATOM | 424 | N   | LEU | A | 593 | -20.383 | 34.476 | 21.589 | 1.00 | 51.53 | N |
| ATOM | 425 | CA  | LEU | A | 593 | -20.856 | 33.073 | 21.593 | 1.00 | 54.86 | C |
| ATOM | 426 | CB  | LEU | A | 593 | -22.008 | 32.929 | 20.586 | 1.00 | 55.11 | C |
| ATOM | 427 | CG  | LEU | A | 593 | -23.020 | 34.092 | 20.503 | 1.00 | 55.64 | C |
| ATOM | 428 | CD1 | LEU | A | 593 | -23.151 | 34.666 | 19.089 | 1.00 | 55.17 | C |
| ATOM | 429 | CD2 | LEU | A | 593 | -24.370 | 33.687 | 21.085 | 1.00 | 55.36 | C |
| ATOM | 430 | C   | LEU | A | 593 | -19.737 | 32.070 | 21.252 | 1.00 | 56.64 | C |
| ATOM | 431 | O   | LEU | A | 593 | -18.905 | 32.358 | 20.400 | 1.00 | 56.92 | O |
| ATOM | 432 | N   | HIS | A | 594 | -19.734 | 30.909 | 21.911 | 1.00 | 59.64 | N |
| ATOM | 433 | CA  | HIS | A | 594 | -18.795 | 29.790 | 21.618 | 1.00 | 62.47 | C |
| ATOM | 434 | CB  | HIS | A | 594 | -19.119 | 28.604 | 22.518 | 1.00 | 62.47 | C |
| ATOM | 435 | CG  | HIS | A | 594 | -17.915 | 27.943 | 23.120 | 1.00 | 64.47 | C |
| ATOM | 436 | ND1 | HIS | A | 594 | -16.936 | 27.332 | 22.362 | 1.00 | 65.46 | N |
| ATOM | 437 | CE1 | HIS | A | 594 | -16.012 | 26.829 | 23.165 | 1.00 | 65.84 | C |
| ATOM | 438 | NE2 | HIS | A | 594 | -16.360 | 27.083 | 24.416 | 1.00 | 65.53 | N |
| ATOM | 439 | CD2 | HIS | A | 594 | -17.549 | 27.773 | 24.416 | 1.00 | 65.61 | C |
| ATOM | 440 | C   | HIS | A | 594 | -18.836 | 29.363 | 20.132 | 1.00 | 64.05 | C |
| ATOM | 441 | O   | HIS | A | 594 | -19.915 | 29.400 | 19.513 | 1.00 | 64.16 | O |
| ATOM | 442 | N   | GLN | A | 595 | -17.682 | 28.949 | 19.571 | 1.00 | 65.90 | N |
| ATOM | 443 | CA  | GLN | A | 595 | -17.480 | 28.935 | 18.094 | 1.00 | 67.31 | C |
| ATOM | 444 | CB  | GLN | A | 595 | -16.137 | 28.362 | 17.621 | 1.00 | 67.47 | C |
| ATOM | 445 | CG  | GLN | A | 595 | -16.125 | 28.307 | 16.074 | 1.00 | 68.47 | C |
| ATOM | 446 | CD  | GLN | A | 595 | -14.849 | 27.812 | 15.443 | 1.00 | 70.15 | C |
| ATOM | 447 | OE1 | GLN | A | 595 | -14.213 | 26.874 | 15.931 | 1.00 | 70.63 | O |
| ATOM | 448 | NE2 | GLN | A | 595 | -14.478 | 28.428 | 14.317 | 1.00 | 70.54 | N |

FIG. 3I

| ATOM | 449 | C | GLN | A | 595 | -18.582 | 28.378 | 17.201 | 1.00 | 68.11 | C |
|------|-----|------|-----|---|-----|---------|--------|--------|------|-------|---|
| ATOM | 450 | O | GLN | A | 595 | -18.932 | 29.000 | 16.182 | 1.00 | 68.67 | O |
| ATOM | 451 | N | GLN | A | 596 | -19.103 | 27.195 | 17.515 | 1.00 | 68.88 | N |
| ATOM | 452 | CA | GLN | A | 596 | -20.258 | 26.763 | 16.735 | 1.00 | 69.47 | C |
| ATOM | 453 | CB | GLN | A | 596 | -19.854 | 26.059 | 15.383 | 1.00 | 69.89 | C |
| ATOM | 454 | CG | GLN | A | 596 | -19.567 | 24.522 | 15.458 | 1.00 | 71.70 | C |
| ATOM | 455 | CD | GLN | A | 596 | -20.287 | 23.862 | 14.237 | 1.00 | 74.38 | C |
| ATOM | 456 | OE1 | GLN | A | 596 | -20.469 | 24.488 | 13.165 | 1.00 | 74.81 | O |
| ATOM | 457 | NE2 | GLN | A | 596 | -20.718 | 22.594 | 14.406 | 1.00 | 75.27 | N |
| ATOM | 458 | C | GLN | A | 596 | -21.431 | 26.096 | 17.458 | 1.00 | 69.38 | C |
| ATOM | 459 | O | GLN | A | 596 | -22.525 | 25.945 | 16.873 | 1.00 | 69.59 | O |
| ATOM | 460 | N | THR | A | 597 | -21.212 | 25.750 | 18.733 | 1.00 | 69.13 | N |
| ATOM | 461 | CA | THR | A | 597 | -22.318 | 25.479 | 19.666 | 1.00 | 68.61 | C |
| ATOM | 462 | CB | THR | A | 597 | -21.818 | 25.010 | 21.060 | 1.00 | 68.71 | C |
| ATOM | 463 | OG1 | THR | A | 597 | -21.072 | 26.063 | 21.694 | 1.00 | 69.68 | O |
| ATOM | 464 | CG2 | THR | A | 597 | -20.940 | 23.780 | 20.940 | 1.00 | 68.40 | C |
| ATOM | 465 | C | THR | A | 597 | -23.185 | 26.746 | 19.824 | 1.00 | 68.03 | C |
| ATOM | 466 | O | THR | A | 597 | -24.392 | 26.667 | 20.093 | 1.00 | 68.22 | O |
| ATOM | 467 | N | GLU | A | 598 | -22.549 | 27.905 | 19.632 | 1.00 | 67.01 | N |
| ATOM | 468 | CA | GLU | A | 598 | -23.190 | 29.228 | 19.702 | 1.00 | 66.05 | C |
| ATOM | 469 | CB | GLU | A | 598 | -24.168 | 29.448 | 18.535 | 1.00 | 66.46 | C |
| ATOM | 470 | CG | GLU | A | 598 | -23.566 | 29.178 | 17.144 | 1.00 | 68.68 | C |
| ATOM | 471 | CD | GLU | A | 598 | -23.984 | 30.211 | 16.085 | 1.00 | 71.36 | C |
| ATOM | 472 | OE1 | GLU | A | 598 | -25.018 | 30.885 | 16.283 | 1.00 | 72.82 | O |
| ATOM | 473 | OE2 | GLU | A | 598 | -23.274 | 30.355 | 15.056 | 1.00 | 71.83 | O |
| ATOM | 474 | C | GLU | A | 598 | -23.831 | 29.559 | 21.065 | 1.00 | 64.83 | C |
| ATOM | 475 | O | GLU | A | 598 | -24.714 | 30.423 | 21.144 | 1.00 | 64.99 | O |
| ATOM | 476 | N | ALA | A | 599 | -23.377 | 28.869 | 22.119 | 1.00 | 63.01 | N |
| ATOM | 477 | CA | ALA | A | 599 | -23.690 | 29.198 | 23.514 | 1.00 | 61.39 | C |
| ATOM | 478 | CB | ALA | A | 599 | -23.089 | 28.166 | 24.436 | 1.00 | 61.38 | C |
| ATOM | 479 | C | ALA | A | 599 | -23.169 | 30.601 | 23.885 | 1.00 | 60.46 | C |
| ATOM | 480 | O | ALA | A | 599 | -22.130 | 31.046 | 23.372 | 1.00 | 60.20 | O |
| ATOM | 481 | N | VAL | A | 600 | -23.882 | 31.284 | 24.785 | 1.00 | 58.75 | N |
| ATOM | 482 | CA | VAL | A | 600 | -23.605 | 32.702 | 25.090 | 1.00 | 56.46 | C |
| ATOM | 483 | CB | VAL | A | 600 | -24.906 | 33.470 | 25.476 | 1.00 | 56.52 | C |
| ATOM | 484 | CG1 | VAL | A | 600 | -24.599 | 34.905 | 25.936 | 1.00 | 55.85 | C |
| ATOM | 485 | CG2 | VAL | A | 600 | -25.880 | 33.475 | 24.307 | 1.00 | 56.52 | C |
| ATOM | 486 | C | VAL | A | 600 | -22.531 | 32.871 | 26.173 | 1.00 | 54.73 | C |
| ATOM | 487 | O | VAL | A | 600 | -22.720 | 32.456 | 27.319 | 1.00 | 55.01 | O |
| ATOM | 488 | N | LEU | A | 601 | -21.421 | 33.503 | 25.793 | 1.00 | 52.14 | N |
| ATOM | 489 | CA | LEU | A | 601 | -20.283 | 33.744 | 26.694 | 1.00 | 49.71 | C |
| ATOM | 490 | CB | LEU | A | 601 | -18.954 | 33.579 | 25.932 | 1.00 | 49.78 | C |
| ATOM | 491 | CG | LEU | A | 601 | -18.605 | 32.227 | 25.309 | 1.00 | 50.22 | C |
| ATOM | 492 | CD1 | LEU | A | 601 | -17.494 | 32.404 | 24.283 | 1.00 | 49.94 | C |
| ATOM | 493 | CD2 | LEU | A | 601 | -18.198 | 31.228 | 26.385 | 1.00 | 52.06 | C |
| ATOM | 494 | C | LEU | A | 601 | -20.306 | 35.139 | 27.326 | 1.00 | 47.55 | C |
| ATOM | 495 | O | LEU | A | 601 | -19.674 | 35.362 | 28.359 | 1.00 | 47.03 | O |
| ATOM | 496 | N | GLY | A | 602 | -20.988 | 36.074 | 26.664 | 1.00 | 44.71 | N |
| ATOM | 497 | CA | GLY | A | 602 | -21.212 | 37.410 | 27.204 | 1.00 | 42.39 | C |
| ATOM | 498 | C | GLY | A | 602 | -22.203 | 38.163 | 26.352 | 1.00 | 40.35 | C |
| ATOM | 499 | O | GLY | A | 602 | -22.343 | 37.888 | 25.159 | 1.00 | 40.34 | O |
| ATOM | 500 | N | GLU | A | 603 | -22.916 | 39.099 | 26.968 | 1.00 | 38.75 | N |
| ATOM | 501 | CA | GLU | A | 603 | -23.787 | 40.015 | 26.229 | 1.00 | 37.72 | C |
| ATOM | 502 | CB | GLU | A | 603 | -25.266 | 39.556 | 26.245 | 1.00 | 37.69 | C |
| ATOM | 503 | CG | GLU | A | 603 | -26.163 | 40.253 | 25.173 | 1.00 | 38.85 | C |
| ATOM | 504 | CD | GLU | A | 603 | -27.439 | 39.455 | 24.804 | 1.00 | 40.53 | C |

FIG. 3J

| ATOM | 505 | OE1 | GLU | A | 603 | -27.613 | 38.283 | 25.240 | 1.00 | 43.32 | O |
|---|---|---|---|---|---|---|---|---|---|---|---|
| ATOM | 506 | OE2 | GLU | A | 603 | -28.269 | 40.007 | 24.047 | 1.00 | 44.38 | O |
| ATOM | 507 | C | GLU | A | 603 | -23.605 | 41.407 | 26.825 | 1.00 | 36.10 | C |
| ATOM | 508 | O | GLU | A | 603 | -23.516 | 41.555 | 28.039 | 1.00 | 36.82 | O |
| ATOM | 509 | N | CYS | A | 604 | -23.540 | 42.419 | 25.971 | 1.00 | 33.65 | N |
| ATOM | 510 | CA | CYS | A | 604 | -23.101 | 43.745 | 26.382 | 1.00 | 31.95 | C |
| ATOM | 511 | CB | CYS | A | 604 | -21.603 | 43.944 | 26.032 | 1.00 | 31.89 | C |
| ATOM | 512 | SG | CYS | A | 604 | -20.431 | 42.852 | 26.867 | 1.00 | 32.03 | S |
| ATOM | 513 | C | CYS | A | 604 | -23.918 | 44.785 | 25.647 | 1.00 | 30.39 | C |
| ATOM | 514 | O | CYS | A | 604 | -23.944 | 44.785 | 24.429 | 1.00 | 29.50 | O |
| ATOM | 515 | N | ARG | A | 605 | -24.558 | 45.669 | 26.401 | 1.00 | 29.23 | N |
| ATOM | 516 | CA | ARG | A | 605 | -25.288 | 46.784 | 25.852 | 1.00 | 29.99 | C |
| ATOM | 517 | CB | ARG | A | 605 | -26.229 | 47.399 | 26.898 | 1.00 | 29.33 | C |
| ATOM | 518 | CG | ARG | A | 605 | -27.579 | 46.686 | 27.004 | 1.00 | 30.53 | C |
| ATOM | 519 | CD | ARG | A | 605 | -28.487 | 47.267 | 28.088 | 1.00 | 30.34 | C |
| ATOM | 520 | NE | ARG | A | 605 | -29.635 | 46.348 | 28.290 | 1.00 | 34.53 | N |
| ATOM | 521 | CZ | ARG | A | 605 | -30.792 | 46.429 | 27.629 | 1.00 | 37.09 | C |
| ATOM | 522 | NH1 | ARG | A | 605 | -31.010 | 47.398 | 26.724 | 1.00 | 35.96 | N |
| ATOM | 523 | NH2 | ARG | A | 605 | -31.741 | 45.538 | 27.864 | 1.00 | 35.84 | N |
| ATOM | 524 | C | ARG | A | 605 | -24.325 | 47.864 | 25.376 | 1.00 | 29.69 | C |
| ATOM | 525 | O | ARG | A | 605 | -23.495 | 48.327 | 26.139 | 1.00 | 29.12 | O |
| ATOM | 526 | N | VAL | A | 606 | -24.499 | 48.274 | 24.124 | 1.00 | 30.60 | N |
| ATOM | 527 | CA | VAL | A | 606 | -23.722 | 49.343 | 23.485 | 1.00 | 30.63 | C |
| ATOM | 528 | CB | VAL | A | 606 | -24.237 | 49.567 | 22.030 | 1.00 | 30.68 | C |
| ATOM | 529 | CG1 | VAL | A | 606 | -23.529 | 50.745 | 21.332 | 1.00 | 30.24 | C |
| ATOM | 530 | CG2 | VAL | A | 606 | -24.088 | 48.294 | 21.213 | 1.00 | 30.76 | C |
| ATOM | 531 | C | VAL | A | 606 | -23.720 | 50.628 | 24.336 | 1.00 | 31.49 | C |
| ATOM | 532 | O | VAL | A | 606 | -22.681 | 51.271 | 24.521 | 1.00 | 31.35 | O |
| ATOM | 533 | N | ARG | A | 607 | -24.860 | 50.990 | 24.921 | 1.00 | 31.22 | N |
| ATOM | 534 | CA | ARG | A | 607 | -24.886 | 52.178 | 25.779 | 1.00 | 31.97 | C |
| ATOM | 535 | CB | ARG | A | 607 | -26.331 | 52.478 | 26.238 | 1.00 | 33.01 | C |
| ATOM | 536 | CG | ARG | A | 607 | -26.827 | 51.535 | 27.323 | 1.00 | 35.91 | C |
| ATOM | 537 | CD | ARG | A | 607 | -28.316 | 51.741 | 27.530 | 1.00 | 43.97 | C |
| ATOM | 538 | NE | ARG | A | 607 | -28.609 | 52.904 | 28.359 | 1.00 | 48.01 | N |
| ATOM | 539 | CZ | ARG | A | 607 | -29.830 | 53.428 | 28.500 | 1.00 | 51.07 | C |
| ATOM | 540 | NH1 | ARG | A | 607 | -30.874 | 52.906 | 27.843 | 1.00 | 48.98 | N |
| ATOM | 541 | NH2 | ARG | A | 607 | -30.005 | 54.477 | 29.301 | 1.00 | 51.01 | N |
| ATOM | 542 | C | ARG | A | 607 | -23.949 | 52.125 | 26.997 | 1.00 | 31.14 | C |
| ATOM | 543 | O | ARG | A | 607 | -23.594 | 53.180 | 27.541 | 1.00 | 31.98 | O |
| ATOM | 544 | N | PHE | A | 608 | -23.552 | 50.920 | 27.447 | 1.00 | 30.09 | N |
| ATOM | 545 | CA | PHE | A | 608 | -22.649 | 50.831 | 28.582 | 1.00 | 28.86 | C |
| ATOM | 546 | CB | PHE | A | 608 | -23.189 | 49.894 | 29.671 | 1.00 | 29.49 | C |
| ATOM | 547 | CG | PHE | A | 608 | -24.473 | 50.383 | 30.298 | 1.00 | 30.60 | C |
| ATOM | 548 | CD1 | PHE | A | 608 | -24.525 | 51.619 | 30.932 | 1.00 | 31.13 | C |
| ATOM | 549 | CE1 | PHE | A | 608 | -25.722 | 52.101 | 31.504 | 1.00 | 33.70 | C |
| ATOM | 550 | CZ | PHE | A | 608 | -26.888 | 51.310 | 31.439 | 1.00 | 33.23 | C |
| ATOM | 551 | CE2 | PHE | A | 608 | -26.841 | 50.055 | 30.815 | 1.00 | 32.75 | C |
| ATOM | 552 | CD2 | PHE | A | 608 | -25.630 | 49.600 | 30.243 | 1.00 | 32.92 | C |
| ATOM | 553 | C | PHE | A | 608 | -21.207 | 50.469 | 28.188 | 1.00 | 28.41 | C |
| ATOM | 554 | O | PHE | A | 608 | -20.355 | 50.252 | 29.049 | 1.00 | 27.33 | O |
| ATOM | 555 | N | LEU | A | 609 | -20.959 | 50.406 | 26.884 | 1.00 | 27.47 | N |
| ATOM | 556 | CA | LEU | A | 609 | -19.605 | 50.245 | 26.372 | 1.00 | 28.08 | C |
| ATOM | 557 | CB | LEU | A | 609 | -19.637 | 49.618 | 24.969 | 1.00 | 27.97 | C |
| ATOM | 558 | CG | LEU | A | 609 | -18.297 | 49.131 | 24.356 | 1.00 | 27.52 | C |
| ATOM | 559 | CD1 | LEU | A | 609 | -18.573 | 48.167 | 23.226 | 1.00 | 28.80 | C |
| ATOM | 560 | CD2 | LEU | A | 609 | -17.487 | 50.310 | 23.861 | 1.00 | 26.25 | C |

FIG. 3K

```
ATOM    561  C    LEU A 609     -18.979  51.624  26.387  1.00 27.46           C
ATOM    562  O    LEU A 609     -19.428  52.516  25.691  1.00 28.23           O
ATOM    563  N    SER A 610     -17.985  51.831  27.236  1.00 27.62           N
ATOM    564  CA   SER A 610     -17.388  53.154  27.352  1.00 27.46           C
ATOM    565  CB   SER A 610     -16.876  53.380  28.765  1.00 26.84           C
ATOM    566  OG   SER A 610     -16.185  52.243  29.211  1.00 28.05           O
ATOM    567  C    SER A 610     -16.254  53.394  26.326  1.00 27.66           C
ATOM    568  O    SER A 610     -16.032  54.521  25.895  1.00 27.61           O
ATOM    569  N    PHE A 611     -15.543  52.338  25.942  1.00 28.24           N
ATOM    570  CA   PHE A 611     -14.300  52.507  25.139  1.00 28.18           C
ATOM    571  CB   PHE A 611     -13.131  52.865  26.077  1.00 28.20           C
ATOM    572  CG   PHE A 611     -11.818  53.151  25.384  1.00 28.78           C
ATOM    573  CD1  PHE A 611     -11.586  54.394  24.785  1.00 28.21           C
ATOM    574  CE1  PHE A 611     -10.364  54.676  24.173  1.00 30.35           C
ATOM    575  CZ   PHE A 611      -9.358  53.708  24.165  1.00 28.77           C
ATOM    576  CE2  PHE A 611      -9.573  52.465  24.761  1.00 28.45           C
ATOM    577  CD2  PHE A 611     -10.807  52.199  25.372  1.00 28.02           C
ATOM    578  C    PHE A 611     -13.979  51.242  24.398  1.00 27.97           C
ATOM    579  O    PHE A 611     -14.269  50.145  24.871  1.00 28.38           O
ATOM    580  N    LEU A 612     -13.373  51.383  23.229  1.00 27.84           N
ATOM    581  CA   LEU A 612     -12.849  50.235  22.514  1.00 27.70           C
ATOM    582  CB   LEU A 612     -13.848  49.726  21.474  1.00 28.51           C
ATOM    583  CG   LEU A 612     -14.239  50.736  20.384  1.00 30.11           C
ATOM    584  CD1  LEU A 612     -13.434  50.459  19.087  1.00 33.46           C
ATOM    585  CD2  LEU A 612     -15.691  50.673  20.102  1.00 32.82           C
ATOM    586  C    LEU A 612     -11.525  50.602  21.852  1.00 28.49           C
ATOM    587  O    LEU A 612     -11.230  51.802  21.618  1.00 27.56           O
ATOM    588  N    ALA A 613     -10.730  49.575  21.556  1.00 28.35           N
ATOM    589  CA   ALA A 613      -9.451  49.789  20.872  1.00 28.75           C
ATOM    590  CB   ALA A 613      -8.413  50.443  21.791  1.00 27.94           C
ATOM    591  C    ALA A 613      -8.882  48.541  20.302  1.00 28.56           C
ATOM    592  O    ALA A 613      -9.247  47.434  20.683  1.00 28.13           O
ATOM    593  N    VAL A 614      -7.953  48.731  19.374  1.00 28.96           N
ATOM    594  CA   VAL A 614      -7.135  47.640  18.915  1.00 29.19           C
ATOM    595  CB   VAL A 614      -6.881  47.722  17.372  1.00 29.99           C
ATOM    596  CG1  VAL A 614      -5.784  46.759  16.951  1.00 28.41           C
ATOM    597  CG2  VAL A 614      -8.186  47.375  16.603  1.00 29.96           C
ATOM    598  C    VAL A 614      -5.863  47.796  19.751  1.00 28.74           C
ATOM    599  O    VAL A 614      -5.455  48.920  20.025  1.00 28.56           O
ATOM    600  N    GLY A 615      -5.274  46.687  20.200  1.00 28.53           N
ATOM    601  CA   GLY A 615      -4.081  46.774  21.055  1.00 29.65           C
ATOM    602  C    GLY A 615      -2.835  47.036  20.204  1.00 30.44           C
ATOM    603  O    GLY A 615      -2.934  47.097  18.978  1.00 30.76           O
ATOM    604  N    ARG A 616      -1.673  47.186  20.840  1.00 30.40           N
ATOM    605  CA   ARG A 616      -0.433  47.456  20.110  1.00 30.95           C
ATOM    606  CB   ARG A 616       0.732  47.749  21.058  1.00 30.88           C
ATOM    607  CG   ARG A 616       0.492  48.922  21.948  1.00 30.13           C
ATOM    608  CD   ARG A 616       0.195  50.209  21.179  1.00 29.33           C
ATOM    609  NE   ARG A 616       0.078  51.324  22.110  1.00 29.83           N
ATOM    610  CZ   ARG A 616      -0.232  52.567  21.770  1.00 33.27           C
ATOM    611  NH1  ARG A 616      -0.489  52.864  20.505  1.00 33.66           N
ATOM    612  NH2  ARG A 616      -0.320  53.511  22.701  1.00 33.73           N
ATOM    613  C    ARG A 616      -0.102  46.320  19.172  1.00 31.50           C
ATOM    614  O    ARG A 616       0.407  46.553  18.097  1.00 32.79           O
ATOM    615  N    ASP A 617      -0.427  45.102  19.564  1.00 31.76           N
ATOM    616  CA   ASP A 617      -0.450  43.998  18.638  1.00 33.46           C
```

FIG. 3L

```
ATOM    617  CB   ASP A 617      -0.242  42.672  19.353  1.00 33.40      C
ATOM    618  CG   ASP A 617      -0.131  41.508  18.397  1.00 37.00      C
ATOM    619  OD1  ASP A 617      -1.018  41.345  17.548  1.00 36.91      O
ATOM    620  OD2  ASP A 617       0.848  40.722  18.503  1.00 41.81      O
ATOM    621  C    ASP A 617      -1.798  43.994  17.889  1.00 33.59      C
ATOM    622  O    ASP A 617      -2.875  43.906  18.502  1.00 31.75      O
ATOM    623  N    VAL A 618      -1.686  44.053  16.560  1.00 33.40      N
ATOM    624  CA   VAL A 618      -2.794  44.315  15.638  1.00 34.31      C
ATOM    625  CB   VAL A 618      -2.235  44.538  14.191  1.00 34.51      C
ATOM    626  CG1  VAL A 618      -1.878  43.204  13.534  1.00 33.81      C
ATOM    627  CG2  VAL A 618      -3.216  45.298  13.362  1.00 37.28      C
ATOM    628  C    VAL A 618      -3.874  43.229  15.673  1.00 33.73      C
ATOM    629  O    VAL A 618      -4.978  43.426  15.200  1.00 34.57      O
ATOM    630  N    HIS A 619      -3.547  42.081  16.236  1.00 33.90      N
ATOM    631  CA   HIS A 619      -4.514  40.999  16.418  1.00 34.73      C
ATOM    632  CB   HIS A 619      -3.775  39.711  16.723  1.00 35.52      C
ATOM    633  CG   HIS A 619      -2.843  39.265  15.640  1.00 37.50      C
ATOM    634  ND1  HIS A 619      -1.558  39.747  15.521  1.00 38.98      N
ATOM    635  CE1  HIS A 619      -0.972  39.171  14.489  1.00 40.16      C
ATOM    636  NE2  HIS A 619      -1.824  38.319  13.948  1.00 41.17      N
ATOM    637  CD2  HIS A 619      -3.003  38.360  14.649  1.00 38.81      C
ATOM    638  C    HIS A 619      -5.497  41.219  17.575  1.00 33.76      C
ATOM    639  O    HIS A 619      -6.546  40.576  17.648  1.00 33.94      O
ATOM    640  N    THR A 620      -5.143  42.096  18.494  1.00 33.08      N
ATOM    641  CA   THR A 620      -5.883  42.154  19.746  1.00 32.76      C
ATOM    642  CB   THR A 620      -4.977  42.468  20.964  1.00 31.93      C
ATOM    643  OG1  THR A 620      -4.336  43.725  20.771  1.00 31.98      O
ATOM    644  CG2  THR A 620      -3.938  41.362  21.214  1.00 32.36      C
ATOM    645  C    THR A 620      -6.990  43.200  19.675  1.00 31.96      C
ATOM    646  O    THR A 620      -6.774  44.319  19.194  1.00 32.10      O
ATOM    647  N    PHE A 621      -8.157  42.827  20.175  1.00 30.97      N
ATOM    648  CA   PHE A 621      -9.236  43.799  20.364  1.00 30.26      C
ATOM    649  CB   PHE A 621     -10.362  43.502  19.360  1.00 29.67      C
ATOM    650  CG   PHE A 621     -11.559  44.418  19.488  1.00 30.49      C
ATOM    651  CD1  PHE A 621     -11.459  45.781  19.176  1.00 33.08      C
ATOM    652  CE1  PHE A 621     -12.577  46.645  19.298  1.00 33.66      C
ATOM    653  CZ   PHE A 621     -13.786  46.132  19.735  1.00 29.48      C
ATOM    654  CE2  PHE A 621     -13.892  44.775  20.057  1.00 29.92      C
ATOM    655  CD2  PHE A 621     -12.775  43.921  19.927  1.00 30.88      C
ATOM    656  C    PHE A 621      -9.739  43.810  21.830  1.00 28.60      C
ATOM    657  O    PHE A 621      -9.841  42.765  22.449  1.00 28.63      O
ATOM    658  N    ALA A 622     -10.041  44.987  22.370  1.00 28.14      N
ATOM    659  CA   ALA A 622     -10.683  45.084  23.697  1.00 28.12      C
ATOM    660  CB   ALA A 622      -9.615  45.310  24.827  1.00 27.24      C
ATOM    661  C    ALA A 622     -11.729  46.173  23.748  1.00 27.39      C
ATOM    662  O    ALA A 622     -11.629  47.193  23.065  1.00 27.85      O
ATOM    663  N    PHE A 623     -12.747  45.963  24.563  1.00 27.00      N
ATOM    664  CA   PHE A 623     -13.650  47.056  24.890  1.00 26.45      C
ATOM    665  CB   PHE A 623     -14.979  47.002  24.090  1.00 26.06      C
ATOM    666  CG   PHE A 623     -15.796  45.751  24.312  1.00 28.41      C
ATOM    667  CD1  PHE A 623     -16.728  45.677  25.353  1.00 27.12      C
ATOM    668  CE1  PHE A 623     -17.510  44.508  25.543  1.00 30.38      C
ATOM    669  CZ   PHE A 623     -17.355  43.435  24.677  1.00 28.05      C
ATOM    670  CE2  PHE A 623     -16.430  43.519  23.620  1.00 28.49      C
ATOM    671  CD2  PHE A 623     -15.669  44.664  23.444  1.00 27.63      C
ATOM    672  C    PHE A 623     -13.872  47.075  26.381  1.00 25.63      C
```

FIG. 3M

| ATOM | 673 | O | PHE | A | 623 | -13.797 | 46.040 | 27.043 | 1.00 | 25.65 | O |
|---|---|---|---|---|---|---|---|---|---|---|---|
| ATOM | 674 | N | ILE | A | 624 | -14.121 | 48.258 | 26.908 | 1.00 | 25.38 | N |
| ATOM | 675 | CA | ILE | A | 624 | -14.407 | 48.410 | 28.322 | 1.00 | 25.47 | C |
| ATOM | 676 | CB | ILE | A | 624 | -13.603 | 49.570 | 28.948 | 1.00 | 25.41 | C |
| ATOM | 677 | CG1 | ILE | A | 624 | -12.094 | 49.316 | 28.763 | 1.00 | 24.63 | C |
| ATOM | 678 | CD1 | ILE | A | 624 | -11.197 | 50.544 | 29.213 | 1.00 | 25.99 | C |
| ATOM | 679 | CG2 | ILE | A | 624 | -13.961 | 49.793 | 30.456 | 1.00 | 23.35 | C |
| ATOM | 680 | C | ILE | A | 624 | -15.908 | 48.641 | 28.481 | 1.00 | 25.79 | C |
| ATOM | 681 | O | ILE | A | 624 | -16.502 | 49.448 | 27.786 | 1.00 | 25.32 | O |
| ATOM | 682 | N | MET | A | 625 | -16.498 | 47.891 | 29.394 | 1.00 | 26.45 | N |
| ATOM | 683 | CA | MET | A | 625 | -17.906 | 48.056 | 29.766 | 1.00 | 26.60 | C |
| ATOM | 684 | CB | MET | A | 625 | -18.554 | 46.678 | 29.842 | 1.00 | 27.03 | C |
| ATOM | 685 | CG | MET | A | 625 | -18.755 | 45.984 | 28.467 | 1.00 | 25.49 | C |
| ATOM | 686 | SD | MET | A | 625 | -19.878 | 46.848 | 27.351 | 1.00 | 30.31 | S |
| ATOM | 687 | CE | MET | A | 625 | -21.422 | 46.821 | 28.279 | 1.00 | 29.57 | C |
| ATOM | 688 | C | MET | A | 625 | -18.020 | 48.716 | 31.117 | 1.00 | 26.63 | C |
| ATOM | 689 | O | MET | A | 625 | -17.264 | 48.409 | 32.005 | 1.00 | 26.86 | O |
| ATOM | 690 | N | ALA | A | 626 | -18.958 | 49.636 | 31.285 | 1.00 | 27.70 | N |
| ATOM | 691 | CA | ALA | A | 626 | -19.329 | 50.039 | 32.628 | 1.00 | 29.34 | C |
| ATOM | 692 | CB | ALA | A | 626 | -19.952 | 51.407 | 32.607 | 1.00 | 28.58 | C |
| ATOM | 693 | C | ALA | A | 626 | -20.324 | 48.985 | 33.142 | 1.00 | 30.86 | C |
| ATOM | 694 | O | ALA | A | 626 | -21.538 | 49.091 | 32.886 | 1.00 | 31.60 | O |
| ATOM | 695 | N | ALA | A | 627 | -19.793 | 47.970 | 33.822 | 1.00 | 32.41 | N |
| ATOM | 696 | CA | ALA | A | 627 | -20.588 | 46.875 | 34.442 | 1.00 | 33.84 | C |
| ATOM | 697 | CB | ALA | A | 627 | -19.676 | 45.844 | 35.071 | 1.00 | 33.58 | C |
| ATOM | 698 | C | ALA | A | 627 | -21.588 | 47.387 | 35.480 | 1.00 | 34.95 | C |
| ATOM | 699 | O | ALA | A | 627 | -22.695 | 46.850 | 35.605 | 1.00 | 34.88 | O |
| ATOM | 700 | N | GLY | A | 628 | -21.166 | 48.417 | 36.213 | 1.00 | 36.05 | N |
| ATOM | 701 | CA | GLY | A | 628 | -22.013 | 49.200 | 37.103 | 1.00 | 37.83 | C |
| ATOM | 702 | C | GLY | A | 628 | -21.566 | 50.657 | 37.068 | 1.00 | 39.37 | C |
| ATOM | 703 | O | GLY | A | 628 | -20.645 | 50.996 | 36.325 | 1.00 | 39.01 | O |
| ATOM | 704 | N | PRO | A | 629 | -22.244 | 51.538 | 37.838 | 1.00 | 40.51 | N |
| ATOM | 705 | CA | PRO | A | 629 | -21.924 | 52.966 | 37.925 | 1.00 | 41.46 | C |
| ATOM | 706 | CB | PRO | A | 629 | -22.784 | 53.443 | 39.099 | 1.00 | 41.66 | C |
| ATOM | 707 | CG | PRO | A | 629 | -23.994 | 52.555 | 39.012 | 1.00 | 41.75 | C |
| ATOM | 708 | CD | PRO | A | 629 | -23.428 | 51.203 | 38.655 | 1.00 | 41.10 | C |
| ATOM | 709 | C | PRO | A | 629 | -20.446 | 53.242 | 38.193 | 1.00 | 41.92 | C |
| ATOM | 710 | O | PRO | A | 629 | -19.879 | 54.173 | 37.611 | 1.00 | 43.23 | O |
| ATOM | 711 | N | ALA | A | 630 | -19.806 | 52.433 | 39.031 | 1.00 | 41.70 | N |
| ATOM | 712 | CA | ALA | A | 630 | -18.383 | 52.680 | 39.321 | 1.00 | 40.74 | C |
| ATOM | 713 | CB | ALA | A | 630 | -18.222 | 53.200 | 40.754 | 1.00 | 41.41 | C |
| ATOM | 714 | C | ALA | A | 630 | -17.540 | 51.432 | 39.107 | 1.00 | 39.58 | C |
| ATOM | 715 | O | ALA | A | 630 | -16.569 | 51.205 | 39.826 | 1.00 | 39.24 | O |
| ATOM | 716 | N | SER | A | 631 | -17.926 | 50.626 | 38.124 | 1.00 | 37.79 | N |
| ATOM | 717 | CA | SER | A | 631 | -17.320 | 49.321 | 37.946 | 1.00 | 36.77 | C |
| ATOM | 718 | CB | SER | A | 631 | -18.253 | 48.259 | 38.547 | 1.00 | 37.01 | C |
| ATOM | 719 | OG | SER | A | 631 | -17.521 | 47.129 | 38.975 | 1.00 | 39.61 | O |
| ATOM | 720 | C | SER | A | 631 | -17.054 | 49.042 | 36.468 | 1.00 | 35.04 | C |
| ATOM | 721 | O | SER | A | 631 | -17.979 | 49.020 | 35.660 | 1.00 | 34.72 | O |
| ATOM | 722 | N | PHE | A | 632 | -15.789 | 48.822 | 36.118 | 1.00 | 33.25 | N |
| ATOM | 723 | CA | PHE | A | 632 | -15.419 | 48.627 | 34.714 | 1.00 | 31.45 | C |
| ATOM | 724 | CB | PHE | A | 632 | -14.500 | 49.761 | 34.215 | 1.00 | 31.01 | C |
| ATOM | 725 | CG | PHE | A | 632 | -15.077 | 51.118 | 34.465 | 1.00 | 30.52 | C |
| ATOM | 726 | CD1 | PHE | A | 632 | -16.112 | 51.598 | 33.673 | 1.00 | 29.73 | C |
| ATOM | 727 | CE1 | PHE | A | 632 | -16.685 | 52.842 | 33.927 | 1.00 | 31.92 | C |
| ATOM | 728 | CZ | PHE | A | 632 | -16.236 | 53.613 | 35.017 | 1.00 | 30.96 | C |

FIG. 3N

| | | | | | | | | | |
|---|---|---|---|---|---|---|---|---|---|
| ATOM | 729 | CE2 | PHE A 632 | -15.212 | 53.119 | 35.825 | 1.00 | 31.57 | C |
| ATOM | 730 | CD2 | PHE A 632 | -14.648 | 51.884 | 35.552 | 1.00 | 31.32 | C |
| ATOM | 731 | C | PHE A 632 | -14.837 | 47.262 | 34.441 | 1.00 | 30.88 | C |
| ATOM | 732 | O | PHE A 632 | -14.049 | 46.742 | 35.217 | 1.00 | 30.19 | O |
| ATOM | 733 | N | CYS A 633 | -15.238 | 46.701 | 33.312 | 1.00 | 30.46 | N |
| ATOM | 734 | CA | CYS A 633 | -14.811 | 45.377 | 32.919 | 1.00 | 30.74 | C |
| ATOM | 735 | CB | CYS A 633 | -16.050 | 44.440 | 32.959 | 1.00 | 29.64 | C |
| ATOM | 736 | SG | CYS A 633 | -15.745 | 42.754 | 32.507 | 1.00 | 33.94 | S |
| ATOM | 737 | C | CYS A 633 | -14.234 | 45.433 | 31.505 | 1.00 | 29.19 | C |
| ATOM | 738 | O | CYS A 633 | -14.858 | 45.971 | 30.618 | 1.00 | 30.33 | O |
| ATOM | 739 | N | CYS A 634 | -13.066 | 44.856 | 31.293 | 1.00 | 28.29 | N |
| ATOM | 740 | CA | CYS A 634 | -12.456 | 44.840 | 29.951 | 1.00 | 27.17 | C |
| ATOM | 741 | CB | CYS A 634 | -11.002 | 45.266 | 30.045 | 1.00 | 27.33 | C |
| ATOM | 742 | SG | CYS A 634 | -10.205 | 45.416 | 28.425 | 1.00 | 26.69 | S |
| ATOM | 743 | C | CYS A 634 | -12.563 | 43.467 | 29.262 | 1.00 | 26.48 | C |
| ATOM | 744 | O | CYS A 634 | -12.050 | 42.487 | 29.766 | 1.00 | 26.42 | O |
| ATOM | 745 | N | HIS A 635 | -13.249 | 43.412 | 28.119 | 1.00 | 25.87 | N |
| ATOM | 746 | CA | HIS A 635 | -13.421 | 42.176 | 27.351 | 1.00 | 26.81 | C |
| ATOM | 747 | CB | HIS A 635 | -14.836 | 42.117 | 26.771 | 1.00 | 27.11 | C |
| ATOM | 748 | CG | HIS A 635 | -15.907 | 42.021 | 27.823 | 1.00 | 26.94 | C |
| ATOM | 749 | ND1 | HIS A 635 | -16.504 | 40.829 | 28.173 | 1.00 | 28.99 | N |
| ATOM | 750 | CE1 | HIS A 635 | -17.395 | 41.047 | 29.123 | 1.00 | 29.70 | C |
| ATOM | 751 | NE2 | HIS A 635 | -17.409 | 42.342 | 29.392 | 1.00 | 29.08 | N |
| ATOM | 752 | CD2 | HIS A 635 | -16.475 | 42.969 | 28.601 | 1.00 | 27.56 | C |
| ATOM | 753 | C | HIS A 635 | -12.410 | 42.110 | 26.217 | 1.00 | 27.15 | C |
| ATOM | 754 | O | HIS A 635 | -12.272 | 43.070 | 25.483 | 1.00 | 26.58 | O |
| ATOM | 755 | N | MET A 636 | -11.724 | 40.980 | 26.066 | 1.00 | 28.35 | N |
| ATOM | 756 | CA | MET A 636 | -10.543 | 40.928 | 25.177 | 1.00 | 29.62 | C |
| ATOM | 757 | CB | MET A 636 | -9.278 | 40.841 | 26.024 | 1.00 | 29.24 | C |
| ATOM | 758 | CG | MET A 636 | -8.979 | 42.131 | 26.738 | 1.00 | 29.33 | C |
| ATOM | 759 | SD | MET A 636 | -7.884 | 41.963 | 28.164 | 1.00 | 31.19 | S |
| ATOM | 760 | CE | MET A 636 | -8.773 | 40.883 | 29.275 | 1.00 | 27.06 | C |
| ATOM | 761 | C | MET A 636 | -10.591 | 39.796 | 24.174 | 1.00 | 29.74 | C |
| ATOM | 762 | O | MET A 636 | -11.132 | 38.743 | 24.474 | 1.00 | 30.53 | O |
| ATOM | 763 | N | PHE A 637 | -10.038 | 40.031 | 22.983 | 1.00 | 30.44 | N |
| ATOM | 764 | CA | PHE A 637 | -10.127 | 39.078 | 21.870 | 1.00 | 31.47 | C |
| ATOM | 765 | CB | PHE A 637 | -11.257 | 39.486 | 20.883 | 1.00 | 31.61 | C |
| ATOM | 766 | CG | PHE A 637 | -12.611 | 39.667 | 21.536 | 1.00 | 31.86 | C |
| ATOM | 767 | CD1 | PHE A 637 | -12.939 | 40.871 | 22.144 | 1.00 | 28.50 | C |
| ATOM | 768 | CE1 | PHE A 637 | -14.179 | 41.047 | 22.774 | 1.00 | 30.24 | C |
| ATOM | 769 | CZ | PHE A 637 | -15.112 | 40.008 | 22.771 | 1.00 | 30.92 | C |
| ATOM | 770 | CE2 | PHE A 637 | -14.801 | 38.786 | 22.163 | 1.00 | 31.33 | C |
| ATOM | 771 | CD2 | PHE A 637 | -13.552 | 38.624 | 21.535 | 1.00 | 32.20 | C |
| ATOM | 772 | C | PHE A 637 | -8.816 | 38.999 | 21.082 | 1.00 | 32.19 | C |
| ATOM | 773 | O | PHE A 637 | -8.081 | 39.976 | 20.993 | 1.00 | 31.58 | O |
| ATOM | 774 | N | TRP A 638 | -8.546 | 37.826 | 20.512 | 1.00 | 33.61 | N |
| ATOM | 775 | CA | TRP A 638 | -7.476 | 37.668 | 19.529 | 1.00 | 34.73 | C |
| ATOM | 776 | CB | TRP A 638 | -6.547 | 36.512 | 19.908 | 1.00 | 34.99 | C |
| ATOM | 777 | CG | TRP A 638 | -5.352 | 36.403 | 18.991 | 1.00 | 35.06 | C |
| ATOM | 778 | CD1 | TRP A 638 | -5.290 | 35.734 | 17.805 | 1.00 | 35.04 | C |
| ATOM | 779 | NE1 | TRP A 638 | -4.037 | 35.868 | 17.241 | 1.00 | 35.85 | N |
| ATOM | 780 | CE2 | TRP A 638 | -3.263 | 36.642 | 18.065 | 1.00 | 36.07 | C |
| ATOM | 781 | CD2 | TRP A 638 | -4.061 | 36.995 | 19.186 | 1.00 | 36.08 | C |
| ATOM | 782 | CE3 | TRP A 638 | -3.504 | 37.806 | 20.184 | 1.00 | 36.27 | C |
| ATOM | 783 | CZ3 | TRP A 638 | -2.172 | 38.219 | 20.044 | 1.00 | 35.11 | C |
| ATOM | 784 | CH2 | TRP A 638 | -1.406 | 37.847 | 18.915 | 1.00 | 35.16 | C |

FIG. 3O

```
ATOM    785  CZ2 TRP A 638      -1.924  37.057  17.929  1.00 35.30           C
ATOM    786  C   TRP A 638      -8.122  37.405  18.169  1.00 34.91           C
ATOM    787  O   TRP A 638      -8.939  36.495  18.014  1.00 35.93           O
ATOM    788  N   CYS A 639      -7.788  38.227  17.197  1.00 35.79           N
ATOM    789  CA  CYS A 639      -8.434  38.156  15.898  1.00 37.13           C
ATOM    790  CB  CYS A 639      -9.174  39.457  15.606  1.00 36.48           C
ATOM    791  SG  CYS A 639     -10.212  40.086  16.954  1.00 35.98           S
ATOM    792  C   CYS A 639      -7.431  37.866  14.780  1.00 37.98           C
ATOM    793  O   CYS A 639      -6.371  38.468  14.721  1.00 38.44           O
ATOM    794  N   GLU A 640      -7.808  36.962  13.885  1.00 39.92           N
ATOM    795  CA  GLU A 640      -6.999  36.611  12.712  1.00 40.98           C
ATOM    796  CB  GLU A 640      -6.716  35.111  12.694  1.00 41.22           C
ATOM    797  CG  GLU A 640      -5.869  34.600  13.851  1.00 42.98           C
ATOM    798  CD  GLU A 640      -4.404  34.954  13.714  1.00 45.42           C
ATOM    799  OE1 GLU A 640      -4.006  35.480  12.645  1.00 46.78           O
ATOM    800  OE2 GLU A 640      -3.647  34.698  14.680  1.00 46.31           O
ATOM    801  C   GLU A 640      -7.758  36.991  11.441  1.00 41.43           C
ATOM    802  O   GLU A 640      -8.938  36.663  11.319  1.00 41.74           O
ATOM    803  N   PRO A 641      -7.088  37.664  10.481  1.00 41.71           N
ATOM    804  CA  PRO A 641      -5.655  37.989  10.441  1.00 41.18           C
ATOM    805  CB  PRO A 641      -5.428  38.351   8.972  1.00 41.65           C
ATOM    806  CG  PRO A 641      -6.751  38.900   8.508  1.00 42.03           C
ATOM    807  CD  PRO A 641      -7.810  38.183   9.298  1.00 41.93           C
ATOM    808  C   PRO A 641      -5.280  39.164  11.333  1.00 40.56           C
ATOM    809  O   PRO A 641      -4.110  39.336  11.683  1.00 40.51           O
ATOM    810  N   ASN A 642      -6.280  39.979  11.664  1.00 39.76           N
ATOM    811  CA  ASN A 642      -6.141  41.096  12.585  1.00 38.25           C
ATOM    812  CB  ASN A 642      -5.452  42.299  11.926  1.00 38.08           C
ATOM    813  CG  ASN A 642      -6.189  42.794  10.687  1.00 40.53           C
ATOM    814  OD1 ASN A 642      -7.410  43.000  10.708  1.00 42.71           O
ATOM    815  ND2 ASN A 642      -5.451  42.970   9.593  1.00 40.99           N
ATOM    816  C   ASN A 642      -7.526  41.468  13.118  1.00 37.32           C
ATOM    817  O   ASN A 642      -8.536  40.835  12.752  1.00 37.12           O
ATOM    818  N   ALA A 643      -7.564  42.503  13.953  1.00 35.93           N
ATOM    819  CA  ALA A 643      -8.797  42.941  14.609  1.00 35.60           C
ATOM    820  CB  ALA A 643      -8.478  43.446  16.032  1.00 34.13           C
ATOM    821  C   ALA A 643      -9.565  44.016  13.813  1.00 34.98           C
ATOM    822  O   ALA A 643     -10.487  44.639  14.357  1.00 35.16           O
ATOM    823  N   ALA A 644      -9.175  44.271  12.555  1.00 34.10           N
ATOM    824  CA  ALA A 644      -9.760  45.404  11.851  1.00 33.92           C
ATOM    825  CB  ALA A 644      -9.054  45.731  10.493  1.00 34.19           C
ATOM    826  C   ALA A 644     -11.273  45.239  11.692  1.00 33.76           C
ATOM    827  O   ALA A 644     -12.022  46.111  12.114  1.00 33.79           O
ATOM    828  N   SER A 645     -11.730  44.117  11.169  1.00 34.34           N
ATOM    829  CA  SER A 645     -13.166  43.989  10.914  1.00 35.29           C
ATOM    830  CB  SER A 645     -13.484  42.808  10.007  1.00 35.52           C
ATOM    831  OG  SER A 645     -13.377  41.591  10.695  1.00 41.42           O
ATOM    832  C   SER A 645     -14.038  44.025  12.190  1.00 34.60           C
ATOM    833  O   SER A 645     -15.080  44.667  12.194  1.00 33.43           O
ATOM    834  N   LEU A 646     -13.574  43.401  13.277  1.00 33.91           N
ATOM    835  CA  LEU A 646     -14.325  43.394  14.535  1.00 32.90           C
ATOM    836  CB  LEU A 646     -13.746  42.387  15.549  1.00 33.22           C
ATOM    837  CG  LEU A 646     -14.422  42.257  16.933  1.00 32.99           C
ATOM    838  CD1 LEU A 646     -15.929  41.935  16.865  1.00 31.59           C
ATOM    839  CD2 LEU A 646     -13.684  41.222  17.792  1.00 31.74           C
ATOM    840  C   LEU A 646     -14.402  44.772  15.144  1.00 33.28           C
```

FIG. 3P

| ATOM | 841 | O   | LEU A 646 | -15.490 | 45.222 | 15.520 | 1.00 | 33.40 | O |
|------|-----|-----|-----------|---------|--------|--------|------|-------|---|
| ATOM | 842 | N   | SER A 647 | -13.266 | 45.462 | 15.236 | 1.00 | 33.10 | N |
| ATOM | 843 | CA  | SER A 647 | -13.257 | 46.808 | 15.791 | 1.00 | 33.10 | C |
| ATOM | 844 | CB  | SER A 647 | -11.834 | 47.366 | 15.929 | 1.00 | 33.02 | C |
| ATOM | 845 | OG  | SER A 647 | -11.135 | 47.362 | 14.692 | 1.00 | 34.80 | O |
| ATOM | 846 | C   | SER A 647 | -14.129 | 47.765 | 14.976 | 1.00 | 33.75 | C |
| ATOM | 847 | O   | SER A 647 | -14.798 | 48.643 | 15.541 | 1.00 | 33.35 | O |
| ATOM | 848 | N   | GLU A 648 | -14.101 | 47.601 | 13.656 | 1.00 | 33.41 | N |
| ATOM | 849 | CA  | GLU A 648 | -14.932 | 48.397 | 12.747 | 1.00 | 34.85 | C |
| ATOM | 850 | CB  | GLU A 648 | -14.621 | 48.040 | 11.287 | 1.00 | 34.26 | C |
| ATOM | 851 | CG  | GLU A 648 | -13.392 | 48.741 | 10.742 | 1.00 | 38.34 | C |
| ATOM | 852 | CD  | GLU A 648 | -12.795 | 48.072 |  9.492 | 1.00 | 39.86 | C |
| ATOM | 853 | OE1 | GLU A 648 | -13.321 | 47.035 |  9.004 | 1.00 | 47.20 | O |
| ATOM | 854 | OE2 | GLU A 648 | -11.773 | 48.588 |  9.001 | 1.00 | 46.10 | O |
| ATOM | 855 | C   | GLU A 648 | -16.414 | 48.186 | 13.034 | 1.00 | 32.85 | C |
| ATOM | 856 | O   | GLU A 648 | -17.151 | 49.154 | 13.189 | 1.00 | 32.60 | O |
| ATOM | 857 | N   | ALA A 649 | -16.824 | 46.920 | 13.099 | 1.00 | 32.32 | N |
| ATOM | 858 | CA  | ALA A 649 | -18.211 | 46.526 | 13.392 | 1.00 | 32.59 | C |
| ATOM | 859 | CB  | ALA A 649 | -18.361 | 45.003 | 13.365 | 1.00 | 32.24 | C |
| ATOM | 860 | C   | ALA A 649 | -18.665 | 47.084 | 14.731 | 1.00 | 32.28 | C |
| ATOM | 861 | O   | ALA A 649 | -19.741 | 47.654 | 14.826 | 1.00 | 33.07 | O |
| ATOM | 862 | N   | VAL A 650 | -17.826 | 46.965 | 15.761 | 1.00 | 31.91 | N |
| ATOM | 863 | CA  | VAL A 650 | -18.202 | 47.466 | 17.084 | 1.00 | 31.38 | C |
| ATOM | 864 | CB  | VAL A 650 | -17.323 | 46.882 | 18.209 | 1.00 | 31.79 | C |
| ATOM | 865 | CG1 | VAL A 650 | -17.674 | 47.532 | 19.573 | 1.00 | 30.57 | C |
| ATOM | 866 | CG2 | VAL A 650 | -17.472 | 45.362 | 18.234 | 1.00 | 30.81 | C |
| ATOM | 867 | C   | VAL A 650 | -18.215 | 48.987 | 17.127 | 1.00 | 31.23 | C |
| ATOM | 868 | O   | VAL A 650 | -19.132 | 49.592 | 17.693 | 1.00 | 30.13 | O |
| ATOM | 869 | N   | GLN A 651 | -17.212 | 49.620 | 16.523 | 1.00 | 30.30 | N |
| ATOM | 870 | CA  | GLN A 651 | -17.262 | 51.077 | 16.439 | 1.00 | 30.08 | C |
| ATOM | 871 | CB  | GLN A 651 | -16.021 | 51.644 | 15.759 | 1.00 | 30.19 | C |
| ATOM | 872 | CG  | GLN A 651 | -15.935 | 53.160 | 15.861 | 1.00 | 28.82 | C |
| ATOM | 873 | CD  | GLN A 651 | -14.955 | 53.739 | 14.864 | 1.00 | 31.16 | C |
| ATOM | 874 | OE1 | GLN A 651 | -14.337 | 53.005 | 14.100 | 1.00 | 33.15 | O |
| ATOM | 875 | NE2 | GLN A 651 | -14.819 | 55.050 | 14.858 | 1.00 | 32.87 | N |
| ATOM | 876 | C   | GLN A 651 | -18.518 | 51.566 | 15.685 | 1.00 | 29.39 | C |
| ATOM | 877 | O   | GLN A 651 | -19.158 | 52.529 | 16.111 | 1.00 | 29.70 | O |
| ATOM | 878 | N   | ALA A 652 | -18.843 | 50.919 | 14.565 | 1.00 | 29.24 | N |
| ATOM | 879 | CA  | ALA A 652 | -20.030 | 51.298 | 13.776 | 1.00 | 28.09 | C |
| ATOM | 880 | CB  | ALA A 652 | -20.139 | 50.448 | 12.520 | 1.00 | 27.66 | C |
| ATOM | 881 | C   | ALA A 652 | -21.318 | 51.196 | 14.612 | 1.00 | 28.18 | C |
| ATOM | 882 | O   | ALA A 652 | -22.132 | 52.100 | 14.593 | 1.00 | 27.86 | O |
| ATOM | 883 | N   | ALA A 653 | -21.451 | 50.116 | 15.387 | 1.00 | 27.73 | N |
| ATOM | 884 | CA  | ALA A 653 | -22.584 | 49.938 | 16.282 | 1.00 | 27.99 | C |
| ATOM | 885 | CB  | ALA A 653 | -22.481 | 48.565 | 17.008 | 1.00 | 28.11 | C |
| ATOM | 886 | C   | ALA A 653 | -22.732 | 51.089 | 17.274 | 1.00 | 28.08 | C |
| ATOM | 887 | O   | ALA A 653 | -23.841 | 51.602 | 17.461 | 1.00 | 27.41 | O |
| ATOM | 888 | N   | CYS A 654 | -21.620 | 51.510 | 17.903 | 1.00 | 27.68 | N |
| ATOM | 889 | CA  | CYS A 654 | -21.627 | 52.664 | 18.817 | 1.00 | 28.26 | C |
| ATOM | 890 | CB  | CYS A 654 | -20.240 | 52.879 | 19.469 | 1.00 | 28.71 | C |
| ATOM | 891 | SG  | CYS A 654 | -19.659 | 51.477 | 20.517 | 1.00 | 29.78 | S |
| ATOM | 892 | C   | CYS A 654 | -22.066 | 53.983 | 18.164 | 1.00 | 28.63 | C |
| ATOM | 893 | O   | CYS A 654 | -22.780 | 54.771 | 18.779 | 1.00 | 28.06 | O |
| ATOM | 894 | N   | MET A 655 | -21.580 | 54.238 | 16.947 | 1.00 | 29.18 | N |
| ATOM | 895 | CA  | MET A 655 | -21.862 | 55.480 | 16.232 | 1.00 | 30.91 | C |
| ATOM | 896 | CB  | MET A 655 | -20.887 | 55.641 | 15.044 | 1.00 | 30.48 | C |

FIG. 3Q

```
ATOM    897  CG   MET A 655     -19.428  55.889  15.463  1.00 31.59       C
ATOM    898  SD   MET A 655     -18.277  56.236  14.097  1.00 34.16       S
ATOM    899  CE   MET A 655     -18.311  54.679  13.315  1.00 28.65       C
ATOM    900  C    MET A 655     -23.323  55.526  15.735  1.00 30.78       C
ATOM    901  O    MET A 655     -23.958  56.569  15.765  1.00 30.72       O
ATOM    902  N    LEU A 656     -23.831  54.386  15.279  1.00 32.18       N
ATOM    903  CA   LEU A 656     -25.254  54.236  14.920  1.00 33.98       C
ATOM    904  CB   LEU A 656     -25.496  52.832  14.393  1.00 34.15       C
ATOM    905  CG   LEU A 656     -25.589  52.432  12.939  1.00 39.72       C
ATOM    906  CD1  LEU A 656     -26.066  50.980  12.932  1.00 42.40       C
ATOM    907  CD2  LEU A 656     -26.576  53.299  12.153  1.00 42.32       C
ATOM    908  C    LEU A 656     -26.168  54.448  16.137  1.00 33.50       C
ATOM    909  O    LEU A 656     -27.165  55.177  16.082  1.00 32.69       O
ATOM    910  N    ARG A 657     -25.807  53.779  17.225  1.00 33.67       N
ATOM    911  CA   ARG A 657     -26.523  53.837  18.486  1.00 34.33       C
ATOM    912  CB   ARG A 657     -25.821  52.943  19.495  1.00 34.53       C
ATOM    913  CG   ARG A 657     -26.495  52.869  20.832  1.00 37.88       C
ATOM    914  CD   ARG A 657     -27.796  52.120  20.782  1.00 43.32       C
ATOM    915  NE   ARG A 657     -28.469  52.326  22.057  1.00 51.60       N
ATOM    916  CZ   ARG A 657     -29.726  51.984  22.322  1.00 54.68       C
ATOM    917  NH1  ARG A 657     -30.488  51.392  21.390  1.00 54.53       N
ATOM    918  NH2  ARG A 657     -30.216  52.245  23.529  1.00 54.75       N
ATOM    919  C    ARG A 657     -26.649  55.243  19.055  1.00 34.69       C
ATOM    920  O    ARG A 657     -27.720  55.633  19.547  1.00 34.18       O
ATOM    921  N    TYR A 658     -25.562  56.005  19.005  1.00 33.90       N
ATOM    922  CA   TYR A 658     -25.583  57.358  19.525  1.00 34.59       C
ATOM    923  CB   TYR A 658     -24.169  57.934  19.556  1.00 34.42       C
ATOM    924  CG   TYR A 658     -24.093  59.386  19.951  1.00 34.94       C
ATOM    925  CD1  TYR A 658     -24.500  59.817  21.223  1.00 34.57       C
ATOM    926  CE1  TYR A 658     -24.423  61.163  21.583  1.00 35.32       C
ATOM    927  CZ   TYR A 658     -23.935  62.084  20.664  1.00 35.71       C
ATOM    928  OH   TYR A 658     -23.832  63.415  20.987  1.00 37.00       O
ATOM    929  CE2  TYR A 658     -23.525  61.679  19.402  1.00 36.65       C
ATOM    930  CD2  TYR A 658     -23.611  60.340  19.050  1.00 34.93       C
ATOM    931  C    TYR A 658     -26.546  58.271  18.749  1.00 35.31       C
ATOM    932  O    TYR A 658     -27.289  59.063  19.344  1.00 34.08       O
ATOM    933  N    GLN A 659     -26.543  58.152  17.427  1.00 36.64       N
ATOM    934  CA   GLN A 659     -27.469  58.934  16.609  1.00 38.18       C
ATOM    935  CB   GLN A 659     -27.133  58.838  15.119  1.00 37.56       C
ATOM    936  CG   GLN A 659     -27.957  59.797  14.230  1.00 40.32       C
ATOM    937  CD   GLN A 659     -27.895  61.273  14.673  1.00 45.05       C
ATOM    938  OE1  GLN A 659     -26.847  61.780  15.085  1.00 46.81       O
ATOM    939  NE2  GLN A 659     -29.023  61.966  14.570  1.00 47.71       N
ATOM    940  C    GLN A 659     -28.936  58.521  16.876  1.00 39.29       C
ATOM    941  O    GLN A 659     -29.833  59.376  16.958  1.00 38.37       O
ATOM    942  N    LYS A 660     -29.168  57.220  17.011  1.00 40.98       N
ATOM    943  CA   LYS A 660     -30.510  56.723  17.352  1.00 43.19       C
ATOM    944  CB   LYS A 660     -30.583  55.206  17.294  1.00 42.96       C
ATOM    945  CG   LYS A 660     -30.997  54.731  15.909  1.00 46.37       C
ATOM    946  CD   LYS A 660     -30.893  53.224  15.763  1.00 50.01       C
ATOM    947  CE   LYS A 660     -30.466  52.815  14.343  1.00 51.48       C
ATOM    948  NZ   LYS A 660     -29.908  51.416  14.353  1.00 51.91       N
ATOM    949  C    LYS A 660     -31.040  57.273  18.672  1.00 43.84       C
ATOM    950  O    LYS A 660     -32.203  57.671  18.750  1.00 44.21       O
ATOM    951  N    CYS A 661     -30.175  57.339  19.677  1.00 45.01       N
ATOM    952  CA   CYS A 661     -30.516  57.920  20.974  1.00 46.89       C
```

FIG. 3R

```
ATOM    953  CB  CYS A 661     -29.472  57.533  22.030  1.00 46.61           C
ATOM    954  SG  CYS A 661     -29.435  55.702  22.312  1.00 48.96           S
ATOM    955  C   CYS A 661     -30.786  59.430  20.950  1.00 48.19           C
ATOM    956  O   CYS A 661     -31.763  59.889  21.553  1.00 48.16           O
ATOM    957  N   LEU A 662     -29.941  60.200  20.258  1.00 49.41           N
ATOM    958  CA  LEU A 662     -30.199  61.625  20.055  1.00 51.08           C
ATOM    959  CB  LEU A 662     -29.102  62.289  19.218  1.00 50.22           C
ATOM    960  CG  LEU A 662     -27.783  62.627  19.904  1.00 49.78           C
ATOM    961  CD1 LEU A 662     -26.879  63.325  18.913  1.00 49.09           C
ATOM    962  CD2 LEU A 662     -27.987  63.488  21.135  1.00 48.81           C
ATOM    963  C   LEU A 662     -31.549  61.844  19.380  1.00 52.54           C
ATOM    964  O   LEU A 662     -32.306  62.721  19.782  1.00 52.57           O
ATOM    965  N   ASP A 663     -31.821  61.040  18.352  1.00 54.79           N
ATOM    966  CA  ASP A 663     -33.063  61.094  17.584  1.00 57.33           C
ATOM    967  CB  ASP A 663     -32.984  60.179  16.366  1.00 57.71           C
ATOM    968  CG  ASP A 663     -32.964  60.947  15.064  1.00 60.51           C
ATOM    969  OD1 ASP A 663     -32.375  62.058  15.039  1.00 61.61           O
ATOM    970  OD2 ASP A 663     -33.551  60.434  14.071  1.00 63.95           O
ATOM    971  C   ASP A 663     -34.310  60.750  18.383  1.00 58.45           C
ATOM    972  O   ASP A 663     -35.327  61.430  18.256  1.00 58.71           O
ATOM    973  N   ALA A 664     -34.229  59.684  19.178  1.00 59.88           N
ATOM    974  CA  ALA A 664     -35.313  59.294  20.080  1.00 61.29           C
ATOM    975  CB  ALA A 664     -34.937  58.043  20.869  1.00 61.03           C
ATOM    976  C   ALA A 664     -35.678  60.442  21.027  1.00 62.49           C
ATOM    977  O   ALA A 664     -36.843  60.809  21.136  1.00 62.76           O
ATOM    978  N   ARG A 665     -34.673  61.030  21.668  1.00 63.62           N
ATOM    979  CA  ARG A 665     -34.889  62.055  22.686  1.00 65.35           C
ATOM    980  CB  ARG A 665     -33.759  61.996  23.728  1.00 65.20           C
ATOM    981  CG  ARG A 665     -33.562  60.563  24.272  1.00 66.62           C
ATOM    982  CD  ARG A 665     -32.638  60.440  25.483  1.00 66.98           C
ATOM    983  NE  ARG A 665     -32.783  59.115  26.099  1.00 71.00           N
ATOM    984  CZ  ARG A 665     -33.306  58.880  27.307  1.00 72.94           C
ATOM    985  NH1 ARG A 665     -33.724  59.883  28.074  1.00 74.11           N
ATOM    986  NH2 ARG A 665     -33.403  57.631  27.759  1.00 73.49           N
ATOM    987  C   ARG A 665     -35.115  63.485  22.152  1.00 65.84           C
ATOM    988  O   ARG A 665     -35.423  64.392  22.925  1.00 66.29           O
ATOM    989  N   SER A 666     -34.990  63.687  20.841  1.00 66.49           N
ATOM    990  CA  SER A 666     -35.189  65.014  20.255  1.00 66.99           C
ATOM    991  CB  SER A 666     -34.366  65.173  18.974  1.00 67.10           C
ATOM    992  OG  SER A 666     -34.904  64.392  17.921  1.00 67.35           O
ATOM    993  C   SER A 666     -36.668  65.308  19.978  1.00 67.28           C
ATOM    994  O   SER A 666     -37.398  64.459  19.462  1.00 67.48           O
```

CRYSTAL FORM OF THE AMYLOID PRECURSOR PROTEIN INTRACELLULAR DOMAIN (AICD) IN COMPLEX WITH HUMAN FE65-PTB2

The present invention relates to a three-dimensional structure of the intracellular domain (AICD) of human amyloid precursor protein (APP695) in complex with human Fe65-PTB2 (i.e. a protein-complex comprising the intracellular domain (AICD) of human amyloid precursor protein (APP695) and the human Fe65-PTB2), as well as to methods and uses of said three-dimensional structure for identifying ligands which modify the interaction between the AICD and the Fe65-PTB2. Moreover, the present invention relates to pharmaceutical compositions which contain one or more of such identified ligands for the prevention or treatment of neurodegenerative disorders.

Alzheimer's disease (AD) is a neurodegenerative disorder and the major cause of senile dementia in the present world especially in the elder population. Worldwide approximately 18 million people are affected and it is predicted by the World Health Organization (WHO) that this number will nearly double until the year 2025. The immense number of people requiring steady care will severely burden medical, monetary, and human resources especially in the light of the increasing generation gap.

Pathologically, AD is characterized by the formation of senile plaques and neurofibrillary tangles in the brain accompanied by a substantial neuronal and synaptic loss in the neocortex, which is likely to represent the main reason for cognitive impairment in AD. However, the underlying mechanisms are complex and remain still unclear. Strong biochemical and genetic evidence support the hypothesis that accumulation of the amyloid-β peptide (Aβ), the main constituent of senile plaques is a central event in AD pathogenesis. Aβ formation results from sequential cleavage of its precursor protein (APP) an integral and ubiquitously expressed type I transmembrane protein by the β-site cleaving enzyme 1 (BACE1) and the γ-secretase complex. Aβ has been shown to be neurotoxic with pro-apoptotic effects.

As a consequence of the γ-secretase cleavage (ε-cleavage) the C-terminal 49-50 amino acids intracellular domain of APP (AICD or C49-50, respectively) is liberated into the cytosol. Many of the identified binding partners of APP interact with the AICD modulating transport and signaling events. The AICD can be further proteolytically cleaved by caspases at residue D664 (residue numbering in the following corresponds to the neuronal APP spliceform APP695) by caspases generating a strong neurotoxic peptide comprising the C-terminal 31 amino acids (AICD-C31) of APP, that could be linked to increased synaptic loss and apoptotic cell death in Alzheimer's disease.

Both the AICD and the AICD-C31 are natively unstructured when not bound to a binding partner. They contain the highly conserved Y682ENPTY motif where several adaptor proteins like members of the Fe65, X11 18, Jip and Shc families, the Notch inhibitor Numb, and mammalian disabled (mDab) bind via their phosphotyrosine binding domains (PTB). Additionally, AICD contains the basolateral sorting signal Y653TSI which was shown to interact with the microtubule-interacting protein PAT1.

The APP-interacting protein that has generated the most interest is Fe65, since knock-out studies in worms and mice resulted in phenotypes strikingly similar to those seen when APP genes were knocked-out, emphasizing the close functional relationship between both proteins. Fe65 is a brain enriched adaptor protein important for brain development containing one WW domain and two PTB domains. The N-terminal located PTB domain (PTB1) has been shown to interact with a variety of proteins involved in translocation and nuclear signaling of APP, while the C-terminal PTB domain (PTB2) binds to the AICD of APP and the other two members of the APP family (APLP 1 and 2). Binding of Fe65 to the AICD influences APP processing and Aβ generation.

The AICD contains eight putative phosphorylation sites with seven of them being phosphorylated in AD brains. The most important and also brain limited phosphorylation mediated by several kinases occurs at threonine T668.

Phosphorylation of T668 is a normal process linked to neurite extension, anterograde transport of vesicular cargo, nuclear signaling, and regulation of Fe65 binding. In contrast, increased phosphorylation of APP is a pathological trait of AD as it facilitates BACE1 cleavage of APP and increases Aβ generation. Within the Y682ENPTY motif only the phosphorylation of Y682 is known to play a role as it facilitates binding of ShcA, ShcC, and Grb2 to APP. The classical PTB-interacting phosphorylation site (Y687) is not used in APP.

Since the interaction of the human adaptor protein Fe65 with the amyloid precursor protein intracellular domain (AICD) plays a key role in the accumulation of the amyloid-β peptide (Aβ) in cerebral plaques, the modification of the interaction between said AICD and Fe65, in particular Fe65-PTB2, is likely to prevent or at least reduce the formation of such plaques. However, for identification and/or development of effective ligands the exact mode of interaction between AICD and Fe65 needs to be determined.

Therefore, the technical problem underlying the present invention is to provide a new system on the molecular/atomic level, which is suited to elucidate the binding mode between AICD and Fe65 and to enable the identification and/or development of ligands which negatively or positively affect the interaction between both AICD and Fe65.

The above-mentioned technical problem is solved by providing the embodiments characterized in the claims.

In particular, there is provided a protein-complex comprising the intracellular domain (AICD) of human amyloid precursor protein (APP695) and the human Fe65-PTB2 (i.e. a three-dimensional structure of AICD of APP695 in complex with human Fe65-PTB2), or at least those parts thereof which characterize the interaction between the AICD and the Fe65-PTB2.

The expression "three-dimensional structure" as used according to the present invention is not especially restricted and generally relates to the molecular geometry which may for example be understood as the spatial arrangement of atoms in one or more molecules and the bonds between the atoms, such as covalent, ionic, hydrogen bridge or van-der-Waals bonds. Moreover, said expression "three-dimensional structure" further includes images of said structure, such as computer-generated images showing the structural arrangements of atoms, bonds, electronic surfaces, hydrophilic/hydrophobic surfaces, or combinations thereof.

The term "AICD" as used herein is not only limited to the complete intracellular domain of the APP, i.e. the C-terminal 49-50 amino acids of said APP, but also further includes fragments thereof such as the neurotoxic fragment AICD-C31 which comprises the 31 C-terminal amino acids of the APP.

The term "Fe65-PTB2" as used in the present invention is not only limited to the C-terminal phosphotyrosine binding domain of human Fe65 (PTB2) but may also include other components of Fe65 such as the binding domains PTB1 or WW, as long as the PTB2 domain or a fragment thereof capable of interacting with AICD, is present.

According to the present invention, the molecules "AICD" and "Fe65" further include additional moieties bound thereto or in complex therewith, such as marker or linker molecules, molecules affecting purification or crystallization, or molecules which improve the biocompatibility. Examples of such molecules are fluorescent or radioactive markers, purification tags such as His-tags, heavy atoms for improved electron density in crystallization experiments, salts, sugars, or amino acid and nucleic acid residues.

Furthermore, herein, the term "interaction" means any kind of action that occurs as two or more independent entities have an effect upon one another. For example, the term "interaction" includes attractive and repulsive effects between two or more molecules.

Another embodiment of the present invention relates to the three-dimensional structure as defined above, wherein the AICD comprises an amino acid sequence having at least 40%, preferably 60%, and more preferably 80% identity with the sequence of SEQ ID NO: 1, and the human Fe65-PTB2 comprises an amino acid sequence having at least 40%, preferably 60%, and more preferably 80% identity with the sequence of SEQ ID NO: 2.

According to the present invention, the expression "at least 40% identity" refers to sequences which are least 40% identical with the amino acid sequences of SEQ ID NOs: 1 and/or 2, as long as the deviation from said sequences of SEQ ID NOs: 1 and/or 2 does not eliminate the interaction between AICD and Fe65-PTB2. Furthermore, minor sequence modifications such as addition, deletion or substitution of one or more amino acid(s) are also included herein, as long as said modifications do not qualitatively alter the binding properties of AICD and Fe65-PTB2. The same definition applies for the expressions "preferably 60% identity" and "more preferably 80% identity" as mentioned above.

According to another aspect, the present invention relates to a three-dimensional structure as defined above, comprising the atomic coordinates provided in FIG. 1, or at least those parts thereof which characterize the interaction between AICD and Fe65-PTB2.

Herein, the term "atomic coordinates" refers to the coordinates shown in FIGS. 1 to 3 as a whole, but also includes parts thereof, which are e.g. suitable for identifying and/or developing ligands which interact with one or more binding sites of the molecule(s) characterized by said atomic coordinates. Moreover, the term "atomic coordinates" does not only include the exact coordinates as provided in FIGS. 1 to 3, but also includes those atomic coordinates which are substantially identical thereto, and which may have one or more atoms removed, altered or added. Accordingly, also those atomic coordinates which deviate from those provided in FIGS. 1 to 3 should fall under the above-mentioned term "atomic coordinates", as long as the same principal interaction mode between AICD and Fe65-PTB2, or at least a similar sterical predisposition of the respective binding sites thereof, is characterized.

In a further embodiment of the present invention, a three-dimensional structure of AICD containing at least that part which characterizes the above-mentioned interaction between AICD and Fe65-PTB2 is disclosed.

According to a preferred embodiment of the present invention, the above-defined three-dimensional structure of AICD comprises the atomic coordinates provided in FIG. 2, or at least those parts thereof which characterize the binding site(s) of the AICD.

Another embodiment of the present invention relates to a three-dimensional structure of Fe65-PTB2 containing at least that part which characterizes the interaction between Fe65-PTB2 and AICD as defined above.

In a further preferred embodiment, the above-defined three-dimensional structure of Fe65-PTB2 is disclosed, comprising the atomic coordinates provided in FIG. 3, or at least those parts thereof which characterize the binding site(s) of the Fe65-PTB2.

Another aspect of the present invention relates to a method for identifying and/or developing ligands which modify the interaction of Fe65-PTB2 and AICD, or fragments thereof, comprising the steps of (a) providing a protein-complex comprising the intracellular domain (AICD) of human amyloid precursor protein (APP695) and the human Fe65-PTB2 by its three-dimensional structure comprising the atomic coordinates provided in FIG. 1 (i.e. providing a three-dimensional structure comprising the atomic coordinates provided in FIG. 1), or at least those parts thereof which characterize the interaction between Fe65-PTB2 and AICD, and (b) determining ligands which modify the interaction between AICD and Fe65-PTB2, or fragments thereof.

The term "modify" is not especially limited herein and includes all alteration of the interaction of Fe65-PTB2 and AICD, or fragments thereof. In particular, the term "modify" includes for example impairment, inhibition, enhancement or change of specificity.

A further aspect of the present invention relates to a method for identifying and/or developing ligands which interact with the binding site(s) of AICD, or fragments thereof, comprising the steps of (a) providing AICD by its three-dimensional structure comprising the atomic coordinates provided in FIG. 2 (i.e. providing a three-dimensional structure comprising the atomic coordinates provided in FIG. 2), or at least those parts thereof which characterize the binding site(s) of AICD, and (b) determining ligands which interact with the binding site(s) of AICD, or fragments thereof.

Moreover, another aspect of the present invention relates to a method for identifying and/or developing ligands which interact with the binding site(s) of Fe65-PTB2, or fragments thereof, comprising the steps of (a) providing Fe65-PTB2 by its three-dimensional structure comprising the atomic coordinates provided in FIG. 3 (i.e. providing a three-dimensional structure comprising the atomic coordinates provided in FIG. 3), or at least those parts thereof which characterize the binding site(s) of Fe65-PTB2, and (b) determining ligands which interact with the binding site(s) of Fe65-PTB2, or fragments thereof.

According to a preferred embodiment of the above-defined method the three-dimensional structure is provided in a computer-readable form, and the ligands which modify the interaction between AICD and Fe65-PTB2, or interact with the binding sites of AICD and/or Fe65-PTB2, or fragments thereof, are determined using a suitable computer-program.

The term "computer-readable form" as used herein is not especially restricted and refers to any form which might be processed by a computer. Preferably, the three-dimensional structure is provided in a form of coordinates or images. Similarly, the term "suitable computer program" herein includes all computer-programs which can be used in connection with the above-mentioned computer-readable form of the three-dimensional structure of the present invention and includes e.g. programs for visualizing the structure or parts thereof, for simulating, optimizing and determining binding interactions, or for screening tasks in general.

The method as defined above is thus especially suited to identify and/or develop ligands by at least partly using in silico methods. The term "in silico" as used herein means inter alia that an action is performed on a computer, via computer simulation, or includes at least an involvement of a computer.

Another aspect of the present invention relates to a use of the above-defined protein-complex, AICD, or Fe65-PTB2 for identifying and/or developing ligands which modify the interaction of Fe65-PTB2 and AICD, or fragments thereof, wherein the three-dimensional structure thereof comprises the atomic coordinates provided in FIG. 1, 2 or 3, or at least those parts thereof which describe the interaction between Fe65-PTB2 and AICD.

According to another embodiment, a pharmaceutical composition to be used for the treatment or prevention of neuronal disorders in a patient, such as AD or neurodegenerative disorders associated with AD in a mammal, preferably a human, is disclosed, comprising a substance capable of modifying the interaction between Fe65-PTB2 and AICD, which has been identified by the above-defined methods, and optionally one or more pharmaceutically acceptable carriers and/or diluents.

The term "pharmaceutical composition" generally includes, according to the present invention, all compositions comprising at least one constituent which has an effect on a condition of a patient suffering from AD or a neurodegenerative disorder associated with AD or which can be used to prevent such disorders. Accordingly, said term is not specifically restricted and includes compositions comprising one or more effective substances and optionally one or more pharmaceutically acceptable carrier, diluents, excipients and/or auxiliary agents.

Moreover, the pharmaceutical composition of the present invention can be administered in a suitable dosage which depends e.g. on the efficacy of the respective ligand in use via any appropriate route such as parenterally, orally, (sub)cutaneously or sublingually or it can be injected into an organ of a patient in need thereof.

Another aspect of the present invention relates to a crystal form of the amyloid precursor protein intracellular domain (AICD) in complex with human Fe65-PTB2.

According to the present invention, the way to obtain said crystal form is not especially restricted, and includes, for example, the crystallization of AICD in complex with human Fe65-PTB2 using sitting, hanging or sandwich drop crystallization, free interface diffusion, batch crystallization, microdialysis crystallization, or crystallization under oil. According to the present invention vapor-diffusion based crystallization methods, such as hanging or sitting drop crystallization, are preferred.

The substances required for crystallizing e.g. AICD (or AICD-C31/32), with Fe65 (or Fe65-PTB2) may be obtained by any method known in the art, such as recombinant synthesis thereof in a host microorganism, direct synthesis by solid phase peptide synthesis, or extraction from human or animal cells. According to the present invention, the preparation of AICD and Fe65-PTB2, or fragments thereof, is preferably performed by transfection of host cells with one or more vectors comprising nucleic acid sequences which encode the AICD and Fe65-PTB2 proteins.

In a preferred embodiment of the present invention, the above-defined crystal form is defined as a crystal of hexagonal space group $P6_1$ having the cell constants a=b=114.3 Å±15%, c=74.8 Å±15%, $\alpha=\beta=90°$ and $\gamma=120°$.

The three-dimensional structure of AICD in complex with Fe65-PTB2 as disclosed herein is surprisingly suitable for elucidating the processes which take place in the development of neurodegenerative disorders, such as Alzheimer's disease (AD). In particular, the three-dimensional structure according to the present invention advantageously allows the identification and/or development of ligands which modify the interaction between APP, the main source of amyloid-β peptide (Aβ), and the human adaptor protein Fe65. The identification and/or development of ligands capable of effectively modifying the above-mentioned interaction is considered to yield highly effective compounds, e.g. in form of a pharmaceutical composition, for preventing or treating neuronal disorders, such as AD.

The figures show:

FIG. 1 shows the atomic coordinates of a three-dimensional structure of the amyloid precursor protein intracellular domain (AICD) in complex with human Fe65-PTB2.

FIG. 2 shows the atomic coordinates of a three-dimensional structure of the amyloid precursor protein intracellular domain (AICD). Said structure has been derived from the structure of AICD and Fe65-PTB2 in complex.

FIG. 3 shows the atomic coordinates of a three-dimensional structure of the human Fe65 C-terminal phosphotyrosine binding domain (Fe65-PTB2). Said structure has been derived from the structure of Fe65-PTB2 and AICD in complex.

Figure 4:
FIG. 4 shows a ribbon model of the AICD/Fe65-PTB2 complex.
Figure 5:
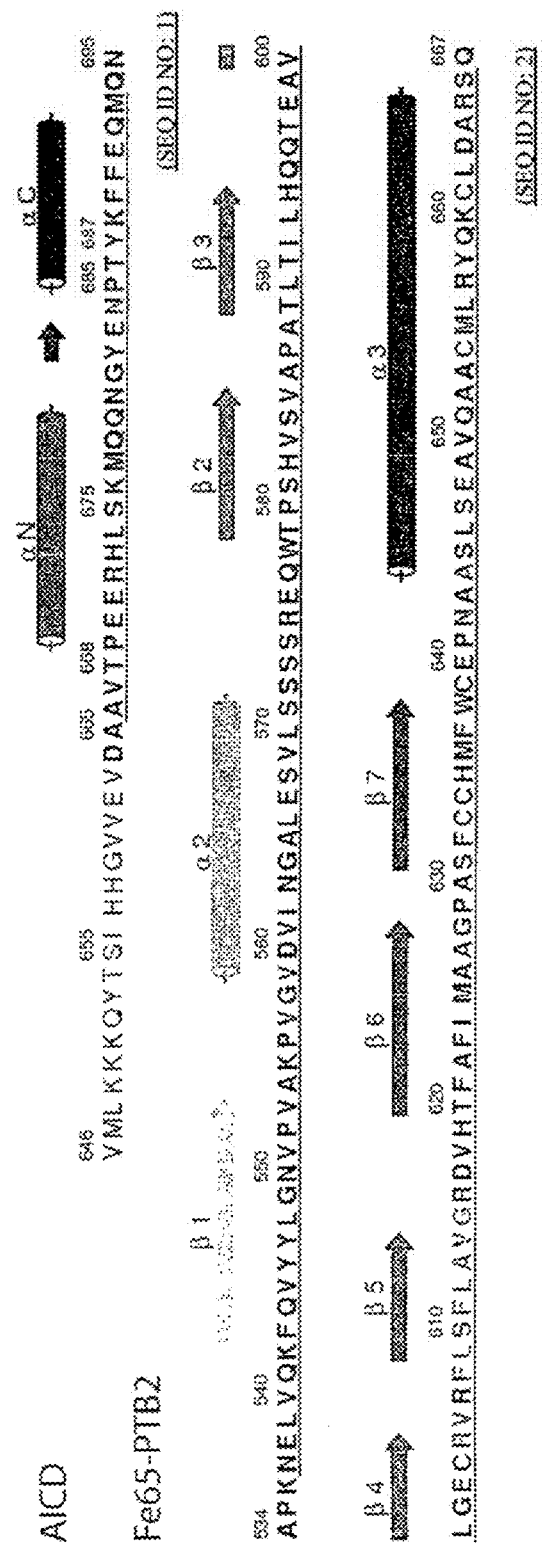
FIG. 5 shows the primary and secondary structure of the AICD/Fe65-PTB2 complex.

The present invention will be further illustrated in the following examples, without any limitation thereto.

EXAMPLES

Example 1

Cloning and Protein Expression

A gene fragment encoding the human Fe65-PTB2 domain comprising the residues 534 to 666 (SEQ ID NO: 2) has been amplified by polymerase chain reaction (PCR) with the primers Fe65PTB2_F (SEQ ID NO: 7) and Fe65PTB2_R (SEQ ID NO: 8). The PCR product was cloned into the NcoI and XhoI sites of the pET21d vector (Novagen) in frame with the C-terminal hexa-histidine tag encoded by the vector.

The gene coding for the human AICD (residues 646 to 695 in respect to neuronal APP695 numbering) was amplified using the primers APP_C50_F (SEQ ID NO: 3) and APP_C50_R (SEQ ID NO: 4) and cloned into the NdeI and HindIII sites of the pET25b vector (Novagen). The construct comprising the final C-terminal 50 amino acids (amino acid residues 646 to 695) of APP was amplified using the primers APP_C32_F (SEQ ID NO: 5) and APP_C32_R (SEQ ID NO: 6) and cloned into the NcoI and HindIII cleavage sites of the pETtrx__1b. While the AICD was untagged the AICD-C32 construct was fused to thioredoxin and a hexa-histidine tag containing a TEV cleavage site in between. All constructs were verified by DNA sequencing.

All recombinant proteins were overexpressed in *Escherichia coli* BL21 (DE3) RIL cells. Cells expressing the Fe65-PTB2 or the AICD were grown in terrific-broth (TB) medium containing ampicillin (100 mg·l$^{-1}$) while cells expressing the AICD-C32 construct were grown in LB medium containing kanamycin (30 mg·l$^{-1}$). All cells were incubated at 310 K until the optical density reached ~0.8 and expression was induced with 1 mM isopropyl-D-thiogalactopyranoside (IPTG). After induction cells expressing the AICD or the AICD-C32 fragment were incubated at 310 K for 4 hours while the expression of the Fe65-PTB2 was done at 293 K for 16 hours. Cells were harvested by centrifugation for 20 min at 5000 g and 277 K and frozen at 193 K.

Example 2

Purification

Cell pellets were resuspended in 10 ml lysis buffer per gram of cells and the protein was extracted by a combination of sonification and by passing through a M1-10L Microfluidizer (Microfluidics). For Fe65-PTB2 and AICD-C32 the lysis buffer contained 300 mM NaCl, 50 mM Tris pH 8.0, 10 mM imidazole, and 0.02% (v/v) 1-thioglycerol. The cell lysate was centrifuged at 125000 g at 277 K and the supernatant was applied to a 1 ml His-Trap HP column (GE Healthcare). The column was washed with 10 column volumes lysis buffer for the AICD-C32 and with lysis buffer containing 30 mM imidazole for the Fe65-PTB2. Both proteins were eluted from the column in lysis buffer containing 300 mM imidazole.

To remove the thioredoxin and the hexa-histidine-tag from the AICD-C32 the eluted protein was concentrated using an Amicon Ultracel-5K (Millipore) to a final volume of 2.5 ml and applied to a PD10 column (GE Healthcare) equilibrated in a buffer containing 200 mM NaCl, 20 mM Tris pH 8.0 and 1 mM DTT. The fusion protein was cleaved over night at 277 K by adding 200 µg of recombinant TEV protease. After digestion the sample was again applied to a 1 ml His-Trap HP column and the flow-through containing the AICD-C32 peptide was collected. Both Fe65-PTB2 and the AICD-C32 were further purified on a S30 16/60 size exclusion column equilibrated in 150 mM NaCl, 10 mM Tris pH 8.0.

For the complete AICD construct the lysis buffer contained 150 mM NaCl, 50 mM Tris pH 7.5 and 1 µg/ml lysozyme. Prior to protein extraction the cells were incubated for one hour at 277 K. The cell lysate was centrifuged at 20000 g and 277 K. The pellet fraction containing the protein in inclusion bodies (IBs) was washed five times in lysis buffer without lysozyme but with 1.0 (v/v) % lauryl-dimethylamine-N-oxide (LDAO) and afterward two times in lysis buffer without detergent. The purified IBs were solubilized in 6 M guanidiniumhydrochlorid (GdnHCl) and afterwards diluted with water to a final concentration of 4 M GdnHCl. Refolding of the AICD was performed by the rapid dilution method with 150 mM NaCl, 100 mM Tris pH 7.5 and 0.8 M L-arginine as refolding buffer. The refolded protein was finally purified on a S30 16/60 size exclusion column as described above. Complex formation between Fe65-PTB2 and AICD or AICD-C32 was performed by the addition of the respective AICD construct in a 1.5:1 access and an incubation of the binding partners for 1 h at 277 K. In both cases the resulting complex was applied to a S30 16/60 size exclusion column as described above. Prior to crystallization experiments the protein was concentrated using an Amicon Ultracel-5K (Millipore).

Example 3

Crystallization

Initial crystallization trials of the complex containing Fe65-PTB2 and AICD or AICD-C32 were performed using the Nextal screen formulations (Qiagen) and crystallization drops have been set with a *Phoenix* crystallization robot (Art Robbins). Crystallization optimization was done by the hanging-drop vapour-diffusion method at 277 K, 284 K or 293 K. The reservoir was mixed with protein solution in a 1:1 ratio. Crystals were flash-cooled in liquid nitrogen prior to diffraction experiments and after rapid soaking in mother liquor supplemented by 20% (v/v) ethylene glycol.

Example 4

Data Collection and Phasing

Diffraction data on the Fe65-PTB2/AICD-C32 complex crystals were collected at beamline ID14-eh2 at the European Synchrotron Radiation Facility (ESRF) in Grenoble (France) at cryogenic temperatures (100 K) on an ADSC Q4 CCD detector. Data were processed with program MOSFLM and scaled with SCALA from the CCP4 program suite (Collaborative Computational Project No. 4). For the molecular replacement method we used program PHASER with the pdb entry 1OQN as search model.

Example 5

Model Building, Refinement, and Validation

The model was built using the program Coot and refinement was carried out with REFMAC5 from the Collaborative Computational Project No. 4 (CCP4). The quality of the model was checked using PROCHECK and WHAT-IF.

---

The invention claimed is:

1. A crystal form of a protein-complex of an intracellular domain (AICD) of human amyloid precursor protein (APP695) consisting of the amino acid sequence of SEQ ID NO:1 in complex with human Fe65-PTB2 consisting of the amino acid sequence of SEQ ID NO:2, wherein the crystal form is in hexagonal space group $P6_1$ and has the cell constants a=b=114.3 Å±15%, c=74.8 Å±15%, $\alpha=\beta=90°$ and $\gamma=120°$.

2. The crystal form of claim 1, wherein the three-dimensional structure of said protein-complex has the structural coordinates of FIG. 1.

* * * * *

SEQUENCE LISTING

```
<160> NUMBER OF SEQ ID NOS: 12

<210> SEQ ID NO 1
<211> LENGTH: 50
<212> TYPE: PRT
<213> ORGANISM: Homo sapiens

<400> SEQUENCE: 1

Val Met Leu Lys Lys Lys Gln Tyr Thr Ser Ile His His Gly Val Val
1               5                   10                  15

Glu Val Asp Ala Ala Val Thr Pro Glu Glu Arg His Leu Ser Lys Met
            20                  25                  30

Gln Gln Asn Gly Tyr Glu Asn Pro Thr Tyr Lys Phe Phe Glu Gln Met
        35                  40                  45

Gln Asn
```

-continued

```
                50

<210> SEQ ID NO 2
<211> LENGTH: 134
<212> TYPE: PRT
<213> ORGANISM: Homo sapiens

<400> SEQUENCE: 2

Ala Pro Lys Asn Glu Leu Val Gln Lys Phe Gln Val Tyr Tyr Leu Gly
1               5                   10                  15

Asn Val Pro Val Ala Lys Pro Val Gly Val Asp Val Ile Asn Gly Ala
            20                  25                  30

Leu Glu Ser Val Leu Ser Ser Ser Arg Glu Gln Trp Thr Pro Ser
        35                  40                  45

His Val Ser Val Ala Pro Ala Thr Leu Thr Ile Leu His Gln Gln Thr
    50                  55                  60

Glu Ala Val Leu Gly Glu Cys Arg Val Arg Phe Leu Ser Phe Leu Ala
65                  70                  75                  80

Val Gly Arg Asp Val His Thr Phe Ala Phe Ile Met Ala Ala Gly Pro
                85                  90                  95

Ala Ser Phe Cys Cys His Met Phe Trp Cys Glu Pro Asn Ala Ala Ser
            100                 105                 110

Leu Ser Glu Ala Val Gln Ala Ala Cys Met Leu Arg Tyr Gln Lys Cys
        115                 120                 125

Leu Asp Ala Arg Ser Gln
        130

<210> SEQ ID NO 3
<211> LENGTH: 25
<212> TYPE: DNA
<213> ORGANISM: Artificial Sequence
<220> FEATURE:
<223> OTHER INFORMATION: Synthetic (Primer: APP_C50 F)

<400> SEQUENCE: 3
gtaccatatg gtgatgctga agaag                                         25

<210> SEQ ID NO 4
<211> LENGTH: 32
<212> TYPE: DNA
<213> ORGANISM: Artificial Sequence
<220> FEATURE:
<223> OTHER INFORMATION: Synthetic (Primer: APP_C50 R)

<400> SEQUENCE: 4
gtacaagctt ctagttctgc atctgctcaa ag                                 32

<210> SEQ ID NO 5
<211> LENGTH: 30
<212> TYPE: DNA
<213> ORGANISM: Artificial Sequence
<220> FEATURE:
<223> OTHER INFORMATION: Synthetic (Primer: APP_C32 F)

<400> SEQUENCE: 5
gtacccatgg acgccgctgt caccccagag                                    30

<210> SEQ ID NO 6
<211> LENGTH: 32
<212> TYPE: DNA
<213> ORGANISM: Artificial Sequence
<220> FEATURE:
```

<223> OTHER INFORMATION: Synthetic (Primer: APP_C32 R)

<400> SEQUENCE: 6
gtacaagctt ctagttctgc atctgctcaa ag                                    32

<210> SEQ ID NO 7
<211> LENGTH: 31
<212> TYPE: DNA
<213> ORGANISM: Artificial Sequence
<220> FEATURE:
<223> OTHER INFORMATION: Synthetic (Primer: Fe65_PTB2 F)

<400> SEQUENCE: 7
gtacccatgg gcgcgcctaa gaatgagttg g                                     31

<210> SEQ ID NO 8
<211> LENGTH: 27
<212> TYPE: DNA
<213> ORGANISM: Artificial Sequence
<220> FEATURE:
<223> OTHER INFORMATION: Synthetic (Primer: FE65_PTB2 R)

<400> SEQUENCE: 8
gtacctcgag cctgggaacg ggcatcc                                          27

<210> SEQ ID NO 9
<211> LENGTH: 32
<212> TYPE: PRT
<213> ORGANISM: Homo sapiens

<400> SEQUENCE: 9

Asp Ala Ala Val Thr Pro Glu Glu Arg His Leu Ser Lys Met Gln Gln
1               5                   10                  15

Asn Gly Tyr Glu Asn Pro Thr Tyr Lys Phe Phe Glu Gln Met Gln Asn
            20                  25                  30

<210> SEQ ID NO 10
<211> LENGTH: 158
<212> TYPE: PRT
<213> ORGANISM: Homo sapiens

<400> SEQUENCE: 10

Asn Glu Leu Val Gln Lys Phe Gln Val Tyr Tyr Leu Gly Asn Val Pro
1               5                   10                  15

Val Ala Lys Pro Val Gly Val Asp Val Ile Asn Gly Ala Leu Glu Ser
            20                  25                  30

Val Leu Ser Ser Ser Ser Arg Glu Gln Trp Thr Pro Ser His Val Ser
        35                  40                  45

Val Ala Pro Ala Thr Leu Thr Ile Leu His Gln Gln Thr Glu Ala Val
    50                  55                  60

Leu Gly Glu Cys Arg Val Arg Phe Leu Ser Phe Leu Ala Val Gly Arg
65                  70                  75                  80

Asp Val His Thr Phe Ala Phe Ile Met Ala Ala Gly Pro Ala Ser Phe
                85                  90                  95

Cys Cys His Met Phe Trp Cys Glu Pro Asn Ala Ala Ser Leu Ser Glu
            100                 105                 110

Ala Val Gln Ala Ala Cys Met Leu Arg Tyr Gln Lys Cys Leu Asp Ala
        115                 120                 125

Arg Ser Ala Val Thr Pro Glu Glu Arg His Leu Ser Lys Met Gln Gln
    130                 135                 140

```
<210> SEQ ID NO 11
<211> LENGTH: 28
<212> TYPE: PRT
<213> ORGANISM: Homo sapiens

<400> SEQUENCE: 11

Ala Val Thr Pro Glu Glu Arg His Leu Ser Lys Met Gln Gln Asn Gly
1               5                   10                  15
Tyr Glu Asn Pro Thr Tyr Lys Phe Phe Glu Gln Met
                20                  25

<210> SEQ ID NO 12
<211> LENGTH: 130
<212> TYPE: PRT
<213> ORGANISM: Homo sapiens

<400> SEQUENCE: 12

Asn Glu Leu Val Gln Lys Phe Gln Val Tyr Tyr Leu Gly Asn Val Pro
1               5                   10                  15
Val Ala Lys Pro Val Gly Val Asp Val Ile Asn Gly Ala Leu Glu Ser
                20                  25                  30
Val Leu Ser Ser Ser Arg Glu Gln Trp Thr Pro Ser His Val Ser
                35                  40                  45
Val Ala Pro Ala Thr Leu Thr Ile Leu His Gln Gln Thr Glu Ala Val
        50                  55                  60
Leu Gly Glu Cys Arg Val Arg Phe Leu Ser Phe Leu Ala Val Gly Arg
65                  70                  75                  80
Asp Val His Thr Phe Ala Phe Ile Met Ala Ala Gly Pro Ala Ser Phe
                85                  90                  95
Cys Cys His Met Phe Trp Cys Glu Pro Asn Ala Ala Ser Leu Ser Glu
                100                 105                 110
Ala Val Gln Ala Ala Cys Met Leu Arg Tyr Gln Lys Cys Leu Asp Ala
                115                 120                 125
Arg Ser
    130
```